(12) United States Patent
Wong et al.

(10) Patent No.: US 10,338,069 B2
(45) Date of Patent: Jul. 2, 2019

(54) GLYCAN ARRAYS FOR HIGH THROUGHPUT SCREENING OF VIRUSES

(75) Inventors: Chi-Huey Wong, La Jolla, CA (US); Chung-Yi Wu, Taipei (TW); Chi-Hui Liang, Taipei (TW); An-Suei Yang, Taipei (TW)

(73) Assignee: ACADEMIA SINICA, Taipei (TW)

( * ) Notice: Subject to any disclaimer, the term of this patent is extended or adjusted under 35 U.S.C. 154(b) by 1379 days.

(21) Appl. No.: 14/376,837

(22) PCT Filed: Apr. 12, 2011

(86) PCT No.: PCT/US2011/032192
§ 371 (c)(1),
(2), (4) Date: Feb. 25, 2015

(87) PCT Pub. No.: WO2011/130332
PCT Pub. Date: Oct. 20, 2011

(65) Prior Publication Data
US 2015/0160217 A1    Jun. 11, 2015

Related U.S. Application Data

(60) Provisional application No. 61/323,300, filed on Apr. 12, 2010.

(51) Int. Cl.
G01N 33/569    (2006.01)
G01N 33/53    (2006.01)
G01N 33/543    (2006.01)

(52) U.S. Cl.
CPC ....... *G01N 33/56983* (2013.01); *G01N 33/53* (2013.01); *G01N 33/54346* (2013.01); *G01N 2333/11* (2013.01); *G01N 2400/00* (2013.01); *G01N 2400/38* (2013.01); *G01N 2458/00* (2013.01)

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. | |
| 3,896,111 A | 7/1975 | Kupchan et al. | |
| 4,137,230 A | 1/1979 | Hashimoto et al. | |
| 4,151,042 A | 4/1979 | Higashide et al. | |
| 4,248,870 A | 2/1981 | Miyashita et al. | |
| 4,256,746 A | 3/1981 | Miyashita et al. | |
| 4,260,608 A | 4/1981 | Miyashita et al. | |
| 4,265,814 A | 5/1981 | Hashimoto et al. | |
| 4,270,537 A | 6/1981 | Romaine | |
| 4,294,757 A | 10/1981 | Asai | |
| 4,307,016 A | 12/1981 | Asai et al. | |
| 4,308,268 A | 12/1981 | Miyashita et al. | |
| 4,308,269 A | 12/1981 | Miyashita et al. | |
| 4,309,428 A | 1/1982 | Miyashita et al. | |
| 4,313,946 A | 2/1982 | Powell et al. | |
| 4,315,929 A | 2/1982 | Freedman et al. | |
| 4,317,821 A | 3/1982 | Miyashita et al. | |
| 4,322,348 A | 3/1982 | Asai et al. | |
| 4,331,598 A | 5/1982 | Hasegawa et al. | |
| RE30,985 E | 6/1982 | Cartaya | |
| 4,361,650 A | 11/1982 | Asai et al. | |
| 4,362,663 A | 12/1982 | Kida et al. | |
| 4,364,866 A | 12/1982 | Asai et al. | |
| 4,371,533 A | 2/1983 | Akimoto et al. | |
| 4,376,110 A | 3/1983 | David et al. | |
| 4,419,446 A | 12/1983 | Howley et al. | |
| 4,424,219 A | 1/1984 | Hashimoto et al. | |
| 4,450,254 A | 5/1984 | Isley et al. | |
| 4,560,655 A | 12/1985 | Baker | |
| 4,596,556 A | 6/1986 | Morrow et al. | |
| 4,596,792 A | 6/1986 | Vyas | |
| 4,599,230 A | 7/1986 | Milich et al. | |
| 4,599,231 A | 7/1986 | Milich et al. | |
| 4,601,903 A | 7/1986 | Frasch | |
| 4,601,978 A | 7/1986 | Karin | |

(Continued)

FOREIGN PATENT DOCUMENTS

EP    0404097 A2    12/1990
EP    0341735 B1    9/1992

(Continued)

OTHER PUBLICATIONS

Stevens et al. (Journal of molecular biology 355.5 (2006): 1143-1155).*
Liang, Chi-Hui, et al. "Iron oxide/gold core/shell nanoparticles for ultrasensitive detection of carbohydrate-protein interactions." Analytical chemistry 81.18 (2009): 7750-7756.*
Wang et al.( Proceedings of the National Academy of Sciences 106.43 (2009): 18137-18142.).*
Kim et al. (Chemistry & biology 15.3 (2008): 215-223..).*
Gao et al. (Analytical chemistry 80.22 (2008): 8822-8827, published online Oct. 15, 2008.) . (Year: 2008).*
Tripp, Ralph A., et al. Bioconjugated nanoparticle detection of respiratory syncytial virus infection.International journal of nanomedicine (2007): pp. 117-124. (Year: 2007).*

(Continued)

*Primary Examiner* — Tracy Vivlemore
*Assistant Examiner* — Sahana S Kaup
(74) *Attorney, Agent, or Firm* — Duane Morris, LLP

(57) ABSTRACT

Glycan arrays that can detect and distinguish between various sub-types and strains of influenza virus are provided. Methods for using the glycan arrays with assays using nanoparticle amplification technique are disclosed. Sandwich assays using gold nanoparticles conjugated to phage particles comprising influenza virus-specific antibodies for detecting multiple serotypes using a single reaction are provided. Plurality of glycans directed to specific target HA of influenza virus comprises the array. Detector molecules comprising noble metals conjugated to (a) phage display particles expressing antibodies against hemagglutinin and (b) neuraminidase binding agents are disclosed.

46 Claims, 13 Drawing Sheets

(12 of 13 Drawing Sheet(s) Filed in Color)

(56) References Cited

U.S. PATENT DOCUMENTS

| | | |
|---|---|---|
| 4,657,866 A | 4/1987 | Kumar |
| 4,676,980 A | 6/1987 | Segal et al. |
| 4,741,900 A | 5/1988 | Alvarez et al. |
| 4,767,704 A | 8/1988 | Cleveland et al. |
| 4,790,824 A | 12/1988 | Morrow et al. |
| 4,816,567 A | 3/1989 | Cabilly et al. |
| 4,849,222 A | 7/1989 | Broaddus |
| 4,886,499 A | 12/1989 | Cirelli et al. |
| 4,927,762 A | 5/1990 | Darfler |
| 4,940,460 A | 7/1990 | Casey et al. |
| 4,941,880 A | 7/1990 | Burns |
| 4,965,199 A | 10/1990 | Capon et al. |
| 4,970,198 A | 11/1990 | Lee et al. |
| 4,975,278 A | 12/1990 | Senter et al. |
| 5,004,697 A | 4/1991 | Pardridge |
| 5,015,235 A | 5/1991 | Crossman |
| 5,053,394 A | 10/1991 | Ellestad et al. |
| 5,061,620 A | 10/1991 | Tsukamoto et al. |
| 5,064,413 A | 11/1991 | McKinnon et al. |
| 5,075,109 A | 12/1991 | Tice et al. |
| 5,079,233 A | 1/1992 | Lee |
| 5,100,669 A | 3/1992 | Hyon et al. |
| 5,112,596 A | 5/1992 | Malfroy-Camine |
| 5,122,469 A | 6/1992 | Mather et al. |
| 5,141,496 A | 8/1992 | Dalto et al. |
| 5,190,521 A | 3/1993 | Hubbard et al. |
| 5,208,020 A | 5/1993 | Chari et al. |
| 5,229,275 A | 7/1993 | Goroff |
| 5,264,365 A | 11/1993 | Georgiou et al. |
| 5,268,164 A | 12/1993 | Kozarich et al. |
| 5,312,335 A | 5/1994 | McKinnon et al. |
| 5,326,856 A | 7/1994 | Coughlin et al. |
| 5,328,483 A | 7/1994 | Jacoby |
| 5,334,144 A | 8/1994 | Alchas et al. |
| 5,339,163 A | 8/1994 | Homma et al. |
| 5,362,852 A | 11/1994 | Geoghegan |
| 5,369,017 A | 11/1994 | Wong et al. |
| 5,374,541 A | 12/1994 | Wong et al. |
| 5,383,851 A | 1/1995 | McKinnon, Jr. et al. |
| 5,395,541 A | 3/1995 | Carpenter et al. |
| 5,416,064 A | 5/1995 | Chari et al. |
| 5,417,662 A | 5/1995 | Hjertman et al. |
| 5,466,220 A | 11/1995 | Brenneman |
| 5,480,381 A | 1/1996 | Weston |
| 5,500,362 A | 3/1996 | Robinson et al. |
| 5,503,627 A | 4/1996 | McKinnon et al. |
| 5,506,206 A | 4/1996 | Kozarich et al. |
| 5,508,192 A | 4/1996 | Georgiou et al. |
| 5,518,725 A | 5/1996 | Daynes et al. |
| 5,520,639 A | 5/1996 | Peterson et al. |
| 5,527,288 A | 6/1996 | Gross et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,569,189 A | 10/1996 | Parsons |
| 5,569,825 A | 10/1996 | Lonberg et al. |
| 5,571,894 A | 11/1996 | Wels et al. |
| 5,580,717 A | 12/1996 | Dower et al. |
| 5,585,089 A | 12/1996 | Queen et al. |
| 5,587,458 A | 12/1996 | King et al. |
| 5,591,669 A | 1/1997 | Krimpenfort et al. |
| 5,591,828 A | 1/1997 | Bosslet et al. |
| 5,599,302 A | 2/1997 | Lilley et al. |
| 5,606,040 A | 2/1997 | McGahren et al. |
| 5,624,821 A | 4/1997 | Winter et al. |
| 5,625,126 A | 4/1997 | Lonberg et al. |
| 5,633,425 A | 5/1997 | Lonberg et al. |
| 5,635,483 A | 6/1997 | Pettit et al. |
| 5,639,635 A | 6/1997 | Joly et al. |
| 5,641,870 A | 6/1997 | Rinderknecht et al. |
| 5,643,577 A | 7/1997 | Pang et al. |
| 5,648,237 A | 7/1997 | Carter |
| 5,648,260 A | 7/1997 | Winter et al. |
| 5,649,912 A | 7/1997 | Peterson |
| 5,661,016 A | 8/1997 | Lonberg et al. |
| 5,663,149 A | 9/1997 | Pettit et al. |
| 5,674,988 A | 10/1997 | Sabesan |
| 5,677,180 A | 10/1997 | Robinson et al. |
| 5,686,416 A | 11/1997 | Kozarich et al. |
| 5,690,938 A | 11/1997 | Ermak et al. |
| 5,693,762 A | 12/1997 | Queen et al. |
| 5,704,911 A | 1/1998 | Parsons |
| 5,712,374 A | 1/1998 | Kuntsman et al. |
| 5,714,374 A | 2/1998 | Arnold et al. |
| 5,714,586 A | 2/1998 | Kunstman et al. |
| 5,731,168 A | 3/1998 | Cater et al. |
| 5,733,743 A | 3/1998 | Johnson et al. |
| 5,736,137 A | 4/1998 | Anderson et al. |
| 5,739,116 A | 4/1998 | Hamann et al. |
| 5,767,285 A | 6/1998 | Hamann et al. |
| 5,770,701 A | 6/1998 | McGahren et al. |
| 5,773,001 A | 6/1998 | Hamann et al. |
| 5,780,588 A | 7/1998 | Pettit et al. |
| 5,814,344 A | 9/1998 | Tice et al. |
| 5,820,883 A | 10/1998 | Tice et al. |
| 5,821,337 A | 10/1998 | Carter et al. |
| 5,837,234 A | 11/1998 | Gentile et al. |
| 5,840,523 A | 11/1998 | Simmons et al. |
| 5,849,716 A | 12/1998 | Akimoto |
| 5,853,763 A | 12/1998 | Tice et al. |
| 5,869,046 A | 2/1999 | Presta et al. |
| 5,877,296 A | 3/1999 | Hamann et al. |
| 5,893,397 A | 4/1999 | Peterson et al. |
| 5,993,412 A | 11/1999 | Deily et al. |
| 6,004,940 A | 12/1999 | Marasco et al. |
| 6,027,888 A | 2/2000 | Georgiou et al. |
| 6,083,715 A | 7/2000 | Georgiou et al. |
| 6,111,132 A | 8/2000 | Kim et al. |
| 6,143,724 A | 11/2000 | Ohira et al. |
| 6,210,670 B1 | 4/2001 | Berg |
| 6,265,150 B1 | 7/2001 | Terstappen et al. |
| 6,329,173 B1 | 12/2001 | Marasco et al. |
| 6,340,702 B1 | 1/2002 | Honda et al. |
| 6,399,071 B1 | 6/2002 | Duthaler |
| 6,455,571 B1 | 9/2002 | Maring et al. |
| 6,506,564 B1 | 1/2003 | Mirkin et al. |
| 6,528,286 B1 | 3/2003 | Ryll |
| 6,548,476 B1 | 4/2003 | Wu et al. |
| 6,680,054 B1 | 1/2004 | Reece et al. |
| 6,696,304 B1 | 2/2004 | Davies |
| 6,703,019 B1 | 3/2004 | Malfroy-Camine |
| 6,824,780 B1 | 11/2004 | Devaux et al. |
| 6,855,551 B2 | 2/2005 | Bawendi et al. |
| 6,873,914 B2 | 3/2005 | Winfield et al. |
| 6,984,630 B1 | 1/2006 | Descamps et al. |
| 6,994,966 B2 | 2/2006 | Dukler |
| 7,019,288 B2 | 3/2006 | Becker |
| 7,090,973 B1 | 8/2006 | Breton |
| 7,151,164 B2 | 12/2006 | Hansen et al. |
| 7,157,433 B2 | 1/2007 | Mercep et al. |
| 7,205,333 B2 | 4/2007 | Wu et al. |
| 7,488,491 B2 | 2/2009 | Tsjui et al. |
| 7,498,298 B2 | 3/2009 | Doronina et al. |
| 7,854,934 B2 | 12/2010 | Danishefsky |
| 7,888,337 B2 | 2/2011 | Wong et al. |
| 7,923,013 B2 | 4/2011 | Tsuji et al. |
| 7,928,077 B2 | 4/2011 | Wong et al. |
| 7,943,330 B2 | 5/2011 | Wong et al. |
| 7,960,139 B2 | 6/2011 | Sawa et al. |
| 7,977,097 B1 | 7/2011 | Gay et al. |
| 8,022,043 B2 | 9/2011 | Porcelli |
| 8,088,387 B2 | 1/2012 | Steeves et al. |
| 8,101,179 B2 | 1/2012 | Numazaki et al. |
| 8,268,969 B2 | 9/2012 | Wong et al. |
| 8,383,554 B2 | 2/2013 | Wong et al. |
| 8,507,660 B2 | 8/2013 | Wong et al. |
| 8,680,020 B2 | 3/2014 | Wong et al. |
| 8,715,963 B2 | 5/2014 | Sethuraman |
| 8,716,465 B2 | 5/2014 | Rossi et al. |
| 8,802,438 B2 | 8/2014 | Rossi et al. |
| 8,815,941 B2 | 8/2014 | Withers |
| 8,883,506 B2 | 11/2014 | Rossi et al. |
| 8,906,832 B2 | 12/2014 | Wong et al. |

(56) References Cited

U.S. PATENT DOCUMENTS

| | | |
|---|---|---|
| 8,907,111 B2 | 12/2014 | Withers |
| 9,187,552 B2 | 11/2015 | Stadheim |
| 9,221,859 B2 | 12/2015 | Withers |
| 9,382,284 B2 | 7/2016 | Withers |
| 9,434,786 B2 | 9/2016 | Wang |
| 9,759,726 B2 | 9/2017 | Wong et al. |
| 9,803,177 B2 | 10/2017 | Rossi et al. |
| 9,914,956 B2 | 3/2018 | Wong et al. |
| 10,005,847 B2 | 6/2018 | Wong |
| 10,023,892 B2 | 7/2018 | Wong |
| 10,118,969 B2 | 11/2018 | Wong |
| 2002/0025313 A1 | 2/2002 | Micklus et al. |
| 2002/0038086 A1 | 3/2002 | Hynynen et al. |
| 2002/0065259 A1 | 5/2002 | Schatzberg et al. |
| 2003/0073713 A1 | 4/2003 | Schoenhard |
| 2003/0083299 A1 | 5/2003 | Ferguson |
| 2003/0104402 A1 | 6/2003 | Zauderer et al. |
| 2003/0118592 A1 | 6/2003 | Ledbetter et al. |
| 2003/0129186 A1 | 7/2003 | Beliveau et al. |
| 2003/0162695 A1 | 8/2003 | Schatzberg et al. |
| 2003/0175884 A1 | 9/2003 | Umana et al. |
| 2003/0219433 A1 | 11/2003 | Hansen et al. |
| 2004/0072290 A1 | 4/2004 | Umana et al. |
| 2004/0086423 A1 | 5/2004 | Wohlstadter |
| 2004/0131692 A1 | 7/2004 | Kreuter et al. |
| 2004/0137557 A1 | 7/2004 | DeFrees et al. |
| 2004/0204354 A1 | 10/2004 | Nelson et al. |
| 2004/0259142 A1 | 12/2004 | Chai et al. |
| 2005/0085413 A1 | 4/2005 | Jin et al. |
| 2005/0089473 A1 | 4/2005 | Black et al. |
| 2005/0106108 A1 | 5/2005 | Hansen et al. |
| 2005/0123546 A1 | 6/2005 | Umana et al. |
| 2005/0124533 A1 | 6/2005 | Schatzberg et al. |
| 2005/0221337 A1 | 10/2005 | Seeberger et al. |
| 2005/0221397 A1 | 10/2005 | Saito |
| 2005/0255491 A1 | 11/2005 | Lee |
| 2006/0019256 A1 | 1/2006 | Clarke et al. |
| 2006/0073122 A1 | 4/2006 | Koezuka et al. |
| 2006/0073161 A1 | 4/2006 | Breton |
| 2006/0211856 A1 | 9/2006 | Tsuji et al. |
| 2006/0286140 A1 | 12/2006 | Wickstrom et al. |
| 2006/0286637 A1 | 12/2006 | Hamilton |
| 2007/0059769 A1* | 3/2007 | Blixt .............. G01N 33/54386 435/7.1 |
| 2007/0065949 A1 | 3/2007 | Hutchens |
| 2007/0207090 A1 | 9/2007 | Giudice |
| 2007/0213278 A1 | 9/2007 | Wong et al. |
| 2007/0213297 A1 | 9/2007 | Wong et al. |
| 2007/0219351 A1 | 9/2007 | Fiume et al. |
| 2007/0224189 A1 | 9/2007 | Lazar et al. |
| 2007/0238871 A1 | 10/2007 | Tsuji et al. |
| 2008/0070324 A1 | 3/2008 | Floyd |
| 2008/0145838 A1 | 6/2008 | Suda et al. |
| 2008/0220988 A1 | 9/2008 | Zhou |
| 2008/0260774 A1 | 10/2008 | Wong et al. |
| 2009/0035179 A1 | 2/2009 | Rakow et al. |
| 2009/0081255 A1 | 3/2009 | Bublot et al. |
| 2009/0123439 A1 | 5/2009 | Yun et al. |
| 2009/0285837 A1 | 11/2009 | Kao et al. |
| 2009/0298797 A1 | 12/2009 | Zheng et al. |
| 2009/0317837 A1 | 12/2009 | Wong et al. |
| 2010/0009339 A1 | 1/2010 | Bovin et al. |
| 2010/0022026 A1 | 1/2010 | Rump et al. |
| 2010/0047827 A1 | 2/2010 | Laine et al. |
| 2010/0047828 A1 | 2/2010 | Sorenson et al. |
| 2010/0068806 A1 | 3/2010 | Laine et al. |
| 2010/0112195 A1 | 5/2010 | Kodas et al. |
| 2010/0113397 A1 | 5/2010 | Wong et al. |
| 2010/0136009 A1 | 6/2010 | Papkoff et al. |
| 2010/0136042 A1 | 6/2010 | Wong et al. |
| 2010/0173323 A1 | 7/2010 | Strome |
| 2011/0086408 A1 | 4/2011 | Power |
| 2011/0104188 A1 | 5/2011 | Tashiro et al. |
| 2011/0124116 A1 | 5/2011 | Wohlstadter et al. |
| 2011/0137570 A1 | 6/2011 | Lapadula et al. |
| 2011/0237459 A1 | 9/2011 | Nova et al. |
| 2011/0263828 A1 | 10/2011 | Wong et al. |
| 2012/0046346 A1 | 2/2012 | Rossi et al. |
| 2012/0171201 A1 | 7/2012 | Sapra |
| 2012/0178705 A1 | 7/2012 | Liang et al. |
| 2012/0178802 A1 | 7/2012 | Withers et al. |
| 2012/0226024 A1 | 9/2012 | Wang et al. |
| 2012/0294859 A1 | 11/2012 | Goletz et al. |
| 2012/0322864 A1 | 12/2012 | Rossi et al. |
| 2012/0322865 A1 | 12/2012 | Rossi et al. |
| 2012/0328646 A1 | 12/2012 | Wong et al. |
| 2013/0189258 A1 | 7/2013 | Rother et al. |
| 2013/0196356 A1 | 8/2013 | Jackson et al. |
| 2013/0230886 A1 | 9/2013 | Votsmeier et al. |
| 2013/0295104 A1 | 11/2013 | Deckert et al. |
| 2013/0337018 A1 | 12/2013 | Fox |
| 2014/0051127 A1 | 2/2014 | Wong et al. |
| 2014/0086916 A1 | 3/2014 | Zha |
| 2014/0127241 A1 | 5/2014 | Leuschner et al. |
| 2014/0178365 A1 | 6/2014 | Ghaderi et al. |
| 2014/0227290 A1 | 8/2014 | Sethuraman |
| 2014/0302028 A1 | 10/2014 | Zha |
| 2014/0308746 A1 | 10/2014 | Rossi et al. |
| 2015/0087814 A1 | 3/2015 | Wang |
| 2015/0160217 A1 | 6/2015 | Wong et al. |
| 2015/0225766 A1 | 8/2015 | Wong et al. |
| 2015/0309041 A1 | 10/2015 | Wong et al. |
| 2015/0344544 A1 | 12/2015 | Wong et al. |
| 2015/0344551 A1 | 12/2015 | Wong et al. |
| 2015/0344559 A1 | 12/2015 | Wong et al. |
| 2015/0344585 A1 | 12/2015 | Wong et al. |
| 2015/0344587 A1 | 12/2015 | Wong et al. |
| 2016/0009803 A1 | 1/2016 | Rother et al. |
| 2016/0102151 A1 | 4/2016 | Wong et al. |
| 2016/0215061 A1 | 7/2016 | Shaeen |
| 2016/0274121 A1 | 9/2016 | Wong et al. |
| 2016/0280794 A1 | 9/2016 | Wong et al. |
| 2016/0289340 A1 | 10/2016 | Wong et al. |
| 2017/0275389 A1 | 9/2017 | Wong et al. |
| 2017/0283878 A1 | 10/2017 | Wong et al. |
| 2017/0362330 A1 | 12/2017 | Liu |

FOREIGN PATENT DOCUMENTS

| | | |
|---|---|---|
| EP | 0425235 B1 | 9/1996 |
| EP | 1208909 A2 | 5/2002 |
| EP | 1391213 A1 | 2/2004 |
| EP | 2123271 | 11/2009 |
| EP | 2187217 A1 | 5/2010 |
| JP | 05-222085 | 8/1993 |
| JP | 05-507068 | 10/1993 |
| JP | 05-339283 A | 12/1993 |
| JP | 11-343295 A | 12/1999 |
| JP | 2005-06008 | 5/2000 |
| JP | 2002-371087 A | 12/2002 |
| JP | 2008-025989 A | 2/2008 |
| WO | WO 87/00195 A1 | 1/1987 |
| WO | WO 90/03430 A1 | 4/1990 |
| WO | WO 91/00360 A1 | 1/1991 |
| WO | WO 91/10741 A1 | 7/1991 |
| WO | WO 92/00373 A1 | 1/1992 |
| WO | WO 92/006691 | 4/1992 |
| WO | WO 92/09690 A2 | 6/1992 |
| WO | WO 93/01161 A1 | 1/1993 |
| WO | WO 93/06213 A1 | 4/1993 |
| WO | WO 93/07861 A1 | 4/1993 |
| WO | WO 93/08829 A1 | 5/1993 |
| WO | WO 93/09764 | 5/1993 |
| WO | WO 93/16185 A2 | 8/1993 |
| WO | WO 93/021232 A1 | 10/1993 |
| WO | WO 94/04690 A1 | 3/1994 |
| WO | WO 94/11026 | 5/1994 |
| WO | WO 94/29351 | 12/1994 |
| WO | WO 95/11010 A1 | 4/1995 |
| WO | WO 96/07754 A1 | 3/1996 |
| WO | WO 96/16673 A1 | 6/1996 |
| WO | WO 96/33735 A1 | 10/1996 |
| WO | WO 96/34096 A1 | 10/1996 |
| WO | WO 97/05267 A2 | 2/1997 |

(56) References Cited

FOREIGN PATENT DOCUMENTS

| WO | WO 97/013537 | | 4/1997 | | |
| --- | --- | --- | --- | --- | --- |
| WO | WO 97/17852 A1 | | 5/1997 | | |
| WO | WO 97/037705 | | 10/1997 | | |
| WO | WO 98/00558 A1 | | 1/1998 | | |
| WO | WO 98/02463 A1 | | 1/1998 | | |
| WO | WO 98/24893 A2 | | 6/1998 | | |
| WO | WO 99/034850 | | 7/1999 | | |
| WO | WO 99/49019 A2 | | 9/1999 | | |
| WO | WO 99/051642 | | 10/1999 | | |
| WO | WO 99/057134 A1 | | 11/1999 | | |
| WO | WO 01/42505 A2 | | 6/2001 | | |
| WO | WO 01/86001 A1 | | 11/2001 | | |
| WO | WO 02/088172 | | 11/2002 | | |
| WO | WO 03/040104 A1 | | 5/2003 | | |
| WO | WO 03/68821 A2 | | 8/2003 | | |
| WO | WO 03/077945 A1 | | 9/2003 | | |
| WO | WO 2004/035607 A2 | | 4/2004 | | |
| WO | WO 2004/056312 A2 | | 7/2004 | | |
| WO | WO 2004/063351 | | 7/2004 | | |
| WO | WO 2004/103404 A1 | | 12/2004 | | |
| WO | WO 2005/030258 A2 | | 4/2005 | | |
| WO | WO 2005/044859 | | 5/2005 | | |
| WO | WO 2005/103081 A2 | | 11/2005 | | |
| WO | WO 2006/055925 A2 | | 5/2006 | | |
| WO | WO 2006/064983 A1 | | 6/2006 | | |
| WO | WO 2006/106959 | | 10/2006 | | |
| WO | WO 2006/126069 A2 | | 11/2006 | | |
| WO | WO 2006/130458 A2 | | 12/2006 | | |
| WO | WO 2007/078873 A1 | | 7/2007 | | |
| WO | WO 2007/0133855 | | 11/2007 | | |
| WO | WO 2007/146847 A2 | | 12/2007 | | |
| WO | WO 2008/020596 A2 | | 2/2008 | | |
| WO | WO 2008/087260 A1 | | 7/2008 | | |
| WO | WO2008118013 | * | 10/2008 | | |
| WO | WO 2008/133801 A1 | | 11/2008 | | |
| WO | WO 2008/0133857 A1 | | 11/2008 | | |
| WO | WO 2009/029888 A3 | | 3/2009 | | |
| WO | WO-2009126735 A1 | * | 10/2009 | ............... | B82Y 5/00 |
| WO | WO 2010/006315 A2 | | 1/2010 | | |
| WO | WO 2010/009271 A1 | | 1/2010 | | |
| WO | WO2010/029302 A2 | | 3/2010 | | |
| WO | WO201011703 | * | 9/2010 | | |
| WO | WO 2011/005756 A1 | | 1/2011 | | |
| WO | WO 2011/006237 A1 | | 1/2011 | | |
| WO | WO 2011/031236 A1 | | 3/2011 | | |
| WO | WO 2011/074621 A1 | | 6/2011 | | |
| WO | WO 2011/089004 A1 | | 7/2011 | | |
| WO | WO 2011/130332 | | 10/2011 | | |
| WO | WO 2011/143262 A2 | | 11/2011 | | |
| WO | WO 2011/145957 A1 | | 11/2011 | | |
| WO | WO 2012/082635 A1 | | 6/2012 | | |
| WO | WO 2012/094540 A2 | | 7/2012 | | |
| WO | WO 2013/011347 A1 | | 1/2013 | | |
| WO | WO 2013/024895 A1 | | 2/2013 | | |
| WO | WO 2013/088395 A1 | | 6/2013 | | |
| WO | WO2013/106937 A1 | | 7/2013 | | |
| WO | WO 2013/120066 A1 | | 8/2013 | | |
| WO | WO 2013/130603 A1 | | 9/2013 | | |
| WO | WO 2013/152034 A1 | | 10/2013 | | |
| WO | WO 2013/155375 A1 | | 10/2013 | | |
| WO | WO 2013/181585 A2 | | 12/2013 | | |
| WO | WO 2014/031498 | | 2/2014 | | |
| WO | WO 2014/078373 A1 | | 5/2014 | | |
| WO | WO 2014/210397 A1 | | 12/2014 | | |
| WO | WO 2014/210564 | | 12/2014 | | |
| WO | WO 2015/026484 A1 | | 2/2015 | | |
| WO | WO 2015/035337 A1 | | 3/2015 | | |
| WO | WO 2015/038963 A1 | | 3/2015 | | |
| WO | WO 2005/088310 A2 | | 9/2015 | | |
| WO | WO 2015/184008 | | 12/2015 | | |
| WO | WO 2016/040369 A2 | | 3/2016 | | |
| WO | WO 2016/118090 A1 | | 7/2016 | | |
| WO | WO 2014/031762 A1 | | 2/2017 | | |

OTHER PUBLICATIONS

Greene, Theodora et al., Protective Groups in Organic Synthesis, pp. 42-51 and 96-100, 1991.
Schelhaas, Michael et al., Protecting Group Strategies in Organic Synthesis, Angew. Chem. Int. Ed. Engl. 1996, 35, 2056-2083.
Unverzagt, Carlo et al., A Double Regio- and Stereoselective Glycosylation Strategy for the Synthesis of N-Glycans, Chem. Eur. J., 2008, 14, 1304-1311.
Cheung et al., Meeting Info: 23rd International Symposium on Glycoconjugates, Glyco 23. Split, Croatia. Sep. 15, 2015-Sep. 20, 2015, vol. 32, No. 5, pp. 323.
Tsai, Charng-Sheng et al., Cell-Permeable Probe for Identification and Imaging of Sialidases, PNAS, vol. 110, No. 7, 2013, 2466-2471.
U.S. Appl. No. 15/005,930, filed Jan. 25, 2016, Wong et al.
U.S. Appl. No. 15/011,543, filed Jan. 30, 2016, Wong et al.
U.S. Appl. No. 15/011,544, filed Jan. 30, 2016, Wong et al.
U.S. Appl. No. 15/173,496, filed Jun. 3, 2016, Wong et al.
Abbas et al., "Functional diversity of helper T lymphocytes," Nature, Oct. 31, 1996, 383(6603):787-793.
Abrahmsén et al, "Analysis of signals for secretion in the staphylococcal protein A gene," Embo J., Dec. 30, 1985, 4(13B):3901-3906.
Achtman, M., Epidemic Spread and Antigenic Variability of Neisseria Meningitidis, Trends Microbial 1995, 3, 186-192.
Adam et al., "Proteomic profiling of mechanistically distinct enzyme classes using a common chemotype," Nat. Biotechnol., Aug. 2002, 20(8):805-809.
Agard, N. et al., A Strain-Promoted [3+2]Azide-Alkyne Cycloaddition for Covalent Modification of Biomolecules in Living Systems, J. Am. Chem. Soc. 2004, 126, 15046-15047.
Ahmadi, T. S. et al., Shape-Controlled Synthesis of Colloidal Platinum Nanoparticles, Science, 272, 1924 (1996).
Ahmed et al.,Structural Characterization of Anti-Inflammatory Immunoglobulin G Fc Proteins, K Mol Biol (2014) 426, 3166-3179.
Altevogt, Peter et al., Different Patterns of Lectin Binding and Cell Surface Sialylation Detected on Related High- and Low-Metastatic Tumor Lines, Cancer Res. 43, 5138-5144, 1983.
Altschul SF et al., "Basic local alignment search tool", J Mol Biol. Oct. 5, 1990;215(3):403-10.
Altschul SF, et al., "Gapped BLAST and PSI-BLAST: a new generation of protein database search programs", Nucleic Acids Res. Sep. 1, 1997;25(17):3389-402.
Amin, M. N. et al. Synthetic glycopeptides reveal the glycan specificity of HIV-neutralizing antibodies. Nat. Chem. Biol. 9, 521-526, (2013.
Anderson et al., "Stimulation of Natural Killer T Cells by Glycolipids", Molecules, May 2013, 18(12), 15662-15688.
Andrews et al., Synthesis and influenza virus sialidase inhibitory activity of analogues of 4-Guanidino-Neu5Ac2en (Zanamivir modified in the glycerol side-chain. Eur J Med Chem Jul.-Aug. 1999;34(7-8):563-74.
Angata et al., "Chemical diversity in the sialic acids and related α-keto acids: an evolutionary perspective," Chem. Rev., Feb. 2002, 102(2):439-469.
Anthony, Robert et al., Recapitulation of IVIG Anti-Inflammatory Activity with a Recombinant IgG Fc, Science Apr. 18, 2008. 320:373-376.
Arase et al., "NK1.1+CD4+CD8− thymocytes with specific lymphokine secretion," Eur. J. Immunol., Jan. 1993, 23(1):307-310.
Arié et al., "Chaperone function of FkpA, a heat shock prolyl isomerase, in the periplasm of Escherichia coli," Mol. Microbiol., Jan. 2001, 39(1):199-210.
Aspeslagh et al., "Galactose-modified iNKT cell agonists stabilized by an induced fit of CD1d prevent tumour metastasis," EMBO J., Jun. 1, 2011, 30(11):2294-2305.
Astronomo, R. D. & Burton, D.R. Carbohydrate vaccines: developing sweet solutions to sticky situations? Nat. Rev. Drug. Discov. 9, 308-324, (2010.
Bachmann, Cellular and Molecular Biology, vol. 2, Chapter 72: Derivations and Genotypes of Some Mutant Derivatives of Escherichia coli K-12, Neidhardt et al., eds.,. 1987, pp. 1190-1219, American Society for Microbiology, Washington, D.C.

(56) References Cited

OTHER PUBLICATIONS

Bacilieri, Magdalena et al., Ligand-Based Drug Design Methodologies in Drug Discovery Process: An Overview, Current Drug Discovery Technologies, vol. 3 (3), Sep. 2006, p. 155-165.
Bacteroides Fragilis NCTC 9343, Complete Genome., Mar. 3, 2005, XP002775523, Database Accession No. CR626927, 2 Pages.
Bacteroides Thetaiotaomicron VPI-5482, Section 8 of 21 of the Complete Genome, XP002775522, Jan. 6, 2006, Database Accession No. AE016933, 2 Pages.
Bai, Dan et al., Exploring Forster Electronic Energy Transfer in a Decoupled Anthracenyl-based Borondipyrromethene (Bodipy) Dyad, Physical Chemistry Chemical Physics (2012), 14(13), 4447-4456.
Bailey, Ryan et al., Real-Time Multicolor DNA Detection with Chemoresponsive Diffraction Gratings and Nanoparticle Probes, J. Am Chem. Soc., 2003, 125, 13541-13547.
Baldwin et al., "Monoclonal antibodies in cancer treatment," *Lancet*, Mar. 15, 1986, 327(8481):603-605.
Banchereau et al., "Dendritic cells and the control of immunity," *Nature*, Mar. 19, 1998, 392(6673):245-252.
Barbas et al., "Assembly of combinatorial antibody libraries on phage surfaces: the gene III site," *Proc. Natl. Acad. Sci. U.S.A.*, Sep. 15, 1991, 88(18):7978-7982.
Barbas et al., "In vitro evolution of a neutralizing human antibody to human immunodeficiency virus type 1 to enhance affinity and broaden strain cross-reactivity," *Proc. Nat. Acad. Sci. U.S.A.*, Apr. 26, 1994, 94(9):3809-3813.
Barbas et al., "Semisynthetic combinatorial antibody libraries: a chemical solution to the diversity problem," *Proc. Natl. Acad. Sci. U.S.A.*, May 15, 1992, 89(10):4457-4461.
Bardotti, Angela et al., Size Determination of Bacterial Capsular Oligosaccharides Used to Prepare Conjugated Vaccines Against Neisseria Meningitidis Groups Y and W135, Vaccine 2005, 23, 1887-1899.
Barnes et al., "Methods for growth of cultured cells in serum-free medium," *Anal. Biochem.*, Mar. 1, 1980, 102(2):255-270.
Barouch, D. H. Challenges in the development of an HIV-I vaccine. Nature 455, 613-619, (2008).
Barry, C.S. et al., 'Naked' and Hydrated Confirmers of the Conserved Core Pentasaccharide of N-Linked Glycoproteins and Its Building Blocks, Journal of the American Chemical Society, 2013, vol. 135(45), p. 16895-16903.
Basak et al., In Vitro Elucidation of Substrate Specificity and Bioassay of Proprotein Convertase 4 Using Intramolecularly Quenched Fluorogenic Peptides, Biochem. J. Jun. 1, 2004, 380(pt 2): 505-514.
Baselga J, et al., "Phase II study of weekly intravenous recombinant humanized anti-p185HER2 monoclonal antibody in patients with HER2/neu-overexpressing metastatic breast cancer", *J Clin Oncol*. Mar. 1996;14(3):737-44.
Baskin, J.M.; Amacher, S. L.; Bertozzi, C.R." In vivo imaging of membraneassociated glycans in developing zebrafish." Science 2008, 320, 664-667.
Bass et al., "Hormone phage: an enrichment method for variant proteins with altered binding properties," *Proteins*, 1990, 8(4):309-314.
Bassell, G.J. et al., Single mRNAs Visualized by Ultrastructural in Situ Hybridization are Principally Localized at Actin Filament Intersections in Fibroblasts, J. Cell Biol., 126, 863-876 (1994.
Baz et al., Emergence of oseltamivir-resistant pandemic H1N1 virus during prophylaxis. N Engl J Med. Dec. 3, 2009;361(23):2296-7. doi: 10.1056/NEJMc0910060. Epub Nov. 11, 2009.
Beck A., "Biosimilar, biobetter and next generation therapeutic antibodies" MAbs. Mar.-Apr. 2011;3(2):107-10. Epub Mar. 1, 2011.
Beckman et al., Antibody constructs in cancer therapy: protein engineering strategies to improve exposure in solid tumors, cancer, 109(2): 170-179 (2007).
Bendayan, Moise, Possibilities of False Immunocytochemical Results Generated by the Use of Momoclonal Antibodies: The Example of the Anti-Proinsulin Antibody, J. Histochem. Cytochem, 43: 881-886, (1995).

Bennett, Clay et al., Chemoenzymatic Approaches to Glycoprotein Synthesis, Chem. Soc. Rev. 2007, 36:1227-1238.
Berg, Jan-Olof et al., Purification of Glycoside Hydrolases From Bacteroides Fragilis, Applied and Environmental Microbiology, vol. 40, No. 1, Jul. 1980, p. 40-47.
Berge, Steven et al. J. Pharmaceutical Sciences (1977) 66: 1-19.
Berra et al., "Correlation between ganglioside distribution and histological grading of human astrocytomas," *Int. J. Cancer*, Sep. 15, 1985, 36(3):363-366.
Best, M. D. "Click chemistry and bioorthogonal reactions: unprecedented selectivity in the labeling of biological molecules." Biochemistry 2009, 48, 6571-6584.
Bertozzi, CR et al., Glycans in Cancer and Inflammation—Potential for Therapeutics and Diagnostics, Nat Rev Drug Discovery, 2005, 4, 477-488.
Bigi et al., "Human sialidase NEU4 long and short are extrinsic proteins bound to outer mitochondrial membrane and the endoplasmic reticulum, respectively," *Glycobiology*, Feb. 2010, 20(2):148-157.
Birklé et al., "Role of tumor-associated gangliosides in cancer progression," *Biochimie*, Mar.-Apr. 2003, 85(3-4):455-463.
Blixt, O. et al. Printed covalent glycan array for ligand profiling of diverse glycan binding proteins. Proc. Natl. Acad. Sci. U.S. A. 101, 17033-17038, (2004.
Bobo et al., "Convection-enhanced delivery of macromolecules in the brain," *Proc. Nati. Acad. Sci. U.S.A.*, Mar. 15, 1994, 91(6) 2076-2080.
Boens, N. et al., "Fluorescent indicators based on BODIPY." Chem. Soc. Rev. 2012, 41, 1130-1172.
Boerner et al., "Production of antigen-specific human monoclonal antibodies from in vitro-primed human splenocytes," *J. Immunol.*, Jul. 1, 1991, 147(1):86-95.
Borg et al., "CD1d-lipid-antigen recognition by the semi-invariant NKT T-cell receptor," *Nature*, Jul. 5, 2007, 448(7149):44-49.
Bosmann et al., "Enzyme activity in invasive tumors of human breast and colon," *Proc. Natl. Acad. Sci. USA*, May 1974, 71(5):1833-1837.
Bost, Kenneth et al., Antibodies Against a Peptide Sequence Within the HIV Envelope Protein Crossreacts With Human Interleukin-2, Immunol. Invest., 17: 577-586 (1988).
Bothmann et al., "The periplasmic *Escherichia coli* peptidylprolyl cis,trans-isomerase FkpA. I. Increased functional expression of antibody fragments with and without cis-prolines," *J. Biol. Chem.*, Jun. 2, 2000, 275(22):17100-17105.
Boyer, David et al., Photothermal Imaging of Nanometer-Sized Metal Particles Among Scatterers, Science, 2002, 297, 1160-116 3.
Braun-Howland et al., Development of a Rapid Method for Detecting Bacterial Cell In Situ Using 16S rRNA-Targeted Probes, Biotechniques, 13, 928-931 (1992).
Brennan et al., "Preparation of bispecific antibodies by chemical recombination of monoclonal immunoglobulin $G_1$ fragments," *Science*, Jul. 5, 1985, 229(4708):81-83.
Bricard et al., "Enrichment of human CD4+ Vα24/Vβ11 invariant NKT cells in intrahepatic malignant tumors," *J. Immunol.*, Apr. 15, 2009, 182(2):5140-5151.
Brimble et al., "The cell surface glycosphingolipids SSEA-3 and SSEA-4 are not essential for human ESC pluripotency," *Stem Cells*, Jan. 2007, 25(1):54-62.
Brodeur et al., *Monoclonal Antibody Production Techniques and Applications, Chapter 4: Mouse-Human Myeloma Partners for the Production of Heterohybridomas*, Schook, ed., 1987, pp. 51-63, Marcel Dekker, Inc., New York.
Bruchez, Marcel et al. Semiconductor Nanocrystals as Fluorescent Biological Labels, Science 281:2013-2016, 1998.
Brüggemann et al., "Designer mice: the production of human antibody repertoires in transgenic animals," *Year in Immunol.*, 1993, 7:33-40.
Buchini et al., "Towards a new generation of specific *Trypanosoma cruzi* trans-sialidase inhibitors," *Angew. Chem. Int. Ed. Engl.*, 2008, 47(14):2700-2703.
Burton, D.R., Mascola, J. R. Antibody responses to envelope glycoproteins in HIV-I infection. Nature Immunol. 16, 571-6, (2015).

(56) References Cited

OTHER PUBLICATIONS

Calarese, D. A. et al. Antibody domain exchange is an immunological solution to carbohydrate cluster recognition. Science 300, 2065-2071, (2003).

Cao, Y. C. et al., Nanoparticles with Raman Spectroscopic Fingerprints for DNA and RNA Detection, Science, 2002, 289, 1757-60.

Capel PJ et al., "Heterogeneity of human IgG Fc receptors" *Immunomethods*. Feb. 1994;4(1):25-34.

Carlsson, Jan et al., Protein Thiolation and Reversible Protein-Protein Conjugation, Biochem J 173: 723-737 (1978).

Carter et al., "High level *Escherichia coli* expression and production of a bivalent humanized antibody fragment," *Nature Biotechnology*, Feb. 1992, 10(2):163-167.

Carter et al., "Humanization of an anti-p185$^{HER2}$ antibody for human cancer therapy," *Proc. Natl. Acad. Sci. U.S.A.*, May 15, 1992, 89(10):4285-4289.

Carter PJ. "Potent antibody therapeutics by design" *Nat Rev Immunol*. May 2006;6(5):343-357.

Carter, A rationale for using steroids in the treatment of severe cases of H5N1 avian influenza. J Med Microbiol. Jul. 2007;56(Pt 7):875-83.

Centers for Disease Control and Prevention (CDC), "Influenza activity—United States and worldwide, 2007-08 season" *MMWR*, Jun. 27, 2008, 57(25):692-697.

Cespedes et al., Mouse models in oncogenesis and cancer therapy, Clin Transl Oncl., 8(5): 318-329 (2006).

Chan, Warren et al., Quantum Dot Bioconjugates for Ultrasensitive Nonisotopic Detection, Science 281:2016-2018 (1998).

Chandler et al., Synthesis of the potent influenza neuraminidase inhibitor 5-guanidino Neu5Ac2en. X-Ray molecular structure of 5-acetaminido-4amino-2,6-anahydro-3,4,5-tryoxy-D-erythoro-L-giuco-nononic acid. J Chem Soc Perkin Trans 1. 1995; 1173-1180.

Chang et al., "Expression of Globo H and SSEA3 in breast cancer stem cells and the involvement of fucosyl transferases 1 and 2 in Globo H synthesis," *Proc. Natl. Acad. Sci. U.S.A.*, Aug. 19, 2008, 105(33):11667-11672.

Chang, S. H. et al. Glycan array on aluminum oxide-coated glass slides through phosphonate chemistry. J. Am. Chem. Soc. 132, 13371-13380, (2010).

Chang et al., "Potent immune-modulating and anticancer effects of NKT cell stimulatory glycolipids," *Proc. Natl. Acad. Sci. USA*. Jun. 19, 2007, 104(25):10299-10304.

Chao, W.; Fang, X.; Nisaraporn, S.; Jian, S.; Qian, W. "Tuning the optical properties of BODIPY dye through Cu(I) catalyzed azide-alkyne cycloaddition (CuAAC) reaction." Sci. China Chemistry 2012, 55, 125-130.

Chari, Ravi et al., Immunoconjuates Containing Novel Maytansinoids: Promising Anticancer Drugs Cancer Research 52: 127-131 (1992).

Chauhan, D. P.; Saha, T.; Lahiri, M.; Talukdar, P. "BODIPY based 'click on' fluorogenic dyes: application in live cell imaging." Tetrahedron Lett. 2014, 55, 244-247.

Chen et al., "Chaperone activity of DsbC," *J. Bio. Chem.*, Jul. 9. 1999, 274(28):19601-19605.

Chen et al., "Selection and analysis of an optimized anti-VEGF antibody: crystal structure of an affinity-matured Fab in complex with antigen," *J. Mol. Biol.*, Nov. 5, 1999, 293(4):865-881.

Chen et al., "Selective killing of transformed cells by cyclin/cyclin-dependent kinase 2 antagonists," *Proc. Natl. Acad. Sci. U.S.A.*, Apr. 13, 1999, 96(8):4325-4329.

Cheng, Peter et al., Oseltamivir- and Amandtadine-resistant Influenza Viruses A (H1N1), Emerg. Infect. Dis., Jun. 2009, 15(6): 966-968.

Cheung et al., Stage-specific embryonic antigen-3 (SSEA-3) and beta3GalT5 are cancer specific and significant markers for breast cancer stem cells, PNAS, Jan. 26, 2016, vol. 113, No. 4, pp. 960-965.

Chiang et al., Ethyl caffeate suppresses NF-kappaB activation and its downstream inflammatory mediators, iNOS, COX-2, and PGE2 in vitro or in mouse skin. Br J Pharmacol. Oct. 2005; 146(3):352-63.

Chiari, M. et al., Advanced Polymers for Molecular Recognition and Sensing at the Interface. J Chromatography B, Apr. 15, 2008, 866(1-2):89-103.

Childs et al., Receptor-Binding Specificity of Pandemic Influenza A (H1N1) 2009 Virus Determined by Carbohydrate Microarray. Nat. Biotechnol. 2009, 27(9): 797-799.

Cho, Se-Heon et al., Sialyl-Tn Antigen Expression Occurs Early During Human Mammary Carcinogenesis and is Associated with High Nuclear Grade and Aneuploidy, Cancer Res. 54, 6302-6305, 1994.

Chong et al., Influenza Virus Sialidase: Effect of Calcium on Steady-State Kinetic Parameters, Biochim. Biophys. Acta, Mar. 8, 1991, 1077(1): 65-71.

Chothia et al., "Canonical structures for the hypervariable regions of immunoglobulins," *J. Mol. Biol.*, Aug. 20, 1987, 196(4):901-917.

Chothia et al., "Domain association in immunoglobulin molecules. The packing of variable domains," *J. Mol. Biol.*, Dec. 5, 1985, 186(3):651-663.

Chu, Kuo-Chinget al., Efficient and Stereoselective Synthesis of [alpha](2->9) Oligosialic Acids: From Monomers to Dodecamers, Angewandte Chemie International Edition, vol. 50, No. 40, Sep. 2011, 9391-9395.

Clackson et al., "Making antibody fragments using phage display libraries," *Nature*, Aug. 15, 1991, 352(6336):624-628.

Clark EA et al., "Structure, function, and genetics of human B cell-associated surface molecules" *Adv Cancer Res*. 1989;52:81-149.

Clynes R, et al., "Fc receptors are required in passive and active immunity to melanoma" *Proc Natl Acad Sci U S A*. Jan. 20, 1998;95(2):652-6.

Codelli, J. A. et al., Second-Generation Difluorinated Cycloctynes for Copper-Free Click Chemistry, J. Am. Chem. Soc. 2008, 130, 11486-11493.

Cohen-Daniel et al., Emergance of Oseltamivir-Resistant Influenza A/H3N2 Virus with Altered Hemagglutination Pattern in Hematopoietic Stem Cell Transplant Recipient, J Clin Virol., Feb. 2009, 44(2):138-140.

Coligan et al., Current Protocols in Immunology, sections 2.5.1-2. 6.7, 1991.

Collins et al., Crystal Structures of Oseltamivir-Resistant Influenza Virus Neuraminidase Mutants, Nature, Jun. 26, 2008, 453(7199):1258-1261.

Connor, Robert et al., Receptor Specifcity in Human, Avian, and Equine H2 and H3 Influenza Virus Isolates, Virology, 205: 17, 1994.

Cox et al., New Options for the Prevention of Influenza, N. Engl. J. Med. Oct. 28, 1999, 341(18): 1387-1388.

Cragg, M.S. et al., Complement-Mediated Lysis by Anti-CD20 mAb Correlates with Segregation into Lipid Rafts, Blood 101 (2003) 1045-1052.

Cragg, M.S. et al., Antibody Specificity Controls in Vivo Effector Mechanism of Anti-CD20 Reagents, Blood, 103 (2004) 2738-2743.

Craigo, J. K., Montelaro, R. C. Lessons in AIDS vaccine development learned from studies of equine infectious, anemia virus infection and immunity. Viruses 5, 2963-76, (2013.

Crispin et al., "Carbohydrate and domain architecture of an immature antibody glycoform exhibiting enhanced effector functions," J. Mol. Biol., Apr. 17, 2009, 387(5):1061-1066.

Cunningham et al., "High-resolution epitope mapping of hGH-receptor interactions by alanine-scanning mutagenesis," *Science*, Jun. 2, 1989, 244(4908):1081-1085.

Cyranoski, Threat of Pandemic Brings Flu Drug Back to Life, Nat. Med. Sep. 2005, 11(9): 909.

Daëron, "Fc receptor biology," *Annu. Rev. Immunol.*, 1997, 15:203-234.

Davies, JW et al., Streamlining Lead Discovery by Aligning in Silico and High-Throughput Screening, Curr Opin Chem Biol. Aug. 2006; 10(4):343-51.

Davodeau et al., "Close phenotypic and functional similarities between human and murine αβ T cells expressing invariant TCR alpha-chains," *J. Immunol.*, Jun. 15, 1997, 158(12):5603-5611.

De Almeida et al., "Thiacycloalkynes for copper-free click chemistry," *Angew. Chem. Int. Ed. Engl.*, Mar. 5, 2012, 51(10):2443-2447.

(56) References Cited

OTHER PUBLICATIONS

Debets, M. F. et al., Bioconjugation with Strained Alkenes and Alkynes, Acc. Chem. Res. 2011, 44, 805-815.
De Haas et al., "Fcγ receptors of phagocytes," J. Lab. Clin. Med., Oct. 1995, 126(4):330-341.
Dejong et al., Fatal outcome of human influenza A (H5N1) is associated with high viral load and hypercytokinemia. Nat Med Oct. 2006;12(10):1203-7. Epub Sep. 10, 2006.
Delente, Jacqubs, Glycosylation Revisited, Trends in Biotechnology 3, letters to editor, No. 9 (1985).
Dellabona et al., "An invariant Vα24-JαQ/Vβ11 T cell receptor is expressed in all individuals by clonally expanded CD4$^-$8$^-$ T cells," J. Exp. Med., Sep. 1, 1994, 180(3):1171-1176.
Demchenko, A.V., Ed., Hanbook of Chemical Glycosylation: Advances in Stereoselectivity and Therapeutic Relevance (2008) WILEY-VCH. Chapter 1. General Aspects of the Glycosidic Bond Formation, in 28 pages.
Dennis, Carina, Cancer: Off by a whisker, Nature 442: 739-741 (2006).
De Paz, J. L., Horlacher, T. & Seeberger, P.H. Oligosaccharide microarrays to map interactions of carbohydrates in biological systems. Methods Enzymol. 415, 269-292, (2006).
Dhodapkar et al., "α-Galactosyl ceramide-loaded dendritic cells for expansion of natural killer T cells" CAPLUS 145:354715 (2006).
Dhodapkar et al., "A reversible defect in natural killer T cell function characterizes the progression of premalignant to malignant multiple myeloma," J. Exp. Med., Jun. 16, 2003, 197(12):1667-1676.
Dicker, Martina et al., Using Glyco-Engineering to Produce Therapeutic Proteins, Expert Opinion on Biological Therapy, vol. 15, Jan. 1, 2015, pp. 1501-1516.
Dohi, Taeko et al., Fucosyltransferase-Producing Sialyl Lea and Sialyl Lex Carbohydrate Antigen in Benign and Malignant Gastrointestinal Mucosa, Cancer 73, 1552, 1994.
Dohi, H. et al., Stereoselective Glycal Fluorophosphorlation: Synthesis of ADP-2-Fluoroheptose, an Inhibitor of the LPS Biosynthesis, Chem-Eur J 2008, 14, 9530-9539.
Dommerholt, Jan, Readily Accessible Bicyclononynes for Bioorthogonal Labeling and Three-Dimensional Imaging of Living Cells, Angew. Chem. Int. Ed. 2010, 49, 9422-9425.
Doores KJ, et al. A nonself sugar mimic of the HIV glycan shield shows enhanced antigenicity. Proc. Natl. Acad Sci. US.A. 107(40), 17107-17112, (2010).
Doores, K. J. & Burton, D.R. Variable Loop Glycan Dependency of the Broad and Potent HIV-I-Neutralizing Antibodies PG9 and PG16. J. Virol. 84, 10510-10521, (2010).
Doores, K. J. et al. Envelope glycans of immunodeficiency virions are almost entirely oligomannose antigens. Proc. Natl. Acad. Sci. U. S. A 107, 13800-13805, (2010).
Doronina, Svetlana et al., Development of Potent Monoclonal Antibody Auristatin Conjugates for Cancer Therapy, Nat Biotechnol 21(7): 778-784 (2003).
Dougan, Michael et al., Immune Therapy for Cancer, Annual Review of Immunology, 2009, 27, pp. 83-117.
Drugs of the future 25(7): 686 (2000).
Dubertret. Benoit et al., In Vivo Imaging of Quantum Dots Encapsulated in Phospholipid Micelles, Science 298:759-1762, 2002.
Duncan, AR; Winter, G, The binding Site for C1q on IgG, Nature 322:738-40 (1988).
Dunn et al., Zanamivir: A Review of its Use in Influenza, Drugs, Oct. 1999, 58(4):761-784.
Durrant et al., "Immunology in the clinic review series; focus on cancer: glycolipids as targets for tumor immunotherapy," Clin. Exp. Immunol., Feb. 2012, 167(2):206-215.
Eberl et al., "Selective bystander proliferation of memory CD4$^+$ and CD8$^+$ T cells upon NK T or T cell activation," J. Immunol., Oct. 15, 2000, 165(8):4305-4311.
Eberl et al., "Selective induction of NK cell proliferation and cytotoxicity by activated NKT cells," Eur. J. Immunol., Apr. 2000, 30(4):985-992.

Eggink, D. et al. Lack of complex N-glycans on HIV-I envelope glycoproteins preserves protein conformation and entry function. Virology 401, 236-247, (2010).
Eisen, Michael et al., "Binding of the Influenza A Virus to Cell-Surface Receptors: Structures of Five Hemagglutinin-Sialyloligosaccharide Complexes Determined by X-Ray Crystallography, Virology, 232:19, 1997.
Ellis J., et al., Evaluation of Four Real-Time PCR Assays for Detection of Influenza A9H1N1)v Viruses, Euro Surveill. 2009; 14(22), p. 1-3.
Embleton et al., "In-cell PCR from mRNA: amplifying and linking the rearranged immunoglobulin heavy and light chain V-genes within single cells," Nuel. Acids Res., Aug. 11, 1992, 20(15):3831-3837.
Engels et al., "Gene synthesis [new synthetic methods (77)]," Angew. Chem. Int. Ed. Engl., Jun. 1989, 28(6):716-734.
European Search Report issued in connection with corresponding European Patent Application No. 15181446.4, dated Dec. 7, 2015, 10 pages.
Evans, Michael et al., "Mechanism-based profiling of enzyme families," Chem. Rev., Aug. 2006, 106(8):3279-3301.
Evans, "The rise of azide-alkyne 1,3-dipolar 'click' cycloaddition and its application to polymer science and surface modification," Australian J. Chem., Jun. 2007, 60(6):384-395.
Extended European Search Report dated Jan. 5, 2016 in European Patent Application No. 13830785.5, in 10 pages.
Extended European Search Report, App. No. 15799789.1, dated Nov. 28, 2017, 10 Pages.
Extended European Search Report, App. No. 158001917, dated Nov. 28, 2017, 12 Pages.
Extended European Search Report, App. No. 15799981.4, dated Nov. 29, 2017, 9 Pages.
Falkowska, E. et al. Broadly neutralizing HIV antibodies define a glycan-dependent epitope on the prefusion conformation of gp41 on cleaved envelope trimers. Immunity 40, 657-68, 2014.
Fan, Shu-Quan et al., Remarkable Transglycosylation Activity of Glycosynthase Mutants of Endo-D, an Endo-β-N-acetylglucosaminidase from Streptococcus pneumoniae, JBC vol. 287, No. 14, pp. 11272-11281, Mar. 30, 2012.
Fazio, F. et al., Synthesis of sugar arrays in microtiter plate. J. Am. Chem. Soc. 124, 14397-14402, (2002).
FDA Guidance for Industry for Container Closure Systems for Packaging Human Drugs and Biologics, May 1999.
Fedson, Confronting the next influenza pandemic with anti-inflammatory and immunomodulatory agents: why they are needed and how they might work. Influenza Other Respi Virusts. Jul. 2009;3(4):129-42.
Feizi, Ten, Carbohydrate Differentiation Antigens: Probable Ligands for Cell Adhesion Molecules,Trends Biochem. Sci. 16, 84-86.
Fellouse et al., "Synthetic antibodies from a four-amino-acid code: a dominant role for tyrosine in antigen recognition," Proc. Natl. Acad. Sci. U.S.A., Aug. 24, 2004, 101(34):12467-12472.
Fernandez-Tejada, Alberto et al., Designing synthetic vaccines for HIV. Expert Rev. Vaccines 14, 815-31, 2015.
Fernandez-Megia et al., A Click Approach to Unprotected Glycodendrimers. Macromolecules 2006, vol. 39, pp. 2113-2120.
Fessner et al., Enzymes in Organic Synthesis, Short Enzymatic Synthesis of L-Fucose Analogs. Eur. J. Org. Chem 2000. p. 125-132.
Fiehn, Oliver, Combining Genomics, Metabolome Analysis, and Biochemical Modelling to Understand Metabolic Networks, Comparative and Functional Genomics 2:155-168,2001.
Fishwild et al., "High-avidity human IgGκ monoclonal antibodies from a novel strain of minilocus transgenic mice," Nature Biotechnol., Jul. 1996, 14(7):845-851.
Fraker, PJ et al., Protein and Cell Membrane Iodinations with a Sparingly Soluble Chloroamide, 1,3,4,6-tetrachloro-3a,6a-diphrenylglycoluril, Biochem. Biophys. Res. Commun. 80: 49-57 (1978).
Frank, Natasha et al., The Therapeutic Promise of the Cancer Stem Cell Concept, Journal of Clinical Investigation, 120(1) 41-50, Jan. 2010.

(56) References Cited

OTHER PUBLICATIONS

Fredman et al., "Expression of gangliosides GD3 and 3'-isoLM1 in autopsy brains from patients with malignant tumors," *J. Neurochem.*, Jan. 1993, 60(1):99-105.
Fredman et al., "Potential ganglioside antigens associated with human gliomas," *Neurol. Res.*, Jun. 1986, 8(2):123-126.
Fredman et al., "Sialyllactotetraosylceramide, a ganglioside marker for human malignant gliomas," *J. Neurochem.*, Mar. 1988, 50(3):912-919.
Friscourt, F. et al., A Fluorogenic Probe for the Catalyst-Free Detection of Azide-Tagged Molecules, J. Am. Chem. Soc. 2012, 134, 18809-18815.
Friscourt et al., "Polar Dibenzocyclooctynes for Selective Labeling of Extracellular Glycoconjugates of Living Cells," *J. Am. Chem. Soc.*, Mar. 21, 2012, 134(11):5381-5389.
Fujimore, Kenji et al., A Modeling Analysis of Monoclonal Antibody Percolation Through Tumors: A Binding-Site Barrier, J Nuc Med. 31: 1191-1198 (1990).
Fujio, M. et al. "Structure-Based Discovery of Glycolipids for CD1d-Mediated NKT Cell Activation: Turning the Adjuvant versus Immunosuppression Activity." CAPLUS 145:240945 (2006).
Fujio, M. et al. "Structure-Based Discovery of Glycolipids for CD1d-Mediated NKY Cell Activation: Turning the Adjuvant versus Immunosuppression Activity." J. Am. Chem. Soc. (2006), vol. 128, pp. 9022-9023.
Fujita M et al., "A novel disaccharide substrate having 1,2-oxazoline moiety for detection of transglycosylating activity of endoglycosidases" *Biochim Biophys Acta.* Sep. 3, 2001;1528(1):9-14.
Fukui, S et al., Oligosaccharide microarrays for high-throughput detection and specificity assignments of carbohydrate-protein interactions. Nat. Biotechnol. 20, 1011-1017, (2002).
Gabius, HJ. Tumor Lectinology: at the intersection of carbohydrate chemistry, biochemistry, cell biology and oncology. Angew. Chem. Int. Ed. Engl. 27, 1267-1276.
Galfrè et al., "Preparation of monoclonal antibodies: strategies and procedures," *Methods Enzymol.*, 1981, 73(Pt B):3-46.
Gamblin, SJ et al., The Structure and Receptor Binding Properties of the 1918 Influenza Hemagglutinin, Science, 303:1838, 2004.
Garces, F. et al. Structural evolution of glycan recognition by a family of potent HIV antibodies. Cell 159, 69-79, (2014).
Gaschen, B. et al. AIDS—Diversity Considerations in HIV-I vaccine selection. Science 296, 2354-2360, (2002).
Gazzano-Santoro et al., "A non-radioactive complement-dependent cytotoxicity assay for anti-CD20 nonclonal antibody," *J. Immunol. Methods*, Mar. 28, 1997, 202(2):163-171.
Geiler et al., Comparison of pro-inflammatory cytokine expression and cellular signal transduction in human macrophages infected with different influenza A viruses. Med Microbiol Immunol. Feb. 2011;200(1):53-60.
GenBank accession No. AAA24922.1, "endoglycosidase F [Elizabethkingia meningoseptica]," May 27, 2008.
GenBank accession No. AAA24923.1, "endoglycosidase, partial [Elizabethkingia meningoseptica]," Jun. 8, 1993.
GenBank accession No. AAA24924.1.1, "endoglycosidase, partial [Elizabethkingia meningoseptica]," Jun. 7, 1993.
GenBank accession No. AAA26738.1, "endo-beta-N-acetylglucosaminidase H [Streptomyces plicatus]," Apr. 26, 1993.
GenBank accession No. J05449.1, "F.meningosepticum peptide-N-4-(N-acetyl-beta-D-glucosaminyl) asparagine amidase (PNGase F) mRNA, complete cds," Jan. 16, 1996.
GenBank accession No. YP_212855.1, "Putative exported alpha-L-fucosidase protein [Bacteroides fragilis NCTC 9343]," Mar. 2, 2014.
GenBank accession No. WP_0080769537.1, published May 10, 2013.
GenBank accession No. WP_008767711.1, published May 10, 2013.
Geoghegan, Kieran et al., Site-Directed Conjugation of Nonpeptide Groups to Peptides and Proteins Via Periodate Oxidation of a 2-amino Alcohol. Applications to Modification at N-Terminal Serine, Bioconjugate chem. 3:138-146 (1992).
Gerson et al., "ESR. Spectra and Structures of Radical Anions in the Dibenzo[a,e]cyclooxtene Series," *Helvetica Chinica Acta*, Jan. 1, 1976, 59(6): 2038-2048.
Giaccone, Giuseppe et al., "A phase I study of the natural killer T-cell ligand α-galactosylceramide (KRN7000) in patients with solid tumors," *Clin. Cancer Res.*, Dec. 2002, 8(12):3702-3709.
Gill et al., "Direct brain infusion of glial cell line-derived neurotrophic factor in Parkinson disease," *Nature Med.*, May 2003, 9(5):589-595 and Addendum from Apr. 2006, 12(4):479.
Go, E. P. et al. Characterization of glycosylation profiles of HIV-I transmitted/founder envelopes by mass spectrometry. J. Virol. 85, 8270-8284, (2011).
Go, E. P. et al. Comparative Analysis of the Glycosylation Profiles of Membrane-Anchored HIV-I Envelope Glycoprotein Trimers and Soluble gp140. J. Virol. 89, 8245-57, (2015).
Godefroy, S. et al., Effect of Skin Barrier Disruption on Immune Responses to Topically Applied Cross-Reacting Material, CRM197 of Diphtheria Toxin, Infect. Immun 2005, 73, 4803.
Goding, *Monoclonal Antibodies: Principles and Practice* $2^{nd}$ ed., Chapter 3: Production of Monoclonal Antibodies, 1986, pp. 59-103, Academic Press, London.
Goldenthal et al., "Safety Evaluation of Vaccine Adjuvants: National Cooperative Vaccine Development Working Group," *AIDS Res. Hum. Retroviruses*, 1993, 9(Supp.1):S47-S51.
Golkowski et al., "Strategy for catch and release of azide-tagged biomolecules utilizing a photolabile strained alkyne construct," *Organic and Biomolecular Chemistry*, Jan. 1, 2012, 10(23):4496.
Goochee CF et al., "The oligosaccharides of glycoproteins: bioprocess factors affecting oligosaccharide structure and their effect on glycoprotein properties", *Biotechnology* (N Y). Dec. 1991;9(12):1347-55.
Gordon et al., "Reactivity of biarylazacyclooctynones in copper-free click chemistry," *J. Am. Chem. Soc.*, Jun. 6, 2012, 134(22): 9199-9208.
Gottschling et al., "Stage-specific embryonic antigen-4 is expressed in basaloid lung cancer and associated with poor prognosis," *Eur. Respir. J.*, Mar. 2013, 41(3):656-663.
Govorkova et al, Combination chemotherapy for influenza. Viruses. Aug. 2010;2(8):1510-29.
Graham et al., "Characteristics of a human cell line transformed by DNA from human adenovirus type 5," *J. Gen. Virol.*, Jul. 1977, 36(1):59-72.
Graham, Duncan et al., Surface-Enhanced Resonance Raman Scattering as a Novel Method of DNA Discrimination, Angew. Chem., 2000, 112(6), 1103-1105.
Gram et al., "In vitro selection and affinity maturation of antibodies from a naive combinatorial immunoglobulin library," *Proc. Natl. Acad. Sci. U.S.A.*, Apr. 15, 1992, 89(8):3576-3580.
Grandjean, C. et al., On the Preparation of Carbohydrate-Protein Conjugates Using the Traceless Staudinger Ligation, J Org Chem 2005, 70, 7123-7132.
Green, "Targeting targeted therapy," *N. Engl. J. Med.*, May 20, 2004, 350(21):2191-2193.
Greenbaum et al., "Chemical approaches for functionally probing the proteome," *Mol. Cell. Proteomics*, 2002, 1:60-68.
Griffiths et al., "Human anti-self antibodies with high specificity from phage display libraries," *EMBO J.*, Feb. 1993, 12(2):725-734.
Gruber et al., "Efficient tumor cell lysis mediated by a bispecific single chain antibody expressed in *Escherichia coli,*" *J. Immunol.*, Jun. 1, 1994, 152(11):5368-5374.
Grubisha, D. S. et al., Femtomolar Detection of Prostate-Specific Antigen: An Immunoassay Based on Surface-Enhanced Raman Scattering and Immunogold labels, Anal. Chem. (2003), 75, 5936-5943.
Gulati et al., Deletions of Neuraminidase and Resistance to Oseltamivir May Be a Consequence of Restricted Receptor Specificity in Recent H3N2 Influenza Viruses. Virol. J. 2009, 6(22)L 1-15.
Gulland, Fire Cases of Spread of Oseltamivir Resistant Swine Flu Between Patients are Reported in Wales, BMJ, Nov. 23, 2009:339:b4975.
Guss et al., "Structure of the IgG-binding regions of streptococcal protein G," *EMBO J.*, Jul. 1986, 5(7):1567-1575.

(56) References Cited

OTHER PUBLICATIONS

Guyer et al., "Immunoglobulin binding by mouse intestinal epithelial cell receptors," *J. Immunol.*, Aug. 1976, 117(2):587-593.
Ha, Ya et al., X-Ray Structures of H5 Avian and H9 Swine Influenza Virus Hemagglutinins Bound to Avian and Human Receptor Analogs, Proc Natl Acad Sci USA, 98:11181-11186, 2001.
Ha, Ya et al., X-Ray Structure of the Hemagglutinin of a Potential H3 Avian Progenitor of the 1968 Hong Kong Pandemic Influenza Virus, Virology, 309:209-218, 2003.
Hajishengallis, "Mucosal immunization with a bacterial protein antigen genetically coupled to cholera toxin A2/B subunits," *J. Immunol.*, May 1, 1995, 154(9):4322-4332.
Hakomori et al., "Glycosphingolipid antigens and cancer therapy," *Chem. Biol.*, Feb. 1997, 4(2):97-104.
Hakomori, "Glycosylation defining cancer malignancy: new wine in an old bottle," *Proc. Natl. Acad. Sci. U.S.A.*, Aug. 6, 2002, 99(16):10231-10233.
Ham, Richard et al., Media and Growth Requirements, Meth. Enz 58, 44 (1979).
Hammerling et al., in: Monoclonal Antibodies and T-Cell Hybridomas 563-587, 1981.
Han, Junyan et al., 3- and 5-Functionalized BODIPYs via the Liebeskind-Srogl Reaction, Organic & Biomolecular Chemistry (2009), 7(1), 34-36.
Hanski, Christoph et al., Altered Glycosylation of the MUC-1 Protein Core Contributes to the Colon Carcinoma-Associated Increase of Mucin-Bound Sialyl-Lewis Expression, Cancer Res. 53, 4082-4088 (1993).
Hanski, C. et al., Characterization of the Major Sialyl-Lex-Poristive Mucins Present in Colon, Colon Carcinoma, and Sera of Patients with Colorectal Cancer, Cancer Res. 55, 928-933 (1995).
Hara et al., "Overproduction of penicillin-binding protein 7 suppresses thermosensitive growth defect at low osmolarity due to an spr mutation of *Escherichia coli*," *Microbial Drug Resistance*, Spring 1996, 2(1):63-72.
Harris, "Production of humanized monoclonal antibodies for in vivo imaging and therapy," *Biochem. Soc. Transactions*, Nov. 1995, 23(4):1035-1038.
Hasegawa, Akira, et al., Synthesis of Sialyl Lewis X Ganglioside Analogues Containing Modified L-Fucose Residues, Carbohydr. Res. 1995, 274, 165-181.
Hata, K. et al., Limited Inhibitory Effects of Oseltamivir and Zanamivir on Human Sialidases, Antimicrobial Agents and Chemotherapy, vol. 52, No. 10, Oct. 2008, in 8 pages.
Hawkins et al., "Selection of phage antibodies by binding affinity Mimicking affinity maturation," *J. Mol. Biol.*, 1992, 226(3):889-896.
Healthy Living, "10 Simple and Natural Ways to Boost Your Immune System," Published Jan. 31, 2014, downloaded from online, http://www.everydayhealth.com/columns/white-seeber-grogan-the-remedy-chicks/ten-simple-natural-ways-to-b . . . on Aug. 19, 2016.
Henglein, A. et al., Absorption Spectrum and Some Chemical Reactions of Colloidal Platinum in Aqueous Solution, J. Phys. Chem., 99, 14129 (1995).
Herner, A et al., A new family of bioorthogonally applicable fluorogenic labelst, Org. Biomol. Chem. 2013, 11, 3297-3306.
Hey, Thomas et al., Artificial, non-antibody binding proteins for pharmaceutical and industrial application, Trends in Biotechnology 23(10) 514-522 (2005).
Heyman, "Complement and Fc-receptors in regulation of the antibody response," *Immunol. Lett.*, Dec. 1996, 54(2-3):195-199.
Hinman et al., "Preparation and characterization of monoclonal antibody conjugates of the calicheamicins: a novel and potent family of antitumor antibiotics," *Cancer Res.*, Jul. 15, 1993, 53(14):3336-3342.
Hirabayashi, J. et al., Oligosaccharide Microarrays for Glycomics, Trends in Biotechnology 21 (4): 141-143, 2003.
Hogrefe et al., "A bacteriophage lambda vector for the cloning and expression of immunoglobulin Fab fragments on the surface of filamentous phage," *Gene*, Jun. 15, 1993, 128(1):119-126.
Holliger et al., "'Diabodies': small bivalent and bispecific antibody fragments," *Proc. Natl. Acad. Sci. U.S.A.*, Jul. 15, 1993, 90(14):6444-6448.
Holmskov, Uffe et al., Collectins: Collagenous C-Type Lectins of the Innate Immune Defense System, 1994, Immunol. Today, 15: 67.
Honda et al., Synthesis and anti-influenza virus activity of 7-0-alkylated derivatives related to zanamivir. Bioorg Med Chem Lett. Aug. 5, 2002;12(15):1925-8.
Honegger et al., "Yet another numbering scheme for immunoglobulin variable domains: an automatic modeling and analysis tool," *J. Mol. Biol.*, Jun. 8, 2001, 309:657-670.
Hoogenboom et al., "By-passing immunisation: Human antibodies from synthetic repertoires of germline $V_H$ gene segments rearranged in vitro," *J. Mol. Biol.*, Sep. 20, 1992, 227(2):381-388.
Hoogenboom et al., "Multi-subunit proteins on the surface of filamentous phage: methodologies for displaying antibody (Fab) heavy and light chains," *Nucl. Acids Res.*, Aug. 11, 1991 19(15):4133-4137.
Hotha, Srinivas et al., "Click Chemistry" Inspired Synthesis of Pseudo-Oligosaccharides and Amino Acid Glycoconjugates, J Org Chem 2006, 71, 364-367.
Horiya, S. et al., Recent strategies targeting HIV glycans in vaccine design. Nat. Chem. Biol. 10, 990-999, (2014).
Horn et al., Investigation into an Efficient Synthesis of 2,3-dehydro-N-acetyl Neuraminic Acid Leads to Three Decarboxylated Sialic Acid Dimers, Carbohdr. Res., Apr. 7, 2008, 343(5):936-940.
Howard et al., "Biological properties of interleukin 10," *Immunol. Today*, Jun. 1992, 13(6):198-200.
Hsu et al., "Alkynyl sugar analogs for the labeling and visualization of glycoconjugates in cells," *Proc. Natl. Acad. Sci. USA*, Feb. 20, 2007, 104(8), 2614-2619.
Hsu, Nien-Yeen et al., Desorption Ionization of Biomolecules on Metals, Anal. Chem., 80, 5203-5210, 2008.
Huang, et al., "Carbohydrate-based vaccines with a glycolipid adjuvant for breast cancer," *Proc. Natl. Acad. Sci. U.S.A.*, Feb. 12, 2013, 110(7):2517-2522.
Huang, Lijun et al., Iterative One-Pot Syntheses of Chitotetroses, Carbohydr. Res. 2006, 341, 1669-1679.
Huang, Wei et al., Chemoenzymatic Glycoengineering of Intact lgG Antibodies for Gain of Functions, Journal American Chemical Socirty, vol. 134, No. 9, Jul. 25, 2012, pp. 12308-12318.
Huang et al., Recombinant immunotherpaeutics: current state and perspectives regarding the feasibility and market, Appl Microbiol Biotechnol, 87: 401-410. 2010.
Hung et al., "Investigation of SSEA-4 binding protein in breast cancer cells," *J. Am. Chem. Soc.*, Apr. 24, 2013, 135(16):5934-5937.
Hurle et al., "Protein engineering techniques for antibody humanization," *Curr. Opin. Biotechnol.*, Aug. 1994, 5(4):428-433.
Immunogenicity, Wikipedia p. 1-3. Downloaded on Aug. 16, 2016 from https://en.wikipedia.org/wiki/Immunigenicity. (2016).
Inouye et al., "Single-step purification of $F(ab')_{2u}$ fragments of mouse monoclonal antibodies (immunoglobulins M) by hydrophobic interaction high-performance liquid chromatography using TSKgel Ether-5PW," *J. Biochem. Biophys. Methods*, Feb. 1993, 26(1):27-39.
International Search Report and Written Opinion issued for International application No. PCT/US2015/011748, dated Aug. 21, 2015, 17 pages.
International Search Report and Written Opinion issued for International application No. PCT/US2015/032737, dated Oct. 1, 2015, 13 pages.
International Search Report and Written Opinion issued for International application No. PCT/US2015/032738, dated Oct. 20, 2015, 15 pages.
International Search Report and Written Opinion issued for International application No. PCT/US2015/032740, dated Oct. 26, 2015, 13 pages.
International Search Report and Written Opinion issued for International application No. PCT/US2015/032744, dated Oct. 2, 2015, 12 pages.

(56) References Cited

OTHER PUBLICATIONS

International Search Report and Written Opinion issued for International application No. PCT/US2015/032745, dated Oct. 8, 2015, 13 pages.
International Search Report dated Jan. 13, 2012, from corresponding International Patent Application No. PCT/US2011/035982, 17 pages.
International Search Report dated Nov. 13, 2014, from corresponding International Patent Application No. PCT/US2014/054617, 10 pages.
International Search Report issued for International application No. PCT/US2015/049014, dated Dec. 14, 2015, 3 pages.
International Search Report and Written Opinion in International Application No. PCT/US16/15858, dated Jun. 27, 2016, in 8 pages.
International Search Report issued for International application No. PCT/US15/22977, dated Jun. 22, 2015, 3 pages.
International Search Report issued for International application No. PCT/US15/40199, dated Mar. 2, 2016, 6 pages.
International Search Report issued for International application No. PCT/US2009/050754, dated Feb. 24, 2010, 10 pages.
International Search Report and Written Opinion in International Application No. PCT/US2017/021454, dated Jul. 31, 2017, 8 pages.
International Search Report and Written Opinion in International Application No. PCT/US2017/048074, dated Dec. 26, 2017, 17 pages.
Isshiki et al., Cloning, Expression, and Characterization of a Novel UDP-galactose:b-N-Acetylglucosamine b1,3-Galactosyltransferase (b3Gal-T5) Responsible for Synthesis of Type 1 Chain in Colorectal and Pancreatic Epithelia and Tumor Cells Derived Therefrom, The Journal of Biological Chemistry, Apr. 30, 1999, vol. 274, No. 18, pp. 12499-12507.
Ito, Akihiro et al., A Novel Ganglioside Isolated From Renal Cell Carcinoma, Biol Chem 2001, 276, 16695.
Jackson et al., "In vitro antibody maturation: Improvement of a high affinity, neutralizing antibody against IL-1β," *J. Immunol.*, Apr. 1, 1995, 154(7):3310-3319.
Jacobs et al., "Metabolic labeling of glycoproteins with chemical tags through unnatural sialic acid biosynthesis," *Methods Enzymol.*, 2000, 327:260-275.
Jakobovits et al., "Analysis of homozygous mutant chimeric mice: deletion of the immunoglobulin heavy-chain joining region blocks B-cell development and antibody production," *Proc. Natl. Acad. Sci. U.S.A.*, Mar. 15, 1993, 90(6):2551-2555.
Jakobovits et al., "Germ-line transmission and expression of a human-derived yeast artificial chromosome," *Nature*, Mar. 18, 1993, 362(6417):255-258.
Japanese Office Action dated Apr. 21, 2015, from Related Japanese Patent Application No. 2013-510261, 6 Pages.
Jayasena, Sumedha, Aptamers: An Emerging Class of Molecules That Rival Antibodies in Diagnostics, Clin. Chem. (1999), 45, 1628-1650.
Jenkins N, Curling EM., "Glycosylation of recombinant proteins: problems and prospects", *Enzyme Microb Technol*. May 1994;16(5):354-64.
Jewett, J.C.; Bertozzi, C.R., Cu-Free Click Cycloaddition Reactions in Chemical Biology, Chem. Soc. Rev. 2010, 39, 1272-1279.
Jewett, J.C.; Sletten, E. M.; Bertozzi, C.R., Rapid Cu-Free Click Chemistry with Readily Synthesized Biarylazacyclooctynones, J. Am. Chem. Soc. 2010, 132, 3688-3690.
Jewett et al., "Synthesis of a fluorogenic cyclooctyne activate by Cu-free click chemistry," *Org. Lett.*, Nov. 18, 2011, 13(22):5937-5939.
Jin, R. C. et al., Photoinduced Conversion of Silver Nanospheres to Nanoprisms, Science (2001), 294, 1901-1903.
Jobling, Michael et al., Fusion Proteins Containing the A2 Domain of Cholera Toxin Assemble With B Polypeptides of Cholera Toxin to Form Immunoreactive and Functional Holotoxin-Like Chimeras, Infect Immun., 60: 4915-24, 1992.
John, F. & Hendrickson, T. L. Synthesis of Truncated Analogues for Studying the Process of Glycosyl Phosphatidylinositol Modification. Org. Lett. 12, 2080-2083, (2010).
Jones et al., "Rapid PCR-cloning of full-length mouse immunoglobulin variable regions," *Nature Biotechnol.*, Jan. 1991, 9(1):88-89.
Jones et al., "Replacing the complementarity-determining regions in a human antibody with those from a mouse," *Nature*, May 29-Jun. 4, 1986, 321(6069):522-525.
Jones, "Analysis of polypeptides and proteins," *Adv. Drug Delivery Rev.*, Jan.-Apr. 1993, 10(1):29-90.
Jonges, M. et al., Dynamics of Antiviral-Resistant Influenza Viruses in the Netherlands, 2005-2008, Antiviral Res., Sep. 2009, 83(3): 290-297.
Jorgensen, Trond et al., Up-Regulation of the Oligosaccharide Sialyl Lewisx: A New Prognostic Parameter in Metastatic Prostate Cancer, Cancer Res. 55, 1817-1819, 1995.
Jose, Jiney et al., Energy transfer dyads based on Nile Red, Tetrahedron Letters (2009), 50(47), 6442-6445.
Joshi, Shantaran et al., Cell Surface Properties Associated with Malignancy of Metastatic Large Cell Lymphoma Cells, (1987) Cancer Res. 47, 3551-3557.
Joyce, J. G. et al. An oligosaccharide-based HIV-I 2G12 mimotope vaccine induces carbohydrate-specific antibodies that fail to neutralize HIV-I virions. Proc. Natl. Acad. Sci. U. S. A 105, 15684-15689, (2008).
Kakeji, Y. et al., Correlation Between Sialyl Tn Antigen and Lymphatic Metastasis in Patients with Borrmann Type IV Gastric Carcinoma, Brit. J. Cancer 71, 191-195, 1995.
Kale et al., Detection of intact influenza viruses using biotinylated biantennary S-sialosides. J Am Chem Soc. Jul. 2, 2008;130(26):8169-71.
Kalesh et al., "Peptide-based activity-based probes (ABPs) for target-specific profiling of protein tyrosine phosphatases (PTPs)," *Chem. Commun.*, Jan. 28, 2010, 46(4):589-591.
Kamkaew, A. et al., "BODIPY dyes in photodynamic therapy." Chem. Soc. Rev. 2013, 42, 77-88.
Kam et al., "Carbon nanotubes as multifunctional biological transporters and near-infrared agents for selective cancer cell destruction," *Proc. Natl. Acad. Sci. U.S.A.*, Aug. 16, 2005, 102(33):11600-11605.
Kaneko et al., "Anti-inflammatory activity of immunoglobulin G resulting from Fc sialylation," *Science*, Aug. 4, 2006, 313(5787):670-673.
Katagiri, Yohko et al Laminin Binding Protein, 34/67 Laminin Receptor, Carries Stage-Specific Embryonic Antigen-4 Epitope Defined by Monoclonal Antibody Raft.2, Biochemical and Biophysical Research Communcations, 332, 1004-1011, 2005.
Kawakami et al., "Critical role of $V\alpha14^+$ natural killer T cells in the innate phase of host protection against *Streptococcus pneumoniae* infection," *Eur. J. Immunol.*, Dec. 2003, 33(12):3322-3330.
Kawano et al., "CD1d-restricted and TCR-mediated activation of $v_\alpha 14$ NKT cells by glycosylceramides," *Science*, Nov. 28, 1997, 278(5343):1626-1629.
Kanie, Osmau et al., Orthogonal glycosylation strategy in synthesis of extended blood group B determinant. Tetrahedron Lett. 37, 4551-4554 (1996).
Kannagi et al., "New globoseries glycosphingolipids in human teratocarcinoma reactive with the monoclonal antibody directed to a developmentally regulated antigen, stage-specific embryonic antigen 3," *J. Biol. Chem.*, Jul. 25, 1983, 258(14):8934-8942.
Kannagi et al., "Stage-specific embryonic antigens (SSEA-3 and -4) are epitopes of a unique globo-series ganglioside isolated from human teratocarcinoma cells," *EMBO J.*, 1983, 2(12):2355-2361.
Kannappan, Ramaswamy et al., "Photoaffinity labeling of sialidase with a biotin-conjugated phenylaminodizairine derivative of 2,3-didehydro-2-deoxy-N-acetylneuraminic acid," *Biol. Pharm. Bull.*, Mar. 2008, 31(3):352-356.
Karlin, Samuel et al., Applications and Statistics for Multiple High-Scoring Segments in Molecular Sequences, Proc. Natl. Acad Sci. USA 90:5873-77, 1993.

(56) References Cited

OTHER PUBLICATIONS

Karlin S. et al., "Methods for assessing the statistical significance of molecular sequence features by using general scoring schemes", *Proc Natl Acad Sci USA*. Mar. 1990;87(6):2264-8.
Karmakar, M. et al., Current Trends in Research and Application of Microbial Cellulases, Research Journal of Microbiology, (2001) 6(1): 41-53.
Kato et al., "GMab-1, a high-affinity anti-3'-isoLM1/3'6'-isoLD1 IgG monoclonal antibody, raised in lacto-series ganglioside-defective knockout mice," *Biochem. Biophys. Res. Commun.*, Jan. 1, 2010, 391(1):750-755.
Kermani, Pouneh et al., Production of ScFv Antibody Fragments Following Immunization with a Phage-Displayed Fusion Protein and Analysis of Reactivity to Surface-Exposed Epitopes of the Protein F of Pseudomonas Aeruginosa by Cytofluorometry, Hybridoma, 14(4):323-328 (1995).
Kidd et al., "Profiling serine hydrolase activities in complex proteomes," *Biochemistry*, Apr. 3, 2001, 40(13):4005-4015.
Kiick, K.L. et al., Identificationof an Expanded Set of Translationally Active Methionine Analogues in *Escherichia coli*, tetrahedron 56:9487, 2001.
Kim et al., "Localization of the site of the murine IgG1 molecule that is involved in binding to the murine intestinal Fc receptor," *Eur. J. Immunol.*, 1994, 24:2429-2434.
Kim, Gap-Sue et al., AB Initio Study of Excited Electronic States and Vibronic Spectra of Phenyl Radical, Chem Phys. Lett., 2002, 3 5 2, 421.
Kimura et al., Design and Synthesis of Immobilized Tamiflu Analog on Resin for Affinity Chromatography, Tetrahedron Lett., Jul. 1, 2009, 50(26):3205-3208.
King, M. et al., New Tetramethlthiepinium (TMTI) for Copper-Free Click Chemistry, Chem. Commun. 2012, 48, 9308-9309.
Kitamura et al., "α-galactosylceramide induces early B-cell activation through IL-4 production by NKT cells," *Cell. Immunol.*, Jan. 10, 2000, 199(1):37-42.
Klein, J. et al., "Isomaltines and their N-acyl derivatives, their preparation, and use of some acyl derivatives as surfactants or for preparation of hydrophilic polymers," CAPLUS 110:95711 (1989).
Köhler et al., "Continuous cultures of fused cells secreting antibody of predefined specificity," *Nature*, Aug. 7, 1975, 256(5517):495-497.
Kolb et al., "Click chemistry: diverse chemical function from a few good reactions," *Angew. Chem. Int. Ed. Engl.*, Jun. 1, 2001, 40(11):2004-2021.
Kolb et al., "The growing impact of click chemistry on drug discovery," *Drug Discov. Today*, Dec. 15, 2003, 8(24):1128-1137.
Komba S, et al. Synthesis and Bioloical Activities of Three Sulfated Sialyl Lex Ganglioside Analogues for Clarifying the Real Carbohydrate Ligand Structure of L-Selectin, Bioorg. Med. Chem. 1996, 4, 1833-1847.
Komori, Tatsuya et al., Study on Systematizing the Synthesis of the A-Series Ganglioside Glycans GT1a, GD1a, and GM1 Using the Newly Developed N-Troc-Protected GM3 and GaIN Intermediates, Carbohydr. Res. 2009, 344, 1453.
Kong, L. et al. Expression-system-dependent modulation of HIV-I envelope glycoprotein antigenicity and immunogenicity. J. Mol. Biol. 403, 131-147, (2010).
Kontermann, "Intrabodies as therapeutic agents," *Methods*, Oct. 2004, 34(2):163-170.
Kos, "Regulation of adaptive immunity by natural killer cells," Immunol. Res., 1998, 17(3):303-312.
Koshihara et al., 1984, Biochmica et biophysica acta, 792(1), pp. 92-97.
Kostelny et al., "Formation of a bispecific antibody by the use of leucine zippers," *J. Immunol.*, Mar. 1, 1992, 148(5):1547-1553.
Kotteas et al., Immunotherapy for pancreatic cancer, J cancer Res Clin Oncol, 142(8): 1795-1805, 2016.
Kozbor, "A human hybrid myeloma for production of human monoclonal antibodies," *J. Immunol.*, Dec. 1984, 133(6):3001-3005.
Kriegler M et al., "A novel form of NF/cachectin is a cell surface cytotoxic transmembrane protein: ramifications for the complex physiology of TNF" *Cell.* Apr. 8, 1988;53(1):45-53.
Krise, Jeffrey et al., Prodrugs of Phosphates, Phosphonates, and Phosphinates, Adv. Drug Deliv. Rev. 1996, 19(2), 287-310.
Kruis et al., Low dose balsalazide (1.5 g twice daily) and mesalazine (0.5 g three times daily) maintained remission of ulcerative colitis but high dose alsalazide (3.0 g twice daily) was superior in preventing relapses. Gut. Dec. 2001;49(6):783-9.
Kubin, R. F. et al., Fluorescence Quantum Yields of Some Rhodamine Dyes, Luminescence 1982, 27, 455-462.
Kubler-Kielb, J. et al., A New Method for Conjugation of Carbohydrates to Proteins Using an Aminooxy-Thiol Heterbifunctional Linker, J Org Chem 2005, 70, 6987-6990.
Kudo et al., "Up-regulation of a set of glycosyltransferase genes in human colorectal cancer," *Lab. Invest.*, Jul. 1998, 78(7):797-811.
Kwong, Peter et al., Rational Design of Vaccines to Elicit Broadly Neutralizing Antibodies to HIV-I. Cold Spring Harb.Perspect. Med. 1, 2011, 1-16.
Lantz et al., "An invariant T cell receptor a chain is used by a unique subset of major histocompatibility complex class I-specific $CD4^+$ and $CD4^-8^-$ T cells in mice and humans," *J. Exp. Med.*, Sep. 1, 1994, 180(3):1097-1106.
Lau et al., "N-Glycans in cancer progression," *Glycobiology*, Oct. 2008, 18(10):750-760.
Lau, K. et al. Highly efficient chemoenzymatic synthesis of β1-4-linked galactosides with promiscuous bacterial β1-4-galactosyltransferases. Chem. Commun. 46, 6066-6068, (2010).
Le, Mai et al., Avian flu: Isolation of Drug-Resistant H5N1 Virus, Nature, Oct. 20, 2005, 437(7062):1108.
Lebens et al., Mucosal vaccines based on the use of cholera toxin B as immunogen and antigen carrier, *Dev. Biol. Stand.*, 1994, 82:215-227.
Le Droumaguet, C. et al., Fluorogenic Click Reaction., Chem. Soc. Rev. 2010, 39, 1233-1239.
Lederman et al., A single amino acid substitution in a common African allele of the CD4 molecule ablates binding of the monoclonal antibody, OKT4, Molecular Immunology, 28, 1171-1181 (1991).
Lee et al., Analogs of Cell Surface Carbohydrates. Synthesis of D-Galactose Derivatives Having an Ethynyl, Vinyl or Epoxy Residue at c-5. Carbohydrate Research 1988, vol. 176, pp. 59-72.
Lee et al., "Bivalent antibody phage display mimics natural immunoglobulin," *J. Immunol. Methods*, Jan. 2004, 284(1-2):119-132.
Lee et al., "High-affinity human antibodies from phage-displayed synthetic Fab libraries with a single framework scaffold," *J. Mol. Biol.*, Jul. 23, 2004, 340(5):1073-1093.
Lee et al., A new Solvent System for Efficient Synthesis of 1,2,3-Triazoles, Tetrahedron Lett., Jul. 17, 2006, 47(29):5105-5109.
Lee et al., An Efficient and Practical Method for the Synthesis of Mono-N-Protected α,ω-diaminoalkanes, Tetrahedron Lett., Apr. 2, 2001, 42(14):2709-2711.
Lee, H.K. et al. Reactivity-based one-pot synthesis of oligomannoses: defining antigens recognized by 2G12, a broadly neutralizing anti-HIV-I antibody. Angew. Chem. Int. Ed. 43, 1000-1003, (2004.
Lee et al., Immunogenicity Study of Globo H Analogues with Modification at the Reducing or Nonreducing end of the tumor antigen, J Am Chem Soc, 136: 16844-16853 (2014).
Lefranc et al., "IMGT, The international ImMunoGeneTics database," *Nucleic Acids Res.*, Jan. 1, 1999, 27(1):209-212.
Lehninger, *Biochemistry: The Molecular Basis of Cell Structure and Function*, $2^{nd}$ ed., 1975, pp. 73-75, Worth Publishers, New York.
Lei, Jianqing et al., Potential antitumor applications of a monoclonal antibody specifically targeting human papilloma virus 16 E749-57 peptide, Microbiology and Immunology, 2012, vol. 56, pp. 456-462.
Lemieux, R. U. et al., Halide ion catalyzed glycosidation reactions. Syntheses of a-linked disaccharides. J. Am. Chem. Soc. 97(14), 4056-62, (1975).
Leung et al., "A method for random mutagenesis of a defined DNA segment using a modified polymerase chain reaction," *Technique—A Journal of Methods in Cell and Molecular Biology*, Aug. 1989, 1(1):11-15.

(56) References Cited

OTHER PUBLICATIONS

Lew et al., Discovery and Development of GS 4104 (oseltamivir): an Orally Active Influenza Neuraminidase Inhibitor, Curr Med Chem, Jun. 2000, 7(6):663-672.

Li et al., β-endorphin omission analogs: Dissociation of Immunoreactivity from other biological activities, Proc Natl Avad Sci USA, 77:3211-3214 (1980).

Li, Y. L. et al., Crystallization and Melting Behaviors of PPC-BS/PVA Blends, 19, 1557-1566, 2003.

Li, Henghui et al., MALDI-MS Analysis of Sialylated N-Glycan Linkage Isomers Using Solid-Phase Two Step Derivatization Method, Analytica Chimica Acta 924 (2016) 77-85.

Li et al., "Design of a potent CD1d-binding NKT cell ligand as a vaccine adjuvant," Proc. Natl. Acad. Sci. USA, Jul. 20, 2010, 107:13010-13015.

Li, J.; Hu, M.; Yao, S. Q. "Rapid synthesis, screening, and identification of xanthone and xanthene-based fluorophores using click chemistry." Org. Lett. 2009, 11, 3008-3011.

Li, Lingling, et al., "Syntheses and spectral properties of functionalized, water-soluble BODIPY derivatives." J. Org. Chem. 2008, 73, 1963-1970.

Li, L. et al. Efficient chemoenzymatic synthesis of an N-glycan isomer library. Chem. Sci. 6, 5652-5661 (2015).

Liang et al., "Quantitative microarray analysis of intact glycolipid-CD1d interaction and correlation with cell-based cytokine production," J. Am. Chem. Soc., Sep. 17, 2008, 130(37):12348-12354.

Liang, P.H. et al., Quantitative Analysis of Carbohydrate-Protein Interactions Using Glycan Microarrays: Determination of Surface and Solution Dissociation Constants, J. Amer. Chem. Sci. 2007, 129, 11177-11184.

Liang, Yuh-Jin et al., Switching of the Core Structures of Glycosphingolipids From Blobo- and Lacto- to Ganglio-Series Upon Human Embryonic Stem Cell Differentiation, PNAS, 107(52), Dec. 2010, 22564-22569.

Liao, Shih-Fen et al., Immunization of Fucose-Containing Polysaccharides From Reishi Mushroom Induces Antibodies to Tumor-Associated Globo H-Series Epitopes, Proceedings National Academy of Sciences PNAS, vol. 110, No. 34, Aug. 1, 2013, pp. 13809-13814.

Lin et al., A common glycan structure on immunoglobulin G for enhancement of effector functions, PNAS, Aug. 25, 2015, vol. 112, No. 34, p. 10611-10616.

Lindmark et al., "Binding of immunoglobulins to protein a and immunoglobulin levels in mammalian sera," J. Immunol. Meth., Aug. 12, 1983, 62(1):1-13.

Liu C, et al., "Expansion of spleen myeloid suppressor cells represses NK cell cytotoxicity in tumor-bearing host" Blood. May 15, 2007;109(10):4336-42. Epub Jan. 23, 2007.

Liu et al., "Activity-based protein profiling: the serine hydrolases," Proc. Natl. Acad. Sci. USA, Dec. 21, 1999, 96(26):14694-14699.

Liu et al., "Eradication of large colon tumor xenografts by targeted delivery of maytansinoids," Proc. Natl., Acad. Sci. U.S.A., Aug. 6, 1996, 93(16):8618-8623.

Liu et al., Enhanced anti-influenza agents conjugated with anti-inflammatory activity. J Med Chem. Oct. 11, 2012;55(19):8493-501.

Liu et al., Intramolecular ion-pair prodrugs of znamivir nad guanidino-oseltamivir. Bioorganic & Medicinal Chemistry. Jun. 2011; 19(16):4796-4802.

Liu et al., Synthesis and anti-influenza activities of carboxyl alkoxyalkyl esters of 4-guanidino-Neu5Ac2en (zanamivir). Bioorg Med Chem Lett. Sep. 1, 2007;17(17):4851-4. Epub Jun. 20, 2007.

LoBuglio et al., "Mouse/human chimeric monoclonal antibody in man: kinetics and immune response," Proc. Natl. Acad. Sci. U.S.A., Jun. 1989, 86(11):4220-4224.

Lode et al., "Targeted therapy with a novel enediyne antibiotic calicheamicin $\Theta^i_1$ effectively suppresses growth and dissemination of liver metastases in a syngeneic model of murine neuroblastoma," Cancer Res., Jul. 15, 1998, 58(14):2925-2928.

Lonberg et al., "Antigen-specific human antibodies from mice comprising four distinct genetic modifications," Nature, Apr. 28, 1994, 368(6474):856-859.

Lonberg et al., "Human antibodies from transgenic mice," Int. Rev. Immunol., 1995, 13(1):65-93.

Lopes, J.F. et al., Simulataneous Chromatographic Separation of Enantiomers, Anomers and Structural Isomers of Some Biologically Relevant Monsaccharides. J. Chomatogr. A, (2008) 1188:34-42.

Lou, et al., Stage-specific embryonic antigent-4 as a potential therapeutic target in glioblastoma multiforms and other cancers. Proc Natl Acad Sci USA 2014, 111(7):2482-7.

Loudet, A.; Burgess, K. "BODIPY dyes and their derivatives: syntheses and spectroscopic properties." Chem. Rev. 2007, 107, 4891-4932.

Louis et al., "The 2007 WHO classification of tumours of the central nervous system," Acta. Neuropathol., Aug. 2007, 114(2):97-109.

Lu et al., "Design of a mechanism-based probe for neuraminidase to capture influenza viruses," Angew. Chem. Int. Ed. Engl., Oct. 28, 2005, 44(42):6888-6892.

Lu, Guokai et al., Reactivity-Based One-Pot Synthesis of Immunosuppressive Glycolipids From the Caribbean Sponge Plakortis Simplex, J. Chem. 2009, 27, 2217-2222.

Lu et al., "Single chain anti-c-Met antibody conjugated nanoparticles for in vivo tumor-targeted imaging and drug delivery," Biomaterials, Apr. 2011, 32(12):3265-3274.

MacBeath, G. and Schreiber, S. L., Printing Proteins as Microarrays for High-Throughput Function Determination, Science, 289, 1760-1763, 2000.

Macfarlane GT, et al., "Formation of glycoprotein degrading enzymes by Bacteroides fragilis" FEMS Microbiol Lett. Jan. 15, 1991;61(2-3):289-93.

Makino et al., Predominant expression of invariant $V_\alpha 14^+$ TCR α chain in NK1.1$^+$ T cell populations, Int. Immunol., Jul. 1995, 7(7):1157-1161.

Mandler et al "Immunoconjugates of geldanamycin and anti-HER2 monoclonal antibodies: antiproliferative activity on human breast carcinoma cell lines," J. Nat. Cancer Inst., Oct. 4, 2000, 92(19):1573-1581.

Mandler et al., "Modifications in synthesis strategy improve the yield and efficacy of geldanamycin-herceptin immunoconjugates," Bioconjugate Chem., Jul.-Aug. 2002, 13(4):786-791.

Mandler et al., "Synthesis and evaluation of antiproliferative activity of a geldanamycin-Herceptin™ immunoconjugate," Bioorganic & Med. Chem. Letters, May 15, 2000, 10(10):1025-1028.

Mandal, M., Dudkin, V. Y., Geng, X. & Danishefsky, S. J. In pursuit of carbohydrate-based HIV vaccines, part I: The total synthesis of hybrid-type gp 120 fragments. Angew. Chem. Int. Ed. 43, 2557-2561, (2004).

Månsson et al., "Characterization of new gangliosides of the lactotetraose series in murine xenografts of a human glioma cell line," FEBS Lett., May 26, 1986, 201(1):109-113.

Marasco et al., "Design, intracellular expression, and activity of a human anti-human immunodeficiency virus type 1 gp120 single-chain antibody," Proc. Natl. Acad. Sci. U.S.A., Aug. 15, 1993, 90(16):7889-7893.

Marasco, "Intrabodies: turning the humoral immune system outside in for intracellular immunization," Gene Therapy, Jan. 1997, 4(1):11-15.

Marcato et al., "Chapter 17: The Rocky Road from Cancer Stem Cell Discovery to Diagnostic Applicability," Cancer Stem Cells Theories and Practice, pp. 335-360, Mar. 22, 2011.

Marks et al., "By-passing immunization. Human antibodies from V-gene libraries displayed on phage," J. Mol. Biol., Dec. 5, 1991, 222(3):581-597.

Marks et al., "By-passing immunization: Building high affinity human antibodies by chain shuffling," Nature Biotechnology, Jul. 1992, 10(7):779-783.

Massart, R., IEEE Transactions on Magnetics, 17, 1247 (1981).

Masuko, T. et al., Thiolation of Chitosan. Attachment of Proteins Via Thioether Formation, Biomacromolecules 2005, 6, 880-884.

Mather et al., "Culture of testicular cells in hormone-supplemented serum-free medium," Annals N.Y. Acad. Sci., 1982, 383:44-68.

(56) References Cited

OTHER PUBLICATIONS

Mather, "Establishment and characterization of two distinct mouse testicular epithelial cell lines," *Biol. Reprod.*, Aug. 1980, 23(1):243-252.
Matrosovich M, et al., The Surface Glycoproteins of H5 Influenza Viruses Isolated From Humans, Chickens, and Wild Aquatic Birds Have Distinguishable Properties, J. Virol. 1999, 73, 1146-1155.
Matsuda et al., "Structure and physical map of 64 variable segments in the 3' 0.8-megabase region of the human immunoglobulin heavy-chain locus," *Nature Genet.*, Jan. 1993, 3(1):88-94.
Matz et al., "Fluorescent proteins from nonbioluminescent *Anthozoa* species," *Nat. Biotechnol.*, Oct. 1999, 17(10):969-973.
McCafferty et al., "Phage antibodies: Filamentous phage displaying antibody variable domains," *Nature*, Dec. 6, 1990, 348:552-554.
McKimm-Breschkin et al., "Tethered neuraminidase inhibitors that bind an influenza virus: a first step towards a diagnostic method for influenza," Angew. Chem. Int. Ed Engl., Jul. 14, 2003, 42(27):3118-3121.
McKimm-Breschkin, "Resistance of influenza viruses to neuraminidase inhibitors—a review," Antiviral Res., Jul. 2000, 47(1): 1-17.
McKimm-Breschkin, J. et al., "Neuraminidase Sequence Analysis and Susceptibilities of Influenza Virus Clinical Isolates to Zanamivir and Oseltamivir," Antimicrobial Agents and Chemotherapy, vol. 47, No. 7, Jul. 2003, in 10 pages.
Meezan et al., "Comparative studies on the carbohydrate-containing membrane components of normal and virus-transformed mouse fibroblasts: II: Separation of glycoproteins and glycopeptides by Sephadex chromatography," *Biochemistry*, Jun. 1969, 8(6):2518-2524.
Medelson et al., NKp46 O-glycan Sequences that are involved in the interaction with Hemagglutinin Type 1 of Influenza Virus. J. Virol. Feb. 10, 2010, 84(8):3789-3797.
McLellan, J. S. et al. Structure of HIV-I gp120 V1/V2 domain with broadly neutralizing antibody PG9. Nature 480, 336-343, 2011.
Merck, MAB4304, Anti-Stage-Specific Embryonic Antigen-4 Antibody, Clone MC-813-70, 4 Pages, 2017.
Meyer, "Malignant gliomas in adults," *N. Engl. J. Med.*, Oct. 23, 2008, 359(17):1850.
Milstein, C & Cuello, AC, Hybrid Hydridomas and their use in immunohistochemistry, Nature 305, 537-540, Oct. 1993.
Mimura et al., "Role of oligosaccharide residues of IgG1-Fc in FcγRIIb binding," *J. Biol. Chem.*, Dec. 7, 2001, 276(49):45539-45547.
Mishima et al., "Growth suppression of intracranial xenografted glioblastomas overexpressing mutant epidermal growth factor receptors by systemic administration of monoclonal antibody (mAb) 806, a novel monoclonal antibody directed to the receptor," *Cancer Res.*, Jul. 15, 2001, 61(14):5349-5354.
Miyagi et al., "Mammalian sialidases: Physiological and pathological roles in cellular functions," *Glycobiology*, Jul. 2012, 22(7):880-896.
Miyagi et al., "Plasma membrane-associated sialidase as a crucial regulator of transmembrane signalling," *J. Biochem.*, Sep. 2008, 144(3):279-285.
Miyagi et al., "Sialidase and malignancy: a minireview," *Glycoconj. J.*, 2004, 20(3):189-198.
Miyagi, "Aberrant expression of sialidase and cancer progression," *Proc. Jpn. Acad. Ser. B. Phys. Biol. Sci.*, 2008(10), 84:407-418.
Miyaji, E. N. et al., Induction of Neutralizing Antibodies Against Diphtheria Toxin by Priming with Recombinant *Mycobacterium bovis* BCG Expressing CRM197, a Mutant Diphtheria Toxin, Infect. Immun. 2001, 69, 869.
Miyamoto et al., "A synthetic glycolipid prevents autoimmune encephalomyelitis by inducing $T_H2$ bias of natural killer T cells," *Nature*, Oct. 4, 2001, 413(6855):531-534.
Moal, E. Le et al., Enhanced Fluorescence Cell Imaging with Metal-Coated Slides, Biophysical Journal, vol. 92, 2150-2161, Mar. 2007.

Monti et al., "Sialidases in vertebrates: a family of enzymes tailored for several cell functions," *Adv. Carbohydr. Chem. Biochem.*, 2010, 64:403-479.
Moody, M. D. et al., Array-based ELISAs for High-Throughput Analysis of Human Cytokines. Biotechniques (2001), 31, 186-194.
Morelle, W. et al., "The Mass Spectrometric Analysis of Glycoproteins and their Glycan Structures", *Review in Current Analytical Chemistry*, vol. 1, No. 1 (2005), pp. 29-57.
Mori K, et al., "Non-fucosylated therapeutic antibodies: the next generation of therapeutic antibodies" *Cytotechnology*. Dec. 2007;55(2-3):109-14. Epub Oct. 31, 2007.
Morimoto et al., "Single-step purification of F(ab')$_2$ fragments of mouse monoclonal antibodies (immunoglobulins G1) by hydrophobic interaction high performance liquid chromatography using TSKgel Phenyl-5PW," *J. Biochem. Biophys. Meth.*, Mar. 1992, 24(1-2):107-117.
Morphy et al., Designed multiple ligands. An emerging drug discovery paradigm. J Med Chem. Oct. 20, 2005;48(21):6523-43.
Morphy et al., From magic bullets to designed multiple ligands. Drug Discov Today. Aug. 1, 2004;9(15):641-51.
Morrison et al., "Chimeric human antibody molecules: mouse antigen-binding domains with human constant region domains," *Proc. Natl. Acad. Sci. U.S.A.*, Nov. 1984, 81(21):6851-6855.
Morrison, "Immunology. Success in specification," *Nature*, Apr. 28, 1994, 368(6474):812-813.
Moscona, "Global transmission of oseltamivir-resistant influenza," N Engl. J Med, Mar. 5, 2009, 360(10):953-956.
Moscona, Oseltamivir Resistance—Disabling Our Influenza Defenses, The New England Journal of Medicine, 2005, vol. 353, pp. 2633-2636.
Mosmann et al., "The expanding universe of T-cell subsets: Th1, Th2 and more," *Immunol. Today*, Mar. 1996, 17(3):138-146.
Mossong et al., "Emergence of oseltamivir-resistant influenza A H1N1 virus during the 2007-2008 winter season in Luxembourg: clinical characteristics and epidemiology," Antiviral Res., Oct. 2009, 84(1):91-94.
Mouquet, H. et al. Complex-type N-glycan recognition by potent broadly neutralizing HIV antibodies. Proc. Natl. Acad. Sci. U. S. A 109, E3268-E3277, (2012).
Munson et al., "Ligand: a versatile computerized approach for characterization of ligand-binding systems," *Anal. Biochem.*, Sep. 1, 1980, 107(1):220-239.
Murphy, C. I. et al. Enhanced expression, secretion, and large-scale purification of recombinant HIV-I gp 120 in insect cell using the baculovirus egt and p67 signal peptides. Protein Expres. Purif. 4, 349-357 (1993).
Muthana, S., Yu, H., Huang, S., and Chen, X. Chemoenzymatic synthesis of size-defined polysaccharides by sialyltransferase-catalyzed block transfer of oligosaccharides. J. Am. Chem. Soc. 129, 11918-11919, (2007).
Natarajan et al, Caffeic acid phenethyl ester is a potent and specific inhibitor of activation of nuclear transcription factor NF-kappa B. Proc Natl Acad Sci USA Aug. 20, 1996;93(17):9090-5.
Neuberger et al., "Recombinant antibodies possessing novel effector functions," *Nature*, Dec. 13-19, 1984, 312(5995):604-608.
Neuberger, "Generating high-avidity human Mabs in mice," *Nature Biotechnol.*, Jul. 1996, 14(7):826.
Ni, Jing et al Immunoassay Readout Method Using Extrinsic Raman Labels Adsorbed on Immunogold Colloids, Anal. Chem., 1999, 71(21), pp. 4903-4908.
Nicolaou et al., "Calicheamicin $\Theta^I_1$: A rationally designed molecule with extremely potent and selective DNA cleaving properties and apoptosis inducing activity," *Angew. Chem. Intl. Ed. Engl.*, Feb. 1, 1994, 33(2):183-186.
Niculescu-Duvaz et al., "Antibody-directed enzyme prodrug therapy (ADEPT): A review," *Adv. Drg. Del. Rev.*, Jul. 7, 1997, 26(2-3):151-172.
Nieuwenhuis et al., "CD1d-dependent macrophage-mediated clearance of *Pseudomonas aeruginosa* from lung," *Nat. Med.*, Jun. 2002, 8(6):588-593.
Nielsen, U. B. et al., Multiplexed Sandwich Assays in Microarray Format, Journal Immunol. Meth. (2004), 290, 107-120.

(56) References Cited

OTHER PUBLICATIONS

Ning, X. et al., Visualizing Metabolically-Labeled Glycoconjugates of Living Cells by Copper-Free and Fast Huisgen Cycloadditions, J. Angew. Chem. Int. Ed. 2008, 47, 2253-2255.

Noto et al., "CD44 and SSEA-4 positive cells in an oral cancer cell line HSC-4 possess cancer stem-like cell characteristics," Oral Oncol., Aug. 2013, 49(8):787-795.

Nowak, MW et al., Nicotinic Receptor Binding Site Probed With Unnatural Amino Acid Incorporation in Intact Cells, Science 268:439, 1995.

Novotný et al., "Structural invariants of antigen binding: comparison of immunoglobulin $V_L$—$V_H$ and $V_L$—$V_L$ domain dimers," Proc. Natl. Acad. Sci. USA, Jul. 1985, 82(14):4592-4596.

Oberli, Matthias et al., A Possible Oligosaccharide-Conjugate Vaccine Candidate for Clostridium Difficile is Antigenic and Immunogenic, Chemistry & Biology, vol. 18, No. 5, May 2011, 580-588.

Office Action dated Dec. 3, 2013, from corresponding Chinese Patent Application No. 201180034218.3, 15 total pages.

Office Action dated Oct. 22, 2014, from corresponding Chinese Patent Application No. 201180034218.3, 16 total pages.

O'Garra, "Cytokines induce the development of functionally heterogeneous T helper cell subsets," Immunity, Mar. 1998, 8(3):275-283.

Okada, Yoshio et al. Changes in the Expression of Sialyl-Lewisx, a Hepatic Necroinflammation-Associated Carbohydrate Neoantigen, in Human Depatocellular Carcinomas, (1994) Cancer 73, 1811-1816.

Okamura et al., "Interleukin-18: a novel cytokine that augments both innate and acquired immunity," Adv. Immunol., 1998, 70:281-312.

Olden, Kenneth et al., Carbohydrate Moieties of Glycoproteins: A Re-Evaluation of Their Function, Biochem et Biophys Acta 650:209-232 (1982).

Orlandi et al., "Cloning immunoglobulin variable domains for expression by the polymerase chain reaction," Proc. Natl. Acad. Sci. U.S.A., May 1989, 86(10):3833-3837.

Ørum et al., "Efficient method for constructing comprehensive murine Fab antibody libraries displayed on phage." Nucleic Acids Res., Sep. 25, 1993, 21(19):4491-4498.

Otsubo N, et al., An Efficient and Straightforward Synthesis of Sialyl Lex Glycolipid as a Potent Selectin Blocker[[1]], Carbohydr. Res. 1998, 306, 517-530.

Ottolini et al., Combination anti-inflammatory and antiviral therapy of influenza in a cotton rat model. Pediatr. Pulmonol. 2003:36;290-4.

Oyelaran, 0. & Gildersleeve, J. C. Glycan arrays: recent advances and future challenges. Curr. Opin. Chem. Biol. 13, 406-413, (2009).

Pabst, M. et al., Glycan profiles of the 27 Nglycosylation sites of the HIV envelope protein CN54gp140. Biol. Chem. 393, 719-730, (2012).

Pacino, G. et al., Purification and Characterization of a Breast-Cancer-Associated Glycoprotein Not Expressed in Normal Breast and Identified by Monoclonal Antibody 83D4, Br. J. Cancer, 1991, 63, 390-398.

Pan, Yanbin et al., Synthesis and Immunological Properties of N-Modified GM3 Antigens as Therapeutic Cancer Vaccines, J. Med. Chem., 48(3), 875-883, 2005.

Pancera, M. et al. Crystal structure of PG16 and chimeric dissection with somatically related PG9: structure-function analysis of two quaternary-specific antibodies that effectively neutralize HIV-I. J. Virol. 84, 8098-8110, (2010).

Pancera, M. et al. Structural basis for diverse N-glycan recognition by HIV-I-neutralizing V1-V2-directed antibody PG16. Nat. Struct. Mol. Biol. 20, 804-813, (2013).

Papanastassiou et al., "The potential for efficacy of the modified (ICP 34.5⁻) herpes simplex virus HSV1716 following intratumoural injection into human malignant glioma: a proof of principle study," Gene Therapy, Mar. 2002, 9(6):398-406.

Parker, C. A.; Rees, W. T., Correction of Fluorescence Spectra and Measurement of Fluorescence Quantum Efficiency, Analyst 1960, 85, 587-600.

Parrish, M. L. et al., A Microarray Platform Comparison for Neuroscience Applications, J. Neurosci. Methods, 2004, 132, 57-68.

Patricelli et al., "Functional interrogation of the kinome using nucleotide acyl phosphates," Biochemistry, Jan. 16, 2007, 46(2):350-358.

Paulson, J. C., Blixt, 0. & Collins, B. E. Sweet spots in functional glycomics. Nat. Chem. Biol. 2, 238-248, (2006).

Pearlman et al., Peptide and Protein Drug Delivery, Chapter 6: Analysis of Protein Drugs, Lee, ed., 1991, pp. 247-301, Marcel Dekker Publishing, New York.

Peelle et al., "Characterization and use of green fluorescent proteins from Renilla mulleri and Ptilosarcus guernyi for the human cell display of functional peptides," J. Protein Chem., Aug. 2001, 20(6):507-519.

Peipp et al., "Antibody fucosylation differentially impacts cytotoxicity mediated by NK and PMN effector cells," Blood, 2008, 112(6):2390-2399.

Peiris et al., Re-emergence of fatal human influenza A subtype H5N1disease. Lancet. Feb. 21, 2004 ;363(9409):617-9.

Pejchal, R. et al. A potent and broad neutralizing antibody recognizes and penetrates the HIV glycan shield. Science 334, 1097-1103, (2011).

Pellicci et al., "Differential recognition of CD1d-α-galactosyl ceramide by the Vβ8.2 and Vβ7 semi-invariant NKT T-cell receptors," Immunity, Jul. 17, 2009, 31(1):47-59.

Perlmutter, R.M. et al., Subclass Restriction of Murine Anti-Carbohydrate Antibodies, Journal of Immunology 1978, 121, 566-572.

Pettit, George et al., Antineoplastic Agents. Part 189. The Absolute Configuration and Synthesis of Natural (−)-Dolastatin 10, J Am Chem Soc. 111:5463-5465 (1989).

Pettit, George et al., Dolastatins 23: Stereospecific Synthesis of Dolaisoleuine, J Chem Soc Perkin Trans. 15:853-858 (1996).

Pettit, George et al., Antineoplastic Agents 365. Dolastatin 10 SAR Probes, Anti-Cancer Drug Design 13:243-277 (1998).

Pettit, Robin et al., Specific Activities of Dolastatin 10 and Peptide Derivatives Against Cryptococcus Neoformans, Antimicrob Agents Chemother. 42:2961-2965 (1998).

Pettit, George et al., The Dolastatins; 18: Stereospecific Synthesis of Dolaproine, Synthesis, 719-725 (1996).

Piizi, G. and Hardinger, S., Stereochemistry: an Introduction, UCLA Chemistry 30A Presentation, Fall 2002, in 40 pages.

Plückthun, "Mono- and bivalent antibody fragments produced in Escherichia coli: Engineering, folding and antigen binding," Immunol. Rev., Dec. 1992, 130:151-188.

Plückthun, Handbook of Experimental Pharmacology, vol. 113: The Pharacology of Monoclonal Antibodies, Chapter 11: Antibodies from Escherichia coli, Rosenberg et al., eds., 1994, pp. 269-315, Springer-Verlag, Berlin.

Poloukhtine et al., "Selective labeling of living cells by a photo-triggered click reaction," J. Am. Chem. Soc., Nov. 4, 2009, 131(43):15769-15776.

Porcelli, S.A., "Preparation of a-galactosylceramide derivatives as modulators of immunity and autoimmunity," CAPLUS 147:440317 (2007).

Potier et al., "Fluorometric assay of neuraminidase with a sodium ( 4-methylumbelliferyl-alpha-D-N-acetylneuraminate) substrate," Anal. Biochem., Apr. 15, 1979, 94(2):287-296.

Pratt, M. R. & Bertozzi, C. R. Chemoselective ligation applied to the synthesis of a biantennary N-linked glycoform of CD52. J Am. Chem. Soc. 125, 6149-6159, (2003).

Prescher, J. A.; Bertozzi, C.R. "Chemistry in living systems." Nat. Chem. Biol. 2005, 1, 13-21.

Presta et al., "Humanization of an antibody directed against IgE," J. Immunol., Sep. 1, 1993, 151(5):2623-2632.

Presta et al., "Humanization of an anti-vascular endothelial growth factor monoclonal antibody for the therapy of solid tumors and other disorders," Cancer Res., Oct. 15, 1997, 57(20):4593-4599.

Presta, "Antibody engineering," Curr. Opin. Biotechnol., Aug. 1992, 3(4):394-398.

(56) References Cited

OTHER PUBLICATIONS

Presta, "Antibody engineering," *Curr. Opin. Struct. Biol.*, Aug. 1992, 2(4):593-596.
Pritchard, L. K. et al. Structural Constraints Determine the Glycosylation of HIV-I Envelope Trimers. Cell Rep. 11, 1604-13, (2015).
Pritchard, Laura et al., Cell- and Protein-Directed Glycosylation of Native Cleaved HIV-I Envelope. J. Virol. 89, 8932-44, (2015).
Proba et al., "Functional antibody single-chain fragments from the cytoplasm of *Escherichia coli*: influence of thioredoxin reductase (TrxB)," *Gene* Jul. 4, 1995, 159(2):203-207.
Pshezhetsky, M. Potier, J. Biol. Chem. 1996, 271, 28359-28365. Association of N-acetylgalactosamine-6-sulfate sulfatase with the multienzyme lysosomal complex of betagalactosidase, cathepsin A, and neuraminidase. Possible implication for intralysosomal catabolism of keratan sulfate.
Puigbò P, Guzmán E, Romeu A, Garcia-Vallvé S. Optimizer: a web server for optimizing the codon usage of DNA sequences. *Nucleic Acids Res.* Jul. 2007;35(Web Server issue):W126-31. Epub Apr. 16, 2007.
Qi, Jianjun et al., Developing visible fluorogenic 'clickon' dyes for cellular imaging, Bioconjugate Chem. 2011, 22, 1758-1762.
Rabbani, Said et al., Glycosyltransferases: An efficient tool for the enzymatic synthesis of oligosaccharides and derivatives as well as mimetics thereof Chimia 60, 23-27, (2006).
Raju et al., "Synthesis and evaluation of 3"- and 4"-deoxy and -fluoro analogs of the immunostimulatory glycolipid, KRN7000," *Bioorg. Med. Chem. Lett.*, 2009, 19:4122-4125.
Ramm et al., "The periplasmic *Escherichia coli* peptidylprolyl cis,trans-isomerase FkpA. II. Isomerase-independent chaperone activity in vitro," *J. Biol. Chem.*, Jun. 2, 2000, 275(22):17106-17113.
Rana, G. Kucukayan-Dogu, E. Bengu "Growth of vertically aligned carbon nanotubes over self-ordered nano-porous alumina films and their surface properties" Applied Surface Science, 2012, 258 7112-7117.
Raska, M. et al. Glycosylation patterns of HIV-I gp120 depend on the type of expressing cells and affect antibody recognition. J. Biol. Chem. 285, 20860-20869, (2010).
Ravetch et al., "Divergent roles for Fc receptors and complement in vivo," *Ann. Rev. Immunol.*, 1998, 16:421-432.
Ravetch et al., "Fc receptors," *Annu. Rev. Immunol.*, 1991, 9:457-492.
Reyes et al., "Expression of human β-interferon cDNA under the control of a thymidine kinase promoter from herpes simplex virus," *Nature*, Jun. 17, 1982, 297(5867):598-601.
Riechmann et al., "Reshaping human antibodies for therapy," *Nature*, Mar. 24, 1988, 332(6162):323-327.
Rillahan, C. D. & Paulson, J. C. Glycan microarrays for decoding the glycome. Annu. Rev. Biochem. 80, 797-823, (2011).
Ritamo, Ilja al., Comparison of the Glycosylation of in Vitro Generated Polyclonal Human IgG and Therapeutic Immunoglins, Mol Immunol. Feb. 2014; 57(2): 255-62.
Rogers, GN et al., Single Amino Acid Substitutions in Influenza Haemagglutinin Change Receptor Binding Specificity. Nature, 304:76, 1983.
Rogers, GN et al., Receptor Determinants of Human and Animal Influenza Virus Isolates: Differences in Receptor Specificity of the H3 Hemagglutinin Based on Species of Origin. Virology, 127:361, 1983.
Roguska et al., "Humanization of murine monoclonal antibodies through variable domain resurfacing," *Proc. Nati. Acad. Sci. U.S.A.*, Feb. 1, 1994, 91(3):969-973.
Romagnani, "Induction of $T_H1$ and $T_H2$ responses: a key role for the 'natural' immune response?" *Immunol. Today*, Oct. 1992, 13(10):379-381.
Roos et al., "Specific inhibition of the classical complement pathway by C1q-binding peptides," *J. Immunol.*, Dec. 15, 2001, 167(12):7052-7059.
Rosenstein, N.E. et al, Meningococcal Disease, N Engl J Med 2001, 344, 1378-1388.
Rostovtsev et al., "A stepwise Huisgen cycloaddition process catalyzed by copper(I) regioselective ligation of azides and terminal alkynes," *Angew. Chem. Int. Ed. Engl.*, Jul. 15, 2002, 41(41):2596-2599.
Roth, Jurgen et al., Reexpression of Poly(sialic Acid) Units of the Neural Cell Adhesion Molecule in Wilms Tumor, Proc. Natl. Acad. Sci. 85, 2999-3000, 1988.
Rowland et al, "Drug localisation and growth inhibition studies of vindesine-monoclonal anti-CEA conjugates in a human tumour xenograft," *Cancer Immunol. Immunother.*, 1986, 21(3):183-187.
Rudnick et al., Affinity and Avidity in Antibody-Based Tumor Targeting, Can Biotherp & Radoipharm, 24, 155-162 (2009).
Ruiz et al., "IMGT, the international ImMunoGeneTics database," *Nucl. Acids Res.*, Jan. 1, 2000, 28(1):219-221.
Russell et al., "The structure of H5N1 avian influenza neuraminidase suggests new opportunities for drug design," Nature, Sep. 7, 2006, 443(7107):45-49.
Saito, Seiichi et al., Haptoglobin-β Chain Defined by Monoclonal Antibody RM2 as a Novel Serum Marker for Prostate Cancer, Int. J Cancer, 2008, 123(3), 633-640.
Saito et al., "Expression of globo-series gangliosides in human renal cell carcinoma," *Jpn. J. Cancer Res.*, Jul. 1997, 88(7):652-659.
Saito et al., "Human α2,3-sialyltransferase (ST3Gal II) is a stage-specific embryonic antigen-4 synthase," *J. Biol. Chem.*, Jul. 18, 2003, 278(29):26474-26479.
Saitoh, Osamu et al., Differential Glycosylation and Cell Surface Expression of Lysosomal Membrane Glycoproteins in Sublines of a Human Colon Cancer Exhibiting Distinct Metastatic Potentials*, J. Biol. Chem. 267, 5700-5711, 1992.
Sakurama, Haruko et al., Differences in the Substrate Specificities and Active-Site Structures of Two α-L-Fucosidases (Glycoside Hydrolase Family 29) From Bacteroides Thetaiotaomicron, Bioscience Biotechnology Biochemistry, vol. 76, No. 5, May 23, 2012, pp. 1022-1024.
Salisbury et al., "Activity-based probes for proteomic profiling of histone deacetylase complexes," *Proc. Natl. Acad. Sci. USA*, Jan. 23, 2007, 104(4):1171-1176.
Salomon et al., Inhibition of the cytokine response does not protect against lethal H5N1 nfluenza infection. Proc Natl Acad Sci U S A Jul. 24,2007;104(30): 12479-81.
Sanna, Peitro et al., Directed Selection of Recombinant Human Monoclonal Antibodies to Herpes Simplex Virus Glycoproteins From Phage Display Libraries, Proc. Natl. Acad. Sci., 92:6439 (1995).
Sarkar et al., "Disaccharide uptake and priming in animal cells: inhibition of sialyl Lewis X by acetylated Galβ1→4GlcNAcβ-O-naphthalenemethanol," *Proc. Natl. Acad. Sci. USA*, Apr. 11, 1995, 92(8):3323-3327.
Sastry et al., "Cloning of the immunological repertoire in *Escherichia coli* for generation of monoclonal catalytic antibodies: construction of a heavy chain variable region-specific cDNA library," *Proc. Natl. Acad. Sci. U.S.A.*, Aug. 1989, 86(15):5728-5732.
Sauter, NK et al., Binding of Influenza Virus Hemagglutinin to Analogs of Its Cell-Surface Receptor, Sialic Acid: Analysis by Proton Nuclear Magnetic Resonance Spectroscopy and X-Ray Crystallography. Biochemistry, 31 :9609, 1992.
Sawa, M.; Hsu, T.-L.; Itoh,T.; Sugiyama, M. ; Hanson, S. R. ; Vogt, P. K.; Wong, C.-H. "Glycoproteomic probes for fluorescent imaging of fucosylated glycans in vivo." Proc. Nat. Acad. Sci. US.A., 2006, 103, 12371-12376.
Sawada, Tetsuji et al., E-Selectin Binding by Pancreatic Tumor Cells is Inhibited by Cancer Sera, Int. J. Cancer 57, 901-907, 1994.
Sawada, Ritsuko et al., Differential E-Selectin-Dependent Adhesion Efficiency in Sublines of a Human Colon Cancer Exhibiting Distinct Metastatic Potentials, J. Biol. Chem. 269, 1425-1431, 1994.
Scanlan, C. N. et al., Exploiting the defensive sugars of HIV-I for drug and vaccine design. Nature 446, 1038-1045, (2007).
Schena, M. et al., Quantitative Monitoring of Gene Expression Patterns with a Complementary DNA Microarray, Science, 1995, 270:467-70.
Schengrund et al., "Localization of sialidase in the plasma membrane of rat liver cells," *J. Biol. Chem.*, May 10, 1972, 247(9):2742-2746.

(56) References Cited

OTHER PUBLICATIONS

Schenkel-Brunner, *Human Blood Groups, Chapter 8: P System*, 1995, pp. 211-234, Springer-Verlag, Vienna.

Schier et al., "Identification of functional and structural amino-acid residues by parsimonious mutagenesis," *Gene*, Mar. 9, 1996, 169(2):147-155.

Schmitz, U. et al., Phage Display: A Molecular Tool for the Generation of Antibodies—A Review, Placenta, 21 Suppl. A:S 106 (2000).

Schneider, M.C. et al., Interactions Between Neisseria Meningitidis and the Complement System, Trends Microbial 2007, 15, 233-240.

Schroder et al., The Peptides, vol. 1, p. 76-136, 1965.

Schug, Kevin et al., "Noncovalent binding between guanidinium and anionic groups: focus on biological- and synthetic-based arginine/guanidinium interactions with phosph[on]ate and sulf[on]ate residues," Chem. Rev., Jan. 2005, 105(1):67-113.

Schweitzer, Barry et al., Multiplexed Protein Profiling on Microarrays by Rolling-Circle Amplification, Nat. Biotechnol. (2002), 20, 359-365.

Scurr, D. J. et al. Surface characterization of carbohydrate microarrays. Langmuir 26, 17143-17155, (2010).

Sell, "Cancer-associated carbohydrates identified by monoclonal antibodies," *Hum. Pathol.*, Oct. 1990, 21(10):1003-1019.

Serna, S. et al., Construction of N-Glycan Microarrays by Using Modular Synthesis and On-Chip Nanoscale Enzymatic Glycosylation. Chem. Eur. J 16, 13163-13175, (2010).

Severi et al., "Sialic acid utilization by bacterial pathogens," *Microbiology*, Sep. 2007, 153(Pt 9):2817-2822.

Seyrantepe et al., "Neu4, a novel human lysosomal lumen sialidase, confers normal phenotype to sialidosis and galactosialidosis cells," *J. Biol. Chem.*, Aug. 27, 2004, 279(35):37021-37029.

Shalaby et al., "Development of humanized bispecific antibodies reactive with cytotoxic lymphocytes and tumor cells overexpressing the HER2 protooncogene," *J. Exp. Med.*, Jan. 1, 1992, 175(1):217-225.

Sheu et al., "Surveillance for neuraminidase inhibitor resistance among human influenza A and B viruses circulating worldwide from 2004 to 2008," *Antimicrob. Agents Chemother.*, Sep. 2008, 52(9):3284-3292.

Shevinsky, LH et al., Monoclonal Antibody to Murine Embryos Defines a Stage-Specific Embryonic Antigen Expressed on Mouse Embryos and Human Teratocarinoma Cells., Cell vol. 30, Issue 3, Oct. 1982, pp. 697-705.

Shie, Jiun-Jie et al., "A concise and flexible synthesis of the potent anti-influenza agents tamiflu and tamiphosphor," Angew. Chem. Int. Ed Engl., 2008, 47(31):5788-5791.

Shie, Jiun-Jie et al., An Azido-BODIPY Probe for Glycosylation: Initiation of Strong Fluorescence Upon Triazole Formation, J. Am. Chem. Soc. 2014, 136, 9953-9961.

Shieh, Peyton et al., Fluorogenic Azidofluoresceins for Biological Imaging, J. Am. Chem. Soc. 2012, 134, 17428-17431.

Shields et al., "High resolution mapping of the binding site on human IgG1 for FcγRI, FcγRII, FcγRIII, and FcRn and design of IgG1 variants with improved binding to the FcγR," *J. Biol. Chem.*, Mar. 2, 2001, 276(9):6591-6604.

Shields et al., "Lack of fucose on human IgG1 N-linked oligosaccharide improves binding to human FcγRIII antibody-dependent cellular toxicity," *J. Biol. Chem.*, Jul. 26, 2002, 277(30):26733-26740.

Shinkawa et al., "The absence of fucose but not the presence of galactose or bisecting N-acetylglucosamine of human IgG1 complex-type oligosaccharides shows the critical role of enhancing antibody-dependent cellular cytotoxicity," *J. Biol. Chem.*, Jan. 31, 2003, 278(5):3466-3473.

Shivatare, S. S. et al. Efficient convergent synthesis of bi-, tri-, and tetra-antennary complex type N-glycans and their HIV-1 antigenicity. J. Am. Chem. Soc. 135, 15382-15391, (2013).

Shivatare, S. S. et al., Modular Synthesis of N-Glycans and Arrays for the Hetero-Ligand Binding Analysis of HIV Antibodies, Nature Chemistry, Mar. 7, 2016, vol. 8(4), p. 338-346.

Shriver, Zachary et al., Glycomics: a Pathway to a Class of New and Improved Therapeutics, Nat Rev Drug Disc, 2004, 3, 863-873.

Sidhu et al., "Phage-displayed antibody libraries of synthetic heavy chain complementarity determining regions," *J. Mol. Biol.*, Apr. 23, 2004, 338(2):299-310.

Siebenlist et al., "*E. coli* RNA polymerase interacts homologously with two different promoters," *Cell*, Jun. 1980, 20(2):269-281.

Sieber et al., "Proteomic profiling of metalloprotease activities with cocktails of active-site probes," *Nat. Chem. Biol.*, May 2006, 2(5):274-281.

Simmons et al., "Expression of full-length immunoglobulins in *Escherichia coli*: Rapid and efficient production of aglycosylated antibodies," *J. Immunol. Methods*, May 1, 2002, 263(1-2):133-147.

Sims et al., "A humanized CD18 antibody can block function without cell destruction," *J. Immunol.*, Aug. 15, 1993, 151(4):2296-2308.

Sivakumar, Krishnamoorthy et al., "A fluorogenic 1,3-dipolar cycloaddition reaction of 3-azidocoumarins and acetylenes." Org. Lett. 2004,24, 4603-4606.

Skehel, John et al., Receptor Binding and Membrane Fusion in Virus Entry: The Influenza Hemagglutinin, Ann. Rev Biochem, 69:531, 2000.

Skerra, "Bacterial expression of immunoglobulin fragments," *Curr. Opinion in Immunol.*, Apr. 1993, 5(2):256-262.

Slamon DJ, et al., Human breast cancer: correlation of relapse and survival with amplification of the HER-2/neu oncogene, *Science*. Jan. 9, 1987; 235(4785):177-82.

Sletten et al., "Bioorthogonal Chemistry: Fishing for Selectivity in a Sea of Functionality," *Angew. Che. Int. Ed. Engl.*, Aug. 27, 2009, 48(38):6974-6998.

Smith RA et al., "The active form of tumor necrosis factor is a trimer" *J Biol Chem*. May 25, 1987;262(15):6951-4.

Smyth MJ, et al., "CD4+CD25+ T regulatory cells suppress NK cell-mediated immunotherapy of cancer" *J Immunol*. Feb. 1, 2006;176(3):1582-7.

Sok, Devin et al., SnapShot: Broadly Neutralizing Antibodies. Cell 155, 728-728, (2013).

Solomons, G. and Fryhle, C., Chapter 5 Titled, Stereochemistry: Chiral Molecules, p. 184-228, in "Organic Chemistry," 7th Edition, Wiley, Jun. 18, 2001.

Soriano del Amo, David et al. Chemoenzymatic synthesis of the sialyl Lewis X glycan and its derivatives. Carbohydr. Res. 345, 1107-13, (2010).

Spinosa, Maria Rita et al., The Neisseria Meningitidis Capsule is Important for Intracellular Survival in Huamn Cells, Infect Immun 2001, 75, 3594-3603.

Srinivasan, Quantitative et al., Biochemical Rationale for Differences in Transmissibility of 1918 Pandemic Influenza A Viruses, Proc. Natl. Acad. Sci., 105, 2800-2805, 2008.

Stein, K.E. et al., The Immune Response to an Isomaltohexosyl-Protein Conjugate, a Thymus-Dependent Analogue of Alpha(1 Replaced by 6) Dextran., J Immunol 1982, 128, 1350-1354.

Stein, K.E., Thymus-Independent and Thymus-Dependent Responses to Polysaccharide Antigens, J Infect Dis 1992, 165 Suppl 1, S49-52.

Stephens, David, Conquering the Meningococcus, FEALS Microbial Rev 2007, 31, 3-14.

Stephens, D.S. et al., Epidemic Meningitis, Meningococcaemia, and Neisseria Meningitidis, Lancet 2007, 369, 2196-2210.

Stephenson et al., "Neuraminidase inhibitor resistance after oseltamivir treatment of acute influenza A and B in children," Clin. Infect. Dis., Feb. 15, 2009, 48(4):389-396.

Stevanovic, Stefan, Identification of Tumour-Associated T-Cell Epitopes for Vaccine Development, Nat. Rev. Cancer, 2002, 2, 514-520.

Stevens, James et al., Structure of the Uncleaved Human H1 Hemagglutinin From the Extinct 1918 Influenza Virus, Science, 303:1866, 2004.

Stevens, James et al., Structure and Receptor Specificity of the Hemagglutinin From an H5N1 Influenza Virus, Science, 312:404, 2006.

(56) References Cited

OTHER PUBLICATIONS

Stickings, P. et al., nfect. Immun 2008, 76, 1766.
Stockmann, H. et al., Development and Evaluation of New Cyclootynes for Cell Surface Glycan Imaging in Cancer Cells, J. Chem. Sci. 2011, 2, 932-936.
Streicher et al., "Building a successful structural motif into sialylmimetics-cyclohexenephosphonate monoesters as pseudo-sialosides with promising inhibitory properties," Bioorg. Med Chem., Feb. 15, 2006, 14(4):1047-1057.
Stubbs et al., "Synthesis and use of mechanism-based protein-profiling probes for retaining β-D-glucosaminidases facilitate identification of *Pseudomonas aeruginosa* NagZ," *J. Am. Chem. Soc.*, Jan. 9, 2008, 130(1):327-335.
Su, G. Hahner, W. Zhou "Investigation of the pore formation in anodic aluminum oxide" J Mater. Chem. 2008, 18 5787-5795.
Sun, B., Srinibasan, B., Huang, X., Pre-activation-based one-pot synthesis of an alpha-(2,3)-sialylated core-fucosylated complex type bi-antennary N-glycan dodecasaccharide. Chem. Eur. J 14 (23), 7072-81, (2008).
Supplementary European Search Report in European Application No. EP 13775664.9, dated Oct. 27, 2015, in 7 pages.
Suresh et al., "Bispecific monoclonal antibodies from hybrid hybridomas," *Methods in Enzymology*, 1986, 121:210-228.
Sutton, VR et al., Bc1-2 Prevents Apoptosis Induced by Perforin and Granzyme B, But Not That Mediated by Whole Cytotoxic Lymphocytes, J of Immunology 1997, 158(12), 5783.
Suzuki E, et al., "A nonfucosylated anti-HER2 antibody augments antibody-dependent cellular cytotoxicity in breast cancer patients" *Clin Cancer Res.* Mar. 15, 2007;13(6):1875-82.
Svennerholm et al., "Human brain gangliosides: Developmental changes from early fetal stage to advanced age," *Biochim. Biophys. Acta*, Sep. 25, 1989, 1005(2):109-117.
Syrigos et al., "Antibody directed enzyme prodrug therapy (ADEPT): a review of the experimental and clinical considerations," *Anticancer Research*, Jan.-Feb. 1999, 19(1A):605-614.
Tahir et al., "Loss of IFN-γ production by invariant NK T cells in advanced cancer," *J. Immunol.*, Oct. 1, 2001, 167(7):4046-4050.
Takakura, Yoshimitsu et al., Molecular cloning, expression and properties of an alpha/beta-Galactoside alpha 2,3-sialyltransferase from *Vibrio* sp. JT-FAJ-16. J. Biochem. 142, 403-412, (2007).
Takano, Ryo et al., Sialylation and Malignant Potential in Tumour Cell Glycosylation Mutants, Glycobiology 4, 665-674 (1994).
Takeda et al., "Construction of chimaeric processed immunoglobulin genes containing mouse variable and human constant region sequences," *Nature*, Apr. 4-10, 1985, 314(6010):452-454.
Taki, Takao et al., Glycolipids of Metastatic Tissue in Liver From Colon Cancer: Appearance of Sialylated Lex and Lex Lipids, J. Biochem. 103, 998-1003, 1998.
Talmadge et al., Murine models to evaluate novel and conventional therapeutic strategies for cancer, Am. J. Pathol, 170(3): 793-804 (2007).
Tanaka, Hiroshi et al., An Efficient Convergent Synthesis of GP1c Ganglioside Epitope, J Am Chem Soc. 2008, 130, 17244.
Tanaka, Katsunori et al., Synthesis of a Sialic Acid Containing Complex-Type N-Glycan on a Solid Support, Chemistry—an Asian Journal, 2009, vol. 4 (4), p. 574-580.
Taton, T. Andrew et al., Scanometric DNA Array Detection with Nanoparticle Probes, Science 289 (2000) 1757-1760.
Taton, T. Andrew et al., Two-Color Labeling of Oligonucleotide Arrays Via Size-Selective Scattering of Nanoparticle Probes, J. Am. Chem. Soc. (2001), 123, 5164-5165.
Taylor-Papadimitriou et al., "Exploiting altered glycosylation patterns in cancer: Progress and challenges in diagnosis and therapy," *Trends Biotechnol.*, Jun. 1994, 12(6):227-233.
Telford et al., "The Aspergillus Fumigatus Sialidase is a 3'-Deoxy-D-galacto-2-nonulosonic Acid Hydrolase (KDNase)," The Journal of Biological Chemistry, 286(12), 10783-10792 (Mar. 25, 2011).
"The Human Protein Atlas", B3GALT5 URL:http://www.proteinatlas.org/ENSG00000183778-B3GALT5/cancer, Sep. 9, 2015.

Thorpe, (1985) "Antibody Carriers of Cytotoxic Agents in Cancer Therapy: A Review," in *Monoclonal Antibodies '84: Biological and Clinical Applications*, A. Pinchera et al. (ed.s), pp. 475-506.
Thurber, Greg et al., Antibody Tumor Penetration: Transport Opposed by Systemic and Antigen-Mediated Clearance, Adv Drug Deliv Rev, 60: 1421-1434, 2008.
Toba, et al., "Synthesis and biological evaluation of truncated α-glaactosylceramide derivatives focusing on cytokine induction profile," Bioorganic & Medicinal Chemistry 20(2012): 2850-2859.
Tomlinson et al., "The repertoire of human germline $V_H$ sequences reveals about fifty groups of $V_H$ segments with different hypervariable loops," *J. Mol. Biol.*, Oct. 5, 1992, 227(3):776-798.
Torres-Sanchez et al., "Synthesis and Biological Evaluation of Phophono Analogues of Capsular Polysaccharide Fragments From Neisseria Meningtitidis A" Chem Eur J (2007) vol. 13, pp. 6623-6635.
Toshima, K. Glycosyl fluorides in glycosidations. Carbohydr. Res. 327, 15-26 (2000).
Traunecker et al., "Bispecific single chain molecules (Janusins) target cytotoxic lymphocytes on HIV infected cells," *EMBO J.*, Dec. 1991, 10(12):3655-3659.
Traylor et al., "Gangliosides of human cerebral astrocytomas," *J. Neurochem.*, Jan. 1980, 34(1):126-131.
Trinchieri, "Interleukin-12: a proinflammatory cytokine with immunoregulatory functions that bridge innate resistance and antigen-specific adaptive immunity," *Annu. Rev. Immunol.*, 1995, 13:251-276.
Tsai et al., "Design and synthesis of activity probes for glycosidases," *Org. Lett.*, Oct. 17, 2002, 4(21):3607-3610.
Tsai, Charng-sheng et al., Development of Trifunctional Probes for Glycoproteomic Analysis, Chem. Commun. 2010, 46, 5575-5577.
Tsai, Tsung-I et al., An Effective Bacterial Ducosidase for Glycoprotein Remodeling, ACS Chemical Biology, vol. 12, No. 1, Jan. 20, 2017, pp. 63-72.
Tsai Ti, et al., "Effective sugar nucleotide regeneration for the large-scale enzymatic synthesis of Globo H and SSEA4" *J Am Chem Soc.* Oct. 2, 2013;135(39):14831-9, Epub Sep. 17, 2013.
Tseng, Susan Y. et al., Glycan Arrays on Aluminum Coated Glass Slides. Chem. Asian J, 2008, 3, 1395-1405.
Tsuji, et al., "Preparation of glycolipids and analogs as antigens for NKT cells for use in vaccines and immunotherapy," CAPLUS 149:492050 (2008).
Tsukamoto, Hiroshi et al., *Photobacterium* sp. JT-ISH-224 produces two sialyltransferases, alpha-/beta-galactoside alpha2,3-sialyltransferase and betagalactoside alpha2,6-sialyltransferase. J. Biochem. 143, 187-197, 2008.
Tumpey, Terrence et al., Characterization of the Reconstructed 1918 Spanish Influenza Pandemic Virus, Science, 310:77, 2005.
Tutt et al., "Trispecific F(ab')₃ derivatives that use cooperative signaling via the TCR/CD3 complex and CD2 to activate and redirect resting cytotoxic T cells," *J. Immunol.*, Jul. 1, 1991, 147(1):60-69.
Tyagarajan K et al., "Exoglycosidase purity and linkage specificity: assessment using oligosaccharide substrates and high-pH anion-exchange chromatography with pulsed amperometric detection" *Glycobiology*. Jan. 1996;6(1):83-93.
Tzeng, Y. L. et al, Epidemiology and Pathogenesis of Neisseria Meningitidis, Microbes Infect 2000, 2, 687-700.
Uchida, Tsuyoshi et al., Diphtheria Toxin and Related Proteins, J Biol. Chem. 218; 3838-3844 (1973).
Udommaneethanakit et al., "Dynamic behavior of avain influenza A virus neuraminidase subtype H5N1 in complex with oseltamivir, zanamivir, peramivir, and their phosphonate analogues," J Chem. Inf Model, Oct. 2009, 49(10):2323-2332.
Ulevitch, RJ et al., Receptor-Dependent Mechanisms of Cell Stimulation by Bacterial Endotoxin, 1995, Annu. Rev. Immunol., 13: 437.
Ulrich, G.; Ziessel, R.; Harriman, A. "The chemistry of fluorescent bodipy dyes: Versatility unsurpassed." Angew. Chem. Int. Ed. 2008, 47, 1184-1201.
Urlaub et al., "Isolation of Chinese hamster cell mutants deficient in dihydrofolate reductase activity." Proc. Nati. Acad. Sci. U.S.A., Jul. 1980, 77(7):4216-4220.

(56) References Cited

OTHER PUBLICATIONS

Valentine MA, et al., "Phosphorylation of the CD20 phosphoprotein in resting B lymphocytes. Regulation by protein kinase C" *J Biol Chem*. Jul. 5, 1989;264(19):11282-7.
Van Beek et al., "Increased sialic acid density in surface glycoprotein of transformed and malignant cells—a general phenomenon?" *Cancer Res*., Nov. 1973, 33(11):2913-2922.
Van der Horst et al., "Photoaffinity labeling of a bacterial sialidase with an aryl azide derivative of sialic acid," *J. Biol. Chem*., Jul. 5, 1990, 265(19), 10801-10804.
Van Hest, Jan C.M. et al., Efficient Introduction of Alkene Functionality Into Proteins in Vivo (1998) FEES Lett. 428:68.
Vaki, Ajit et al., Symbols Nomenclatures for Glycan Representation, Proteomics. Dec. 2009, 9(24): 5398-5399.
Van Meir et al., "Exciting new advances in neuro-oncology: the avenue to a cure for malignant glioma," *CA Cancer J. Clin*., May-Jun. 2010, 60(3):166-193.
Van Slambrouck et al., "Clustering of monosialyl-Gb5 initiates downstream signalling events leading to invasion of MCF-7 breast cancer cells," *Biochem. J*., Feb. 1, 2007, 401(3):689-699.
Varghese et al., Three-dimensional structure of the complex of 4-guanidino-Neu5Ac2en and nfluenza virus neuraminidase. Protein Sci. Jun. 1995;4(6):1081-7.
Varki, "Glycan-based interactions involving vertebrate sialic-acid-recognizing proteins," *Nature*, Apr. 26, 2007, 446(7139):1023-1029.
Vasella et al., "Synthesis of a phosphoric acid analogue of N-Acetyl-2,3-didehydro-2-deoxyneuraminic acid, an inhibitor of Vibrio cholerae sialidase," Helv. Chim. Acta, Mar. 13, 1991, 74(2):451-463.
Vaswani et al., "Humanized antibodies as potential therapeutic drugs," *Ann. Allergy, Asthma Immunol*., Aug. 1998, 81(2):105-116, 119.
Vavricka, Christopher et al., Influenza Neuraminidase Operates Via a Nucleophilic Mechanism and Can Be Targeted by Covalent Inhibitors, Nature Communcations, 4:1491 (2013).
Verhoeyen et al., "Reshaping human antibodies: grafting an antilysozyme activity," *Science*, Mar. 25, 1988, 239(4847):1534-1536.
Vermeer AW et al., "The thermal stability of immunoglobulin: unfolding and aggregation of a multi-domain protein" *Biophys J*. Jan. 2000;78(1):394-404.
Vinogradova et al., "Molecular mechanism of lysosomal sialidase deficiency in galactosialidosis involves its rapid degradation," *Biochem. J*., Mar. 1, 1998, 330(Pt 2.):641-650.
Vippagunta, Sudha et al., Crystalline Solids, Advanced Drug Delivery Reviews 48, 3-26 (2001).
Virji, Mumtaz et al., Pathogenic Neisseriae: Surface Modulation, Pathogenesis and Infection Control, Nat Rev, Microbiol 2009, 7, 274-286.
Vitetta, ES et al., Redesigning Nature's Poisons to Create Anti-Tumor Reagents, Science 23(8): 1098 (1987).
Vocadlo et al., "A strategy for functional proteomic analysis of glycosidase activity from cell lysates," *Angew. Chem. Int. Ed. Engl*., Oct. 11, 2004, 43(40):5338-5342.
Von Itzstein et al., "Rational design of potent sialidase-based inhibitors of influenza virus replication," Nature, Jun. 3, 1993, 363(6428):418-423.
Voskoglou-Nomikos, Clinical predictive value of the in vitro cell line, human xenograft, and mouse allograft preclinical cancer models, Clin Can Res, 9: 4227-4239 (2003).
Wada et al., "A crucial role of plasma membrane-associated sialidase in the survival of human cancer cells," *Oncogene*, Apr. 12, 2007, 26(17):2483-2490.
Wagner, R et al., "Functional balance between haemagglutinin and neuraminidase in influenza virus infections," Rev. Med Viral., May-Jun. 2002, 12(3): 159-166.
Walls et al., "Activity-based protein profiling of protein tyrosine phosphatases," *Methods Mol. Biol*., 2009, 519:417-429.
Walker, L. M. et al. Broad neutralization coverage of HIV by multiple highly potent antibodies. Nature 477, 466-470, (2011).

Wang, Chao et al., Tuning the Optical Properties of BODIPY Dye Through Cu(I) Catalyzed Azide-Alkyne Cycloaddition (CuAAC) Reaction, Sci. China Chemistry 2012, 55, 125-130.
Wang, Zhen et al., Multi-Component One-Pot Synthesis of the Tumor-Associated Carbohydrate Antigen Globo-H Based on Preactivation of Thioglycosyl Donors, J Org. Chem. 2007, 72, 6409.
Wang et al., "Glycan microarray of Globo H and related structures for quantitative analysis of breast cancer," *Proc. Natl. Acad. Sci. U.S.A*., Aug. 19, 2008, 105(33):11661-11666.
Wang et al., "A continuous colorimetric assay for rhinovirus-14 3C protease using peptide p-nitroanilides as substrates," Anal. Biochem., Oct. 15, 1997, 252(2):238-245.
Wang et al., "Synthesis of Neisseria Meningitidis Serogroup W135 Capsular Oligosaccharides for Immunogenicity Comparison and Vaccine Development" Angew Chem Int Ed (2013) vol. 52, pp. 9157-9161.
Wang, Michael et al., "Mechanism by which mutations at his274 alter sensitivity of influenza A virus NI neuraminidase to oseltamivir carboxylate and zanamivir," Antimicrob. Agents Chemother., Dec. 2002, 46(12):3809-3816.
Wang, D., Liu, S., Trummer, B. J., Deng, C. & Wang, A. Carbohydrate microarrays for the recognition of cross-reactive molecular markers of microbes and host cells. Nat. Biotechnol. 20, 275-281, (2002).
Wang et al., Computational Studies of H5N1 Influenza Virus Resistance to Oseltamivir. Protein Sci. 2009, 18(4): 707-715; p. 713.
Wang, L. X. Carbohydrate-based vaccines against HIV/AIDS. Acs Sym. Ser. 932, 133-160 (2006).
Wang, L. X. Synthetic carbohydrate antigens for HIV vaccine design. Curr. Opin. Chem. Biol. 17, 997-1005, (2013).
Wang, W. et al. A systematic study of the N-glycosylation sites of HIV-I envelope protein on infectivity and antibody-mediated neutralization. Retrovirology, 10, 14, (2014).
Wang, Zhen et al. A general strategy for the chemoenzymatic synthesis of asymmetrically branched N-glycans. Science 341, 379-383, (2013).
Ward et al., "Binding activities of a repertoire of single immunoglobulin variable domains secreted from *Escherichia coli,*" *Nature*, Oct. 12, 1989, 341(6242):544-546.
Waterhouse et al., "Combinatorial infection and in vivo recombination: a strategy for making large phage antibody repertoires," *Nuc. Acids Res*., May 11, 1993, 21(9):2265-2266.
Watts et al., "The Synthesis of Some Mechanistic Probes for Sialic Acid Processing Enzymes and the Labeling of a Sialidase from Trypanosoma Rangeli," Canadian Journal of Chemistry, 82(11), 1581-1588 (2004).
Watts et al., "*Trypanosoma cruzi* trans-sialidase operates through a covalent sialyl-enzyme intermediate: tyrosine is the catalytic nucleophile," *J. Am. Chem. Soc*., Jun. 25, 2003, 125(25):7532-7533.
Weibel, Robert et al., Tumor-Associated Membrane Sialoglycoprotein on Human Small Cell Lung Carcinoma Identified by the IgG2a Monoclonal Antibody SWA20, (1988) Cancer Res. 48, 4318-4323.
Wen, Wen Hsien et al., "Synergistic effect of zanamivir-porphyrin conjugates on inhibition of neuraminidase and inactivation of influenza virus," J Med Chem., Aug. 13, 2009, 52(15):4903-4910.
White, Clinton et al., "A sialic acid-derived phosphonate analog inhibits different strains of influenza virus neuraminidase with different efficiencies," J Mol. Biol., Feb. 3, 1995, 245(5):623-634.
Wikstrand et al., "Monoclonal antibody therapy of human gliomas: Current status and future approaches," *Cancer Metastasis Rev*., 1999, 18(4):451-464.
Wilen et al., "Strategies in optical resolutions," Tetrahedron, 1977, 33(21):2725-2736.
Williams et al., "Cloning and sequencing of human immunoglobulin V lambda gene segments." *Eur. J. Immunol*., Jul. 1993, 23(7):1456-1461.
Wiltshire, S. et al. Proc. Natl. Acad. Sci. (2000) 97, 10113-10119.
Winter et al., "Making antibodies by phage display technology," *Annu. Rev. Immunol*., 1994, 12:433-455.
Wiseman, GA et al., Phase I/II 90Y-Zevalin (yttrium-90 Ibritumomab Tiuxetan, IDEC-Y2B8) Radioimmunotherapy Dosimetry Results in Relapsed or Refractory Non-Hodgkin's Lymphoma, Eur Jour Nucl Med 27(7): 766-77 (2000).

(56) References Cited

OTHER PUBLICATIONS

Wiseman, Gregory et al., Ibritumomab Tiuxetan Radioimmunotherapy for Patients with Relapsed or Refractory Non-Hodgkin Lymphoma and Mild Thrombocytopenia: a Phase II Multicenter Trial, Blood 99(12): 4336-42 (2002).
Witte et al., "Ultrasensitive in situ visualization of active glucocerebrosidase molecules," Nat. Chem. Biol., Dec. 2010, 6(12):907-913.
Witzig, Thomas et al., Randomized Controlled Trial of Yttrium-90-Labeled Ibritumomab Tiuxetan Radioimmunotherpay Versus Rituximab Immunotherapy for Patients with Relapsed or Refractory Low-Grade, Follicular, or Transformed B-Cell Non-Hodgkin's Lymphoma, J Clin Oncol 20(10):2453-63 (2002).
Witzig, Thomas et al., Treatment with Ibritumomab Tiuxetan Radioimmunotherapy in Patients with Rituximab-Refractory Follicular Non-Hodgkin's Lymphoma, J Clin Oncol 20(15):3262-69 (2002).
Wong et al., α-Galactosyl Ceramide Analogs and Their use as Therapeutic, 2010:50988, 2 Pages.
Woo et al. Cytokine profiles induced by the novel swine-origin influenza A/HINI virus: mplications for treatment strategies. J Infect Dis. Feb. 1, 2010;201(3):346-53.
Woof et al., "Human antibody-Fc receptor interactions illuminated by crystal structures," Nat. Rev. Immunol., Feb. 2004, 4(2):89-99.
Woyke, Tanja et al., Effect of Auristatin PHE on Microtubule Integrity and Nuclear Localization in Cryptococcus Neoformans, Antimicrob. Agents and Chemother. 45(12): 3580-3584 (2001).
Wright et al. Antibody variable region glycosylation: biochemical and clinical effects, Springer Semin Immunopathology, 15:259-273 (1993).
Wu et al., "Avidity of CD1d-ligand-receptor ternary complex contributes to T-helper 1 (Th1) polarization and anticancer efficacy," Proc. Natl. Acad. Sci. USA, Oct. 18, 2011, 108(42):17275-17280.
Wu, Xueling et al. Rational design of envelope identifies broadly neutralizing human monoclonal antibodies to HIV-I. Science 329, 856-861, (2010).
Wu, Liangxing et al., Fluorescent Cassettes for Monitoring Three-Component Interactions in Vitro and in Living Cells, Journal of the American Chemical Society (2009), 131(26), 9156-9157.
Wu et al., "Catalytic azide-alkyne cycloaddition: reactivity and applications," Aldrichimica Acta, 2007, 40(1):7-17.
Xie, F.; Sivakumar, K.; Zeng, Q. B.; Bruckman, M. A.; Hodges, B.; Wang, Q. "A fluorogenic 'click' reaction of azidoanthracene derivatives." Tetrahedron 2008, 64, 2906-2914.
Yamaguchi, Kazunori et al., "Evidence for mitochondrial localization of a novel human sialidase (NEU4)," Biochem. J., Aug. 15, 2005, 390(Pt 1):85-93.
Yamane-Ohnuki, Naoko et al., Production of Therapeutic Antibodies with Controlled Fucosylation, mAbs 2009, 1;3:230-236.
Yamashita et al., CS-8958, a prodrug of the new neuraminidase inhibitor R-125489, shows ong-acting anti-influenza virus activity. Antimicrob Agents Chemother. Jan. 2009;53(1):186-92.
Yamashita, Yoshito et al., Alterations in Gastric Mucin with Malignant Transformation: Novel Pathway for Mucin Synthesis, (1995) J. Natl. Cancer Inst. 87, 441-446.
Yang, JM et al., Alterations of )-Glycan Biosynthesis in Human Colon Cancer Tissues, (1994) Glycobiology 4, 873-884.
Yaniv, Nature 297: 17-18, 1982.
Yansura et al., "Nucleotide sequence selection for increased expression of heterologous genes in Escherichia coli," Methods: A Companion to Methods in Enzymol., Aug. 1992, 4(2):151-158.
Yates AJ et al., Brain Tumors in Childhood. Childs Brain 5(1), 31-39 (1979).
Ye et al., "Stage-specific embryonic antigen 4 expression in epithelial ovarian carcinoma," Int. J. Gynecol. Cancer, Aug. 2010, 20(6):958-964.
Yelton et al., "Affinity maturation of the BR96 anti-carcinoma antibody by codon-based mutagenesis." J. Immunol., Aug. 15, 1995, 155(4):1994-2004.
Yguerabide, Juan et al., Light-Scattering Submicroscopic Particles as Highly Fluorescent Analogs and Their Use as Tracer Labels in Clinical and Biological Applications: II. Experimental Characterization, Anal. Biochem. (1998), 262, 157-176.
Ying et al., One-bead-one-inhibitor-one-substrate screening of neuraminidase activity. Chembiochem. Oct. 2005;6(10):1857-65.
Yoshida M, et al. Glycoconjugate J. 1993, 10, 324.
Yoshimoto et al., "CD4$^{pos}$, NK1.1$^{pos}$ T cells promptly produce interleukin 4 in response to in vivo challenge with anti-CD3," J. Exp. Med., Apr. 1, 1994, 179(4):1285-1295.
Yu et al., "Anti-GD2 antibody with GM-CSF, interleukin-2, and isotretinoin for neuroblastoma," N. Engl. J. Med., Sep. 30, 2010, 363(14):1324-1334.
Yuen et al., Human infection by avian influenza A H5N1. Hong Kong Med J. Jun. 2005;1 1(3):189-99.
Zapata et al., "Engineering linear F(ab')$_2$ fragments for efficient production in Escherichia coli and enhanced antiproliferative activity," Protein Eng., Oct. 1995, 8(10):1057-1062.
Zarei et al., "Separation and identification of GM1b pathway Neu5Ac- and Neu5Gc gangliosides by on-line nanoHPLC-QToF MS and tandem MS: toward glycolipidomics screening of animal cell lines," Glycobiology, Jan. 2010, 20(1):118-126.
Zhang et al., "New cerebrosides from Acanthopanax gracilistylus," CAPLUS 156:225776 (2011).
Zhang et al., "Selection of tumor antigens as targets for immune attack using immunohistochemistry: I. Focus on gangliosides," Int. J. Cancer, Sep. 26, 1997, 73(1):42-49.
Zhang, Hai-Long et al., A Novel Combined Conjugate Vaccine: Enhanced Immunogenicity of bFGF with CRM197 as a Carrier Protein, Molecular Medicine Reports, 4, 857-863, 2011.
Zheng et al., Delayed antiviral plus immunomodular treatment still reduces mortality in mice infected by high inoculum of influenza A/H5N1 virus. Proc Natl Acad Sci U S A. Jun. 10, 2008;105(23):8091-6.
Zhou et al., A fluorogenic probe for the copper(I)-catalyzed azide-alkyne ligation reaction: modulation of the fluorescence emission via $^3(n,\pi)$-$^1(\pi,\pi^*)$ inversion, J. Am. Chem. Soc., Jul. 28, 2004, 126(29):8862-8863.
Zhu, X et al., Mass spectrometric characterization of the glycosylation pattern of HIV-gp120 expressed in CHO cells. Biochemistry 39, 11194-11204 (2000).
Zimmermann et al., Multi-target therapeutics: when the whole is greater than the sum of the parts. Drug Discov Today. Jan. 2007;12(1-2):34-42. Epub Nov. 28, 2006.
Zou, et al., Chemoenzymatic synthesis and Fc gamma receptor binding of homogeneous glycoforms of antibody Fc to FcIIIa receptor. J Am Chem Soc. 2011, 133(46):18975-91.
Herter et al "Glycoengineering of therapeutic antibodies enhances monocyte/macrophage-mediated phagocytosis and cytotoxicity" J Immunol. Mar. 1, 2014, vol. 192 No. 5, pp. 2252-2260.
Jez et al "Significant Impact of Single N-Glycan Residues on the Biological Activity of Fc-based Antibody-like Fragments" Journal of Biological Chemistry Jul. 13, 2012, vol. 287 No. 29, pp. 24313-24319.
Junttila et al "Superior in vivo efficacy of afucosylated trastuzumab in the treatment of HER2-amplified breast cancer" Cancer Res. 2010, vol. 70 No. 11, pp. 4481-4489.
Komarova et al "Plant-Made Trastuzumab (Herceptin) Inhibits HER2/Neu+ Cell Proliferation and Retards Tumor Growth" PLOS ONE 2011,vol. 6 No. 3, p. e17541.
McConville, Malcolm J., and M. A. Ferguson. "The structure, biosynthesis and function of glycosylated phosphatidylinositols in the parasitic protozoa and higher eukaryotes." Biochemical Journal 294.Pt 2 (1993): 305.
Ochiai et al "Expeditious Chemoenzymatic Synthesis of Homogeneous N-Glycoproteins Carrying Defined Oligosaccharide Ligands" J. Am. Chem. Soc. 2008, vol. 130 No. 41, pp. 13790-13803.
Office Action dated Aug. 29, 2017, from corresponding Japanese Patent Application No. 2016-169045, 5 total pages.
Tebbey et al "Importance of manufacturing consistency of the glycosylated monoclonal antibody adalimumab (Humira®) and potential impact on the clinical use of biosimilars" GABI Journal 2016, vol. 5 Issue 2, pp. 70-73.
Wiseman, Gregory A., et al. "Radiation dosimetry results and safety correlations from (90) Y-ibritumomab tiuxetan radioim-

(56) References Cited

OTHER PUBLICATIONS munotherapy for relapsed or refractory non-Hodgkin's lymphoma: Combined data from 4 clinical trials" The Journal of Nuclear Medicine 44.3 (2003): 465-474.

Zhang et al "Glycoengineered Pichia produced anti-HER2 is comparable to trastuzumab in preclinical study" mAbs May-Jun. 1011, vol. 3 No. 3, pp. 289-298.

Hodoniczky J, Zheng YZ, James DC. "Control of recombinant monoclonal antibody effector functions by Fc N-glycan remodeling in vitro" Biotechnology Progress. 2005;21(6):1644-1652.

Komarova TV, et al. "Trastuzumab and pertuzumab plant biosimilars: Modification of Asn297-linked glycan of the mAbs produced in a plant with fucosyltransferase and xylosyltransferase gene knockouts" Biochemistry (Moscow). Apr. 1, 2017;82(4):510-520.

Liu L. "Antibody glycosylation and its impact on the pharmacokinetics and pharmacodynamics of monoclonal antibodies and Fc-fusion proteins" Journal of Pharmaceutical Sciences. Jun. 2015;104(6):1866-1884.

Raju TS. "Terminal sugars of Fc glycans influence antibody effector functions of IgGs" Current Opinion in Immunology. Aug. 1, 2008;20(4):471-478.

Zhou Q, et al. "Site-specific antibody—drug conjugation through glycoengineering" Bioconjugate Chemistry. Feb. 28, 2014;25(3):510-520.

\* cited by examiner

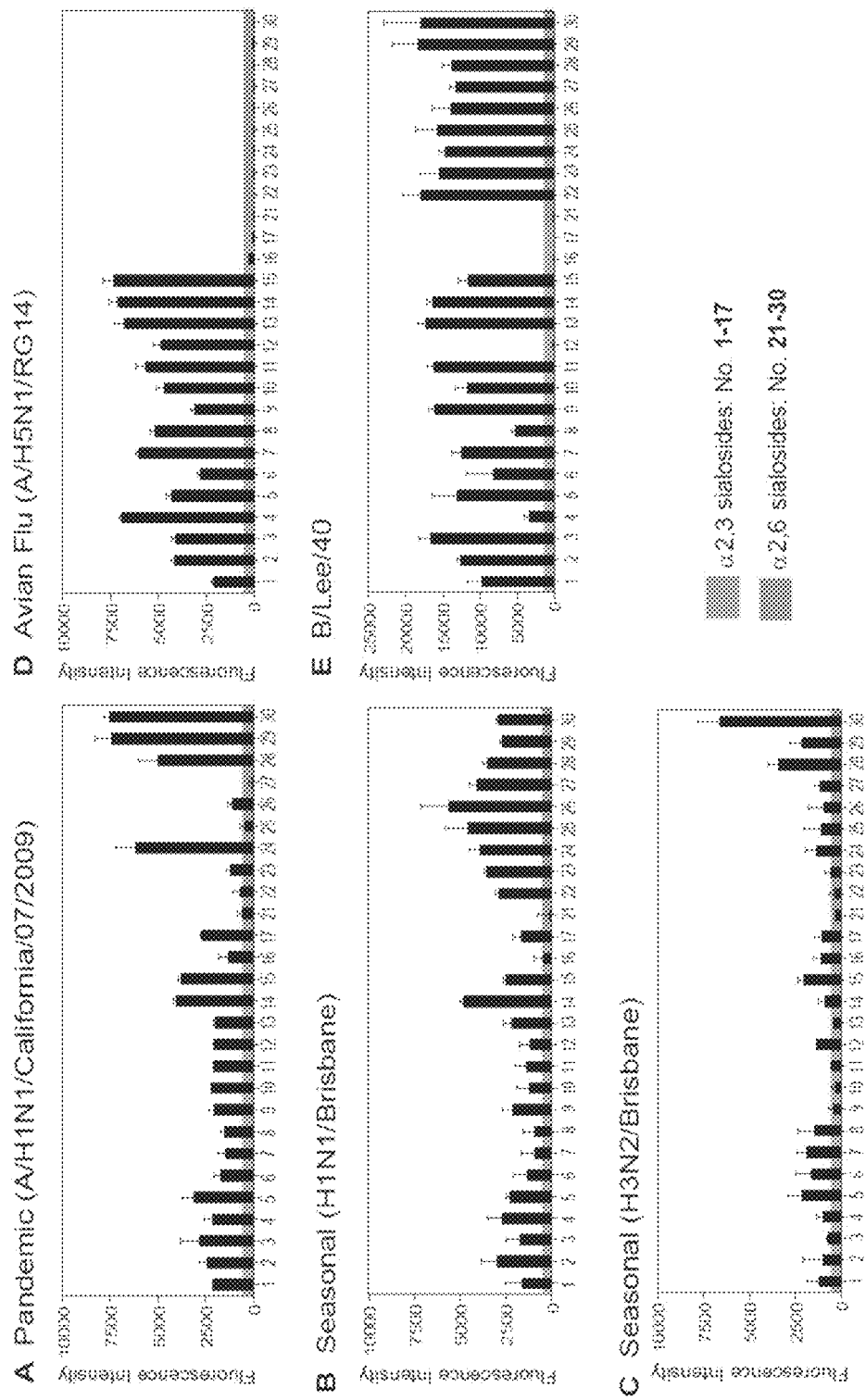

GLYCAN ARRAYS FOR HIGH THROUGHPUT SCREENING OF VIRUSES

This application is a U.S. National Stage entry of International Application No. PCT/US2011/032192 filed Apr. 12, 2011 which application claims priority under the Paris Convention to U.S. Provisional Patent Application Ser. No. 61/323,300, filed Apr. 12, 2010, the contents of which are incorporated herein by reference.

TECHNICAL FIELD OF THE INVENTION

The present invention relates to classification of influenza virus subtypes. Specifically, the invention relates to glycan arrays which can detect and distinguish between influenza virus subtypes. More specifically, the invention relates to methods for detecting influenza virus subtypes using nanoparticle-based detection methods. The invention relates to detector molecules comprising noble metals conjugated to (a) phage display particles expressing antibodies against hemagglutinin and (b) neuraminidase binding agents.

BACKGROUND OF THE INVENTION

Influenza has a long history of pandemics, epidemics, resurgences and outbreaks. Avian influenza, including the H5N1 strain, is a highly contagious and potentially fatal pathogen, but it currently has only a limited ability to infect humans. However, avian flu viruses have historically observed to accumulate mutations that alter its host specificity and allow it to readily infect humans. In fact, two of the major flu pandemics of the last century originated from avian flu viruses that changed their genetic makeup to allow human infection. The emergence of new influenza A (H1N1) virus (henceforth: influenza $A(H1N1)_v$ virus, where v stands for variant, according to nomenclature agreed by the World Health Organization Global Influenza Surveillance Network—WHO GISN) in humans has led to the requirement for sensitive and specific assays for the differential diagnosis and confirmation of influenza A(H1N1)v virus infections, necessary to guide public health actions.

Triple-reassortant swine influenza viruses, which contain genes from human, swine, and avian influenza A viruses, have been identified in swine in the United States since 1998. In April, 2009, the U.S. Centers for Disease Control and Prevention identified novel swine-origin influenza A virus which contains a unique combination of gene segments from both North American and Eurasian swine lineages, colloquially called swine flu. Co-circulation of current seasonal human H1N1, H3N2, and Swine-Origin Influenza (S-OIV) A (H1N1) Viruses in the upcoming flu seasons poses a challenge for sub-typing individual strains and potential reassortants. The more complicated, and perhaps dangerous, scenario is the reassortment of Swine-Origin Influenza A with highly pathogenic avian H5N1 or with other serotypes.

Traditional methods for influenza detection and subtype identification are based on virus isolation in tissue culture. Methods for subtyping of the virus require expansion of viruses in embryonated eggs, followed by subtyping with serological methods (HI tests). This procedure might take a week and considerable effort. Although virus isolation has long served as the standard for the diagnosis of influenza virus, the approach alone is inefficient when worldwide outbreaks occur as it is less sensitive, time-consuming, and requires considerable technical expertise. The rapid shell vial culture assay, although more rapid than the standard tissue culture based method, the time to completion is still more than 24 h. Currently, more rapid methods with higher sensitivity and specificity have been developed to identify different subtypes of influenza virus for humans and for poultry; the serological method include immunodiffusion test, counter-Immune-electrophoresis, latex agglutination test and immunity fluorescence (IF) enzyme-linked immunosorbant assay (ELISA) and molecular biology methods include RT-PCR, nested RTPCR, rRT-PCR, nucleic acid sequence-based amplification, loop-mediated isothermal amplification, and DNA microarrays are not suitable for on-site use in field investigations or in clinical practice due to constraints such as test accessibility, and requirements for highly trained personnel, time-intensive procedures, appropriate containment laboratory facilities and elaborate instrumentation.

Limitations of most of the conventional diagnostic methods are lack of accuracy, sensitivity and delay in getting results. Importantly, the current standard for influenza subtype identification relies on either a polymerase chain reaction test or culture approach, neither of which is a quick (or inexpensive) test. The current crop of quick test products on the market is only capable, due to limitations in their technology platform, of providing a yes/no answer to the presence of influenza. While swine-origin influenza virus (S-OIV; National Virus Reference Laboratory, NVRL, Dublin) real time PCR detection is available, it may not be applicable for more-complex reassortant strains. Available real-time PCR assays (HPA A(H1)v, CDC A (H1)v, HPA A(N1)v and NVRL S-OIV assays are suitable as first-line tests but accurate assessment requires concurrent use of primary diagnostic and confirmatory assays (Ellis J., et al. Euro Surveill. 2009; 14(22):pii=19230). Further, these methods require relatively sophisticated laboratories, which are sometimes unavailable or inconvenient for clinical application.

Glycans are typically the first and potentially the most important interface between cells and their environment. As vital constituents of all living systems, glycans are involved in recognition, adherence, motility and signaling processes. For example, all cells in living organisms, and viruses, are coated with diverse types of glycans; glycosylation is a form of post or co-translational modification occurring in all living organisms; and altered glycosylation is an indication of an early and possibly critical point in development of human pathologies. (Hirabayashi, J. 2003, Trends in Biotechnology 21 (4): 141-143; Hakomori, S-I. Tumor-associated carbohydrate antigens defining tumor malignancy: Basis for development of and cancer vaccines; in The Molecular Immunology of Complex Carbohydrates-2 (Albert M Wu, ed., Kluwer Academic/Plenum, 2001). These cell-identifying glycosylated molecules include glycoproteins and glycolipids and are specifically recognized by various glycan-recognition proteins. Carbohydrates are involved in inflammation, cell-cell interactions, signal transduction, fertility, bacteria-host interactions, viral entry, cell differentiation, cell adhesion, immune response, trafficking, and tumor cell metastasis.

Carbohydrates can also be expressed on the outer surface of a majority of viral, bacterial, protozoan, and fungal pathogens. The structural expression of carbohydrates can be pathogen-specific, making carbohydrates an important molecular target for pathogen recognition and/or infectious diseases diagnosis. Glycans, chains of sugars that often form complex branched structures on proteins or lipids, are major components of the outermost surface of many viruses. Receptor specificity for the influenza virus is usually controlled by the glycoprotein HA on the virus surface. Features of the differential binding among influenza virus suggest new flu as an intermediary genetic mixing vessel and facilitate a development of diagnostics. This pathogen specific expression of carbohydrates also can aid in vaccine development. Most interactions of virus with their hosts are influenced to an important degree by the pattern of glycans and glycan-binding receptors that each expresses. This holds true at all stages of infection, from initial colonization of host epithelial surfaces, to tissue spread, to the induction of host-cell injury are dominated by glycans (See FIG. 2). The two major surfaces proteins of the virus are hemagglutinin (HA) and neuraminidase (NA). The HA and NA are grouped into 16 and 9 subtypes, respectively, both have high sequence variability even within subtypes and thus provide an effective means of monitoring changes that might occur in a virus. The HA protein protrudes from the surface of the virus and allows it to attach to a cell to begin the infection cascade. The NA protein is also located on the surface of the virus and allows the release of new particles within the infected cell by cleaving the sialic acid moiety of cellular receptors.

The development of nucleotide and protein microarrays has revolutionized genomic, gene expression and proteomic research. ((Schena, M. et al. Science, 1995, 270:467-70; MacBeath, G. and Schreiber, S. L. 2000, Science, 289, 1760-1763). One feature of the post-genomic period is the exploration of biophysical, biochemical, and immunological properties of carbohydrate-carbohydrate and carbohydrate-protein interactions. Thus, a method is needed to study protein-carbohydrate interactions and to better understand these important biological processes.

Glycomics, the comprehensive study of glycomes, focuses on the interactions of carbohydrates with other biological processes. Carbohydrate microarrays are a platform for glycomic studies probing the interactions of carbohydrates with other biopolymers and biomaterials, in a versatile, rapid, and efficient manner. One particular advantage of the carbohydrate microarray is that a glycomic analysis requires only picomoles of a material and permits typically hundreds of interactions to be screened on a single microarray. The miniaturized array methodology is particularly well suited for investigations in the field of glycomics, since biological amplification strategies, such as the Polymerase Chain Reaction (PCR) or cloning, do not exist to produce usable quantities of complex oligosaccharides. Presenting carbohydrates in a microarray format can be an efficient way to monitor the multiple binding events of an analyte, such as, a protein interacting with one or more carbohydrates immobilized on a microarray surface.

The development of glycan microarrays has been very slow for a number of reasons. First, it is difficult to immobilize a library of chemically and structurally diverse glycans on arrays, beads or the like. Second, glycans are not readily amenable to analysis by many of the currently available molecular techniques (such as rapid sequencing and in vitro synthesis) that are routinely applied to nucleic acids and proteins. methods of preparing glycan arrays have been described in PCT/US2005/007370 filed Mar. 7, 2005 titled "High Throughput Glycan Microarrays" (Blixt), and U.S. Pat. App. Pub. No. 20080220988 (Zhou).

Microarray signals are detected by many technologies. Fluorescent labeling and detection is the most popular technique used to identify hybridization signals because it is sensitive and much easier and safer to handle than radioactive labeling methods (Parrish, M. L. et al. *J. Neurosci. Methods*, 2004, 132, 57-68). Sensitive fluorescence detection commonly uses a laser and a confocal microscope, e.g., DNA microarray detector made by Affymetrix Inc., which are typically very expensive and need a trained technician to operate.

The detection of protein analytes on microarrays has emerged as a powerful tool for proteomics as well as diagnostics (Macbeath, G. et al. Science (2000), 289, 1760-1763; Moody, M. D. et al. Biotechniques (2001), 31, 186-194; Nielsen, U. B. et al. Journal Immunol. Meth. (2004), 290, 107-120) A variety of different detection methods have been developed for labeling antibody arrays including, but not limited to, fluorescence, (Macbeath, G. et al. Science (2000), 289, 1760-1763; Li, Y. L. et al. (2003), 19, 1557-1566) chemiluminescence (Moody, M. D.; et al. Biotechniques 2001, 31, 186-194), resonance light scattering (Nielsen, U. B. et al. Journal Immunol. Meth. (2004), 290, 107-120), and SERS (Grubisha, D. S. et al. Anal. Chem. (2003), 75, 5936-5943). Signal amplification strategies such as rolling circle amplification (RCA) also have been used to increase the detection sensitivity of fluorescence-based strategies. (Schweitzer, B et al. Nat. Biotechnol. (2002), 20, 359-365; Wiltshire, S. et al. Proc. Natl. Acad. Sci. U.S.A. (2000), 97, 10113-10119) These methods have provided high sensitivity detection (<10 pg/mL) of protein analytes. However, the reproducible preparation of highly purified antibody reagents is both challenging and time consuming (Jayasena, S. D. Clin. Chem. (1999), 45, 1628-1650).

Rapid and simple diagnostic methods for confirming infection with influenza virus are urgently needed. Especially at the beginning of a new pandemic outbreak, an early differential diagnosis may alter clinical management, such as infection control procedures, consideration of antiviral treatment options and avoiding the inappropriate use of drugs. Thus. there is a need for novel techniques to classify subtypes of influenza viruses. There is a need for rapid and sensitive methods for detecting and classifying influenza viruses using glycan arrays.

SUMMARY OF THE INVENTION

Glycan arrays are ideal for virus-cell applications as the arrays present glycan ligands in such a way that mimics cell-cell interactions. Because each virus protein has characteristic binding patterns, a glycan array might be feasible to analyze the subtype of influenza viruses and map the evolution of new influenza subtypes based on their binding preferences. Glycan arrays also have proven to be invaluable in the early identification of epidemics caused by viruses.

The current invention provides glycan assays and arrays that can detect and distinguish between various sub-types and strains of an influenza virus using any suitable nanoparticle amplification technique on glycan assay. The assay can be performed in a single reaction slide or strip. The assay or array can use more than one probe to amplify and detect specific target HA of influenza. Using the information obtained from the assay, it is able to distinguish between various sub-types and strains of an influenza virus. Specifically, the assay can provide a positive or negative (y/n) determination of the presence or absence of influenza virus types A and B, and sub-types H1N1, H3N1, and H5N1 in a sample. Importantly, screening results can be observed directly by naked eyes in a fast manner. This technique also has great potential in detection of vaccination response in individuals.

A comprehensive and sensitive glycan array system for detection and subtype identification of influenza viruses is provided. In one embodiment, a set of nine glycans were selected from a library of twenty nine sialosides to capture the influenza virus and form a unique scanometric fingerprint for each subtype of influenza virus on glass slides.

The sensitivity and specificity of detection by this method is higher compared with the commercially available influenza detection kits. A convenient and efficient profiling system to differentiate influenza virus subtypes is provided. Due to its sensitivity, simplicity and cost effectiveness, the nanoparticle-based glycan array has great potential for being widely adopted as a valuable diagnostic tool to facilitate recognition of influenza outbreaks, even in low resource areas.

One of the most notable aspects about this nanoparticle-based detection method is it requires nothing more than naked eye to read results that currently require chemical labeling and confocal laser scanners. This advantage enables a faster diagnostics for any possible new variant; it can also rapidly determine whether the strain has developed drug resistance.

In one embodiment, the probe targets neuraminidase (NA) using Relenza®-gold nanoparticle complex. In another embodiment, phage techniques are applied to construct phage-gold nanoparticle complex which can specifically target hemagglutinin (HA) subtypes.

The invention relates to methods for detecting at least one type of target analyte in a sample, the method comprising the steps of: a) providing a substrate having at least one type of glycan capture probe bound at a discrete location on the substrate, wherein the capture probe can bind to the target analyte; b) providing at least one type of nanoparticle probe comprising detector moieties, wherein the detector moieties on each type of probe has a configuration that can bind to the target analyte; c) contacting the substrate with the sample under conditions suitable for binding of the target analyte in the sample to the glycan capture probe; d) contacting the target analyte immobilized on the substrate with the nanoparticle probe under conditions that are effective for the binding of the detector moieties to the target analyte; and e) detecting whether the nanoparticle probe binds to the target analyte, wherein the presence or absence of the complex is indicative of the presence or absence of the specific target analyte in the sample.

The invention relates to methods for detecting at least one influenza serotype in a sample, the method comprising the steps of: a) providing a substrate having at least one type of glycan capture probe bound at a discrete location on the substrate, wherein the capture probe can bind to a specific influenza serotype target; b) providing at least one type of nanoparticle probe conjugated to a detector moiety, wherein the detector moiety binds to the specific influenza serotype; c) contacting the substrate with the sample and the nanoparticle probe under conditions suitable for the binding of the glycan capture probe to the specific influenza serotype and the binding of the nanoparticle probe to the specific influenza serotype to form a complex at the discrete location on the substrate; and d) detecting the presence or absence of the complex wherein the presence or absence of the complex is indicative of the presence or absence of the specific influenza serotype in the sample.

In some aspects, the influenza serotype is selected from the group consisting of influenza A serotypes H1N1, H2N2, H3N1, H3N2, H5N1, H7N7, H1N2, H9N2, H7N2, H7N3, and H10N7.

In some aspects, the detector moiety comprises an antibody or fragment thereof that binds to the specific influenza serotype. In some embodiments, the antibody or fragment thereof comprises a phage particle from a phage display.

In some aspects, the target analyte is an antibody, an enzyme, a viral protein, a cellular receptor, a cell type specific antigen, or a nucleic acid, a cellular component or a tissue component from a pathogen, from a prokaryote, prion, virus, bacterium or eukaryote.

In some aspects, the sample is blood, serum, anti-serum, monoclonal antibody preparation, lymph, plasma, saliva, urine, semen, breast milk, ascites fluid, tissue extract, cell lysate, cell suspension, viral suspension, nasopharyngeal aspirate, blood, saliva, or a combination thereof.

In some aspects, the captured target-nanoparticle probe complex is detected by photonic, electronic, acoustic, opto-acoustic, gravity, electro-chemical, electro-optic, mass-spectrometric, enzymatic, chemical, biochemical, or physical means.

In some aspects, the nanoparticles are made of a noble metal. In some embodiments, the nanoparticles are made of gold or silver.

In some aspects, the substrate is a magnetic bead. In some aspects, the substrate has a planar surface. In some aspects, the substrate is made of glass, quartz, ceramic, or plastic.

In some aspects, the detecting comprises contacting the substrate with silver stain.

In some aspects, the detecting comprises detecting light scattered by the nanoparticle. In some embodiments, the detecting comprises observation with an optical scanner. In some embodiments, the scanner is linked to a computer loaded with software capable of calculating grayscale measurements, and the grayscale measurements are calculated to provide a quantitative measure of the amount of target analyte or influenza serotype detected.

In some embodiments, the substrate is addressable. In some embodiments, a plurality of glycan capture probes, each of which can recognize a different target influenza serotype, are attached to the substrate in an array of discrete spots. In some embodiments, the plurality of glycan capture probes comprise glycan structures of at least about 10%, 15%, 20%, 25%, 30%, 35%, 40%, 45%, 50%, 55%, 60%, 65%, 70%, 75%, 80%, 85%, 90% 95%, or more of glycans found on HA receptors in human upper respiratory tract tissues. In some embodiments, the plurality of glycan capture probes comprises a glycan structure of at least one molecule shown in FIG. 7.

In some aspects, the substrate is selected from the group consisting essentially of one of glass, semiconductor, organic polymer, membrane, quartz, silicon, mineral, metal, metal alloy, gold, silver, and mixtures and compositions thereof.

In some embodiments of the method, sample is first contacted with the nanoparticle probe such that a target influenza serotype present in the sample binds to the detector moiety on the nanoparticle probe, and the target influenza serotype bound to the nanoparticle probe is then contacted with the substrate so that the target influenza serotype binds to the glycan capture probe on the substrate.

In some embodiments of the method, sample is first contacted with the substrate so that a target influenza serotype present in the sample binds to a glycan capture probe, and the target influenza serotype bound to the glycan capture probe is then contacted with the nanoparticle probe so that the target influenza serotype binds to the detector moiety on the nanoparticle probe.

In some embodiments of the method, the sample, the nanoparticle probe and the glycan capture probe on the substrate are contacted simultaneously.

In some embodiments of the method, detecting the presence or absence of the complex indicative of the presence or absence of the specific influenza serotype in the sample comprises evaluating a flu vaccination response in an individual from whom the sample is obtained.

These and other aspects will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein. The patent or application file contains at least one drawing executed in color. Copies of this patent or patent application publication with color drawing(s) will be provided by the Office upon request and payment of the necessary fee.

FIG. 1 shows a schematic of an influenza virus type test procedure using a glycan array.

FIG. 3A shows a schematic description of a synergy of nanomaterials and glycan array showing viruses's binding preferences. First, selected glycans were immobilized on a glass slide. A nasal aspirate fluid was then incubated with slides. Glycans with different structures can target hemagglutinin specific to H5N1, H3N1, and H1N1 serotypes. Next, specific antibodies, Relenza-Au (targeting NA), or phage-Au complex (targeting HA) were introduced. Influenza A serotypes can be observed by naked eyes in the case of Relenza-Au and phage-Au and be classified by glycan patterns on glass slides.

FIG. 12 shows glycan array analyses of the four viruses investigated. The binding signals are shown as means of duplicate spots at 100 μM per spot. Each experiment was repeated twice. Arrays consisted of twenty seven sialylated oligosaccharide probes, printed on NHS-coated glass slides (NHS: N-Hydroxy Succinimide). The various types of terminal sialic acid linkage are indicated by the colored panels as defined at the bottom of the figure.

DETAILED DESCRIPTION OF THE INVENTION

Figure 2:
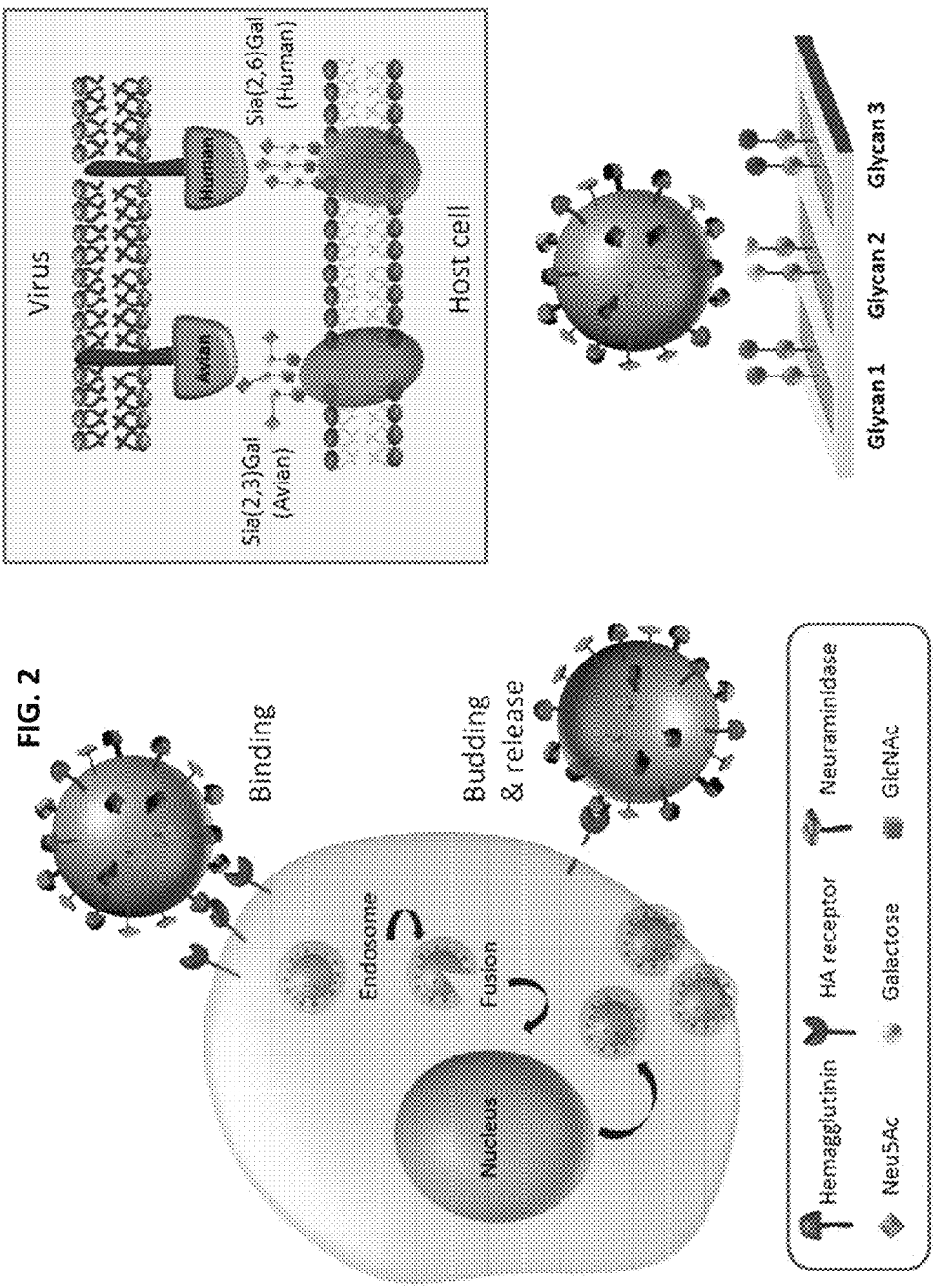
FIG. 2 shows invasion and replication of the influenza virus. The steps of virus binding and releasing are shown on the right panel.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

Definitions

Affinity: As is known in the art, "affinity" is a measure of the tightness with a particular ligand (e.g., an HA polypeptide) binds to its partner (e.g., an HA receptor). Affinities can be measured in different ways.

Binding: It will be understood that the term "binding", as used herein, typically refers to a non-covalent association between or among agents. In many embodiments herein, binding is addressed with respect to particular glycans. It will be appreciated by those of ordinary skill in the art that such binding may be assessed in any of a variety of contexts. In some embodiments, binding is assessed with respect to free glycans. In some embodiments, binding is assessed with respect to glycans attached (e.g., covalently linked to) a carrier. In some embodiments, binding is assessed with respect to glycans attached to an HA receptor. In such embodiments, reference may be made to receptor binding or to glycan binding.

Binding agent: In general, the term "binding agent" is used herein to refer to any entity that binds to glycans. Binding agents may be of any chemical type. In some embodiments, binding agents are polypeptides (including, e.g., antibodies or antibody fragments); in some such embodiments, binding agents are HA polypeptides; in other embodiments, binding agents are polypeptides whose amino acid sequence does not include an HA characteristic sequence. In some embodiments, binding agents are small molecules. In some embodiments, binding agents are nucleic acids. In some embodiments, binding agents are aptamers. In some embodiments, binding agents are polymers. In some embodiments, binding agents are non-polymeric. In some embodiments, binding agents are carbohydrates. In some embodiments, binding agents are lectins. In some embodiments, binding agents compete with hemagglutinin for binding to glycans on hemagglutinin receptors.

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Hemagglutinin (HA) polypeptide: As used herein, the term "hemagglutinin polypeptide" (or "HA polypeptide") refers to a polypeptide whose amino acid sequence includes at least one characteristic sequence of HA. A wide variety of HA sequences from influenza isolates are known in the art; indeed, the National Center for Biotechnology Information (NCBI) maintains a database (www.ncbi.nlm.nih.gov/genomes/FLU/flu.html). Those of ordinary skill in the art, referring to this database, can readily identify sequences that are characteristic of HA polypeptides generally, and/or of particular HA polypeptides (e.g., H1, H2, H3, H4, H5, H6, H7, H8, H9, H10, H11, H12, H13, H14, H15, or H16 polypeptides; or of HAs that mediate infection of particular hosts, e.g., avian, camel, canine, cat, civet, environment, equine, human, leopard, mink, mouse, seal, stone martin, swine, tiger, whale, etc. In some embodiments, an HA polypeptide has an amino acid sequence that includes residues that participate in glycan binding. In some embodiments, an HA polypeptide includes at least 2, 3, 4, or all 5 of these residues.

Pure: As used herein, an agent or entity is "pure" if it is substantially free of other components. For example, a preparation that contains more than about 90% of a particular agent or entity is typically considered to be a pure preparation. In some embodiments, an agent or entity is at least 91%, 92%, 93%, 94%, 95%, 96%, 97%, 98%, or 99% pure.

Vaccination: As used herein, the term "vaccination" refers to the administration of a composition intended to generate an immune response, for example to a disease-causing agent. For the purposes of the present invention, vaccination can be administered before, during, and/or after exposure to a disease-causing agent, and in certain embodiments, before, during, and/or shortly after exposure to the agent. In some embodiments, vaccination includes multiple administrations, appropriately spaced in time, of a vaccinating composition.

Wild type: As is understood in the art, the phrase "wild type" generally refers to a normal form of a protein or nucleic acid, as is found in nature. For example, wild type HA polypeptides are found in natural isolates of influenza virus. A variety of different wild type HA sequences can be found in the NCBI influenza virus sequence database, www.ncbi.nlm.nih.gov/genomes/FLU/FLU.html.

Influenza Virus Assays

This invention provides an influenza virus assay that can detect and distinguish between various sub-types and strains of an influenza virus using any suitable nanoparticle amplification technique on glycan array. This assay can be performed in a single reaction slide.

Influenza viruses are RNA viruses which are characterized by a lipid membrane envelope containing two glycoproteins, hemagglutinin (HA) and neuraminidase (NA), embedded in the membrane of the virus particular. There are 16 known HA subtypes and 9 NA subtypes, and different influenza strains are named based on the number of the strain's HA and NA subtypes. Based on comparisons of amino acid sequence identity and of crystal structures, the HA subtypes have been divided into two main groups and four smaller clades. The different HA subtypes do not necessarily share strong amino acid sequence identity, but the overall 3D structures of the different HA subtypes are similar to one another, with several subtle differences that can be used for classification purposes. For example, the particular orientation of the membrane-distal subdomains in relation to a central α-helix is one structural characteristic commonly used to determine HA subtype (Russell et al., Virology, 325:287, 2004).

HA exists in the membrane as a homotrimer of one of 16 subtypes, termed H1-H16. Only three of these subtypes (H1, H2, and H3) have thus far become adapted for human infection. One reported characteristic of HAs that have adapted to infect humans (e.g., of HAs from the pandemic H1N1 (1918) and H3N2 (1967-68) influenza subtypes) is their ability to preferentially bind to α2-6 sialylated glycans in comparison with their avian progenitors that preferentially bind to α2-3 sialylated glycans (Skehel & Wiley, Ann. Rev Biochem, 69:531, 2000; Rogers, & Paulson, Virology, 127:361, 1983; Rogers et al., Nature, 304:76, 1983; Sauter et al., Biochemistry, 31:9609, 1992; Connor et al., Virology, 205:17, 1994; Tumpey et al., Science, 310:77, 2005).

Several crystal structures of HAs from H1 (human and swine), H3 (avian) and H5 (avian) subtypes bound to sialylated oligosaccharides (of both α2-3 and α2-6 linkages) are available and provide molecular insights into the specific amino acids that are involved in distinct interactions of the HAs with these glycans (Eisen et al., Virology, 232:19, 1997; Ha et al., Proc Natl Acad Sci USA, 98:11181, 2001; Ha et al., Virology, 309:209, 2003; Gamblin et al., Science, 303:1838, 2004; Stevens et al., Science, 303:1866, 2004; Russell et al., Glycoconj J 23:85, 2006; Stevens et al., Science, 312:404, 2006). For example, the crystal structures of H5 (A/duck/Singapore/3/97) alone or bound to an α2-3 or an α2-6 sialylated oligosaccharide identifies certain amino acids that interact directly with bound glycans, and also amino acids that are one or more degree of separation removed (Stevens et al., Proc Natl Acad Sci USA 98:11181, 2001). In some cases, conformation of these residues is different in bound versus unbound states.

The assay method according to the present invention can use more than one or more probes to amplify and detect specific target HA of influenza. Using the information obtained from an amplification reaction it is possible to distinguish between various sub-types and strains of the influenza virus. Specifically, an assay can provide a positive or negative (yes/no) determination of the likely presence or absence of influenza virus types A and B, and sub-types H1N1, H3N2, and H5N1 in a sample. An assay also can be used to monitor for one or more mutations in an influenza virus strain. Mutations in an influenza virus, within, for example the HA and NA, can alter viral infectivity and lethality in different hosts and different tissues.

Receptor specificity for the influenza virus is usually controlled by the glycoprotein HA on the virus surface. These viral HAs bind to host cell receptors containing terminal glycan called sialic acids. With a modest change of two amino acid mutations on HA, the 1918 influenza pandemic switch its binding preference from the human α-2,6 to the avian α-2,3 sialic acid receptor. (See FIG. 2). Features of the differential binding among influenza virus suggest new flu as an intermediary genetic mixing vessel and facilitate a development of diagnostics.

Design of Glycan Arrays

The glycan arrays of the invention can detect and distinguish between various sub-types and strains of an influenza virus using any suitable nanoparticle amplification technique on glycan assay. This assay can be performed in a single reaction slide or strip. The assay or array can use more than one probe to amplify and detect specific target HA of influenza. Using the information obtained from the assay, it is able to distinguish between various sub-types and strains of an influenza virus. Importantly, screening results can be observed directly by naked eyes in a fast manner. This technique also has great potential in detection of vaccination respond to individuals.

The present invention encompasses the finding that binding of influenza virus subtypes to glycans correlates with ability to mediate infection of particular hosts, including for example, humans.

In some embodiments, influenza virus subtypes bind to array glycans (e.g., α2-6 silaylated glycans) with high affinity. For example, in some embodiments, influenza virus subtypes bind to array glycans with an affinity comparable to that observed for wild type HA that mediates infection of a humans (e.g., H1N1 HA or H3N2 HA). In some embodiments, influenza virus subtypes bind to array glycans with an affinity that is at least 25%, 30%, 35%, 40%, 45%, 50%, 55%, 60%, 65%, 70%, 75%, 80%, 85%, 90%, 95%, 96%, 97%, 98%, 99%, or 100% of that observed under comparable conditions for binding to a wild type HA that mediates infection of humans. In some embodiments, influenza virus subtypes bind to array glycans with an affinity that is greater than that observed under comparable conditions for binding to a wild type HA that mediates infection of humans.

In certain embodiments, binding affinity of influenza virus subtypes is assessed over a range of concentrations. Such a strategy provides significantly more information, particularly in multivalent binding assays, than do single-concentration analyses. In some embodiments, for example, binding affinities of inventive binding agents are assessed over concentrations ranging over at least 2, 3, 4, 5, 6, 7, 8, 9, 10 or more fold. In certain embodiments, influenza virus subtypes show high affinity if they show a saturating signal in a multivalent glycan array binding assay such as those described herein.

In some embodiments, influenza virus subtypes bind to α2-6 sialylated glycans; in some embodiments, influenza virus subtypes bind preferentially to α2-6 sialylated glycans. In certain embodiments, influenza virus subtypes bind to a plurality of different α2-6 sialylated glycans. In some embodiments, influenza virus subtypes are not able to bind to α2-3 sialylated glycans, and in other embodiments influenza virus subtypes are able to bind to α2-3 sialylated glycans.

In some embodiments, influenza virus subtypes bind to glycans found on receptors on human upper respiratory epithelial cells. In certain embodiments, influenza virus subtypes bind to glycans corresponding to those on HA receptors in the bronchus and/or trachea. In some embodiments, influenza virus subtypes are not able to bind glycans corresponding to those on receptors in the deep lung, and in other embodiments, influenza virus subtypes are able to bind glycans corresponding to those on receptors in the deep lung.

Figure 7:
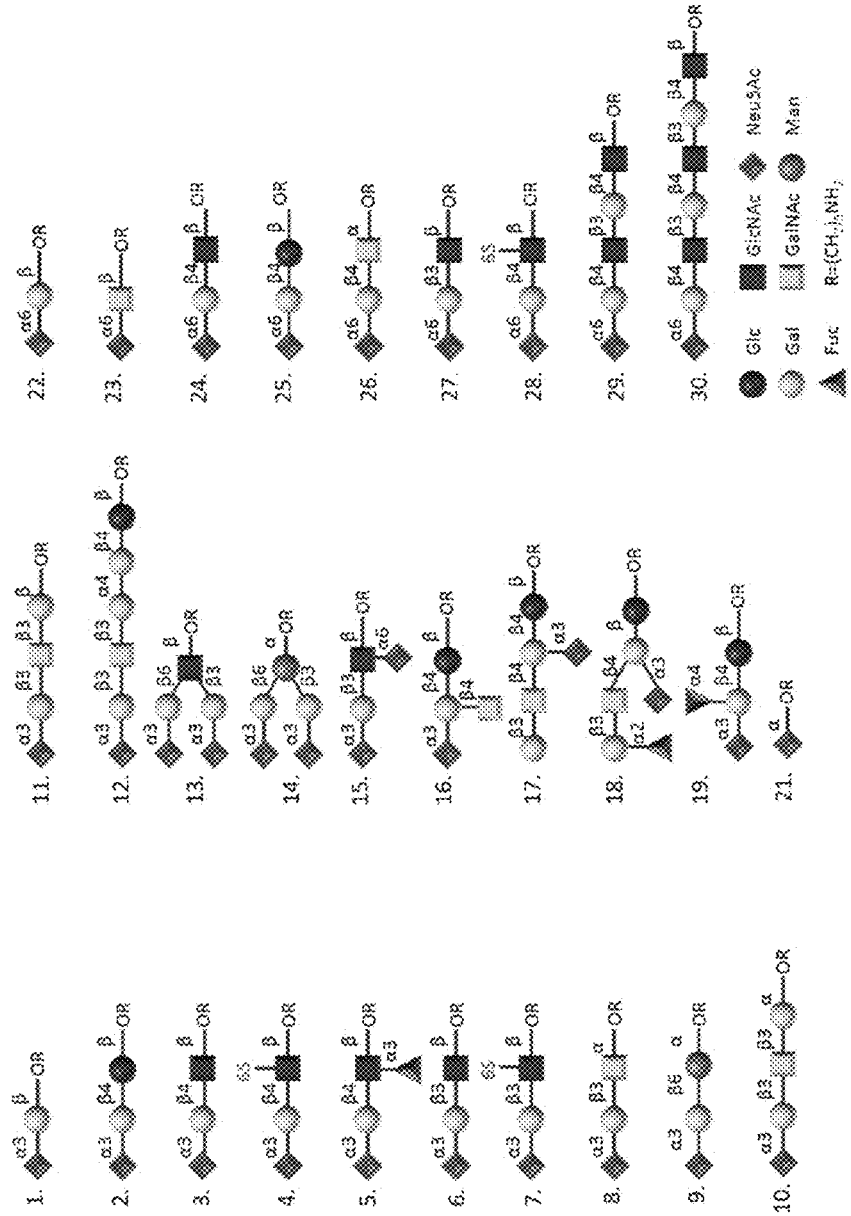
FIG. 7 shows symbolic representations of common monosaccharides and linkage. (reprinted from Consortium for Functional Glycomics: www.functionalglycomics.org)

In some embodiments, glycans corresponding to those on bind to at least about 10%, 15%, 20%, 25%, 30% 35%, 40%, 45%, 50%, 55%, 60%, 65%, 70%, 75%, 80%, 85%, 90% 95% or more of the glycans found on HA receptors in human upper respiratory tract tissues (e.g., epithelial cells). In some embodiments, influenza virus subtypes bind to one or more of the glycans illustrated in FIGS. 7A-7C. In some embodiments, influenza virus subtypes bind to multiple glycans illustrated in FIGS. 7A-7C. In some embodiments, influenza virus subtypes bind with high affinity and/or specificity to glycans illustrated in FIGS. 7A-7C.

In some embodiments, influenza virus subtype binding is mediated through HA polypeptides. For example, the present invention provides glycan arrays that bind to HA polypeptides with specificity. In different embodiments, HA polypeptides that bind to the glycan arrays are H1, H2, H3, H4, H5, H6, H7, H8. H9, H10, H11, H12, H13, H14, H15, or H16 polypeptides.

In certain embodiments, the HA polypeptide is a variant of a known wild type HA polypeptide in that its amino acid sequence is identical to that of a known wild type HA but for a small number of particular sequence alterations. In some embodiments, the wild type HA is an HA polypeptide found in a known natural isolate of an influenza virus. In some embodiments, HA polypeptide variants have different glycan binding characteristics than their corresponding known wild type HA polypeptides.

The invention also provides anti-idiotypic antibodies that bind to glycans wherein the anti-idiotypic antibodies are directed to antibodies that react with circulating influenza virus subtypes present in patients. The anti-idiotype technology is used to produce monoclonal antibodies which mimic an epitope on influenza virus and/or HA polypeptide. For example, an anti-idiotypic monoclonal antibody made to a first monoclonal antibody will have a binding domain in the hypervariable region which is the "image" of the epitope bound by the first monoclonal antibody. An antibody suitable for binding to a glycan is specific for at least one portion or region of the glycan. For example, one of skill in the art can use a whole glycan or fragment of glycan to generate appropriate antibodies of the invention.

Fabrication of Glycan Arrays

The arrays of the invention employ a library of characterized and defined glycan structures. A plurality of glycan molecules carried by at least one solid support. In a related embodiment the solid support is one or more of arrays, beads, microspheres, plates, slides and probes. The array is validated with a diverse set of carbohydrate binding proteins such as Influenza Hemagglutinins and anti-carbohydrate antibodies (from crude sera, purified serum fractions and purified monoclonal antibody preparations).

The glycan libraries, arrays and methods have several advantages. One particular advantage of the invention is that the arrays and methods of the invention provide highly reproducible results.

Another advantage is that the libraries and arrays of the invention permit screening of multiple glycans in one reaction. Thus, the libraries and arrays of the invention provide large numbers and varieties of glycans. For example, the libraries and arrays of the invention have at least two glycans, at least three glycans, at least ten glycans, at least 30 glycans, at least 40 glycans, at least 50 glycans, at least 100 glycans, at least 150 glycans, at least 175 glycans, at least 200 glycans, at least 250 glycans or at least 500 glycans. In some embodiments, the libraries and arrays of the invention have more than two glycans, more than three glycans, more than ten glycans, more than 40 glycans, more than 50 glycans, more than 100 glycans, more than 150 glycans, more than 175 glycans, more than 200 glycans, more than 250 glycans or more than 500 glycans. In other embodiments, the libraries and arrays of the invention have about 2 to about 100,000, or about 2 to about 10,000, or about 2 to about 7500, or about 2 to about 1,000, or about 2 to about 500, or about 2 to about 200, or about 2 to 100 different glycans per library or array. In other embodiments, the libraries and arrays of the invention have about 50 to about 100,000, or about 50 to about 10,000, or about 50 to about 7500, or about 50 to about 1,000, or about 50 to about 500, or about 50 to about 200 different glycans per library or array. Such large numbers of glycans permit simultaneous assay with a multitude of different glycans.

As described herein, the present arrays are used for screening a variety of glycan binding proteins, specifically influenza virus, HA and NA proteins. The glycan arrays of the invention are reusable after stripping with acidic, basic aqueous or organic washing steps. Experiments demonstrate that little degradation of the glycan occurs and only small amounts of glycan binding proteins are consumed during a screening assay. Hence, the arrays of the invention can be used for more than one assay.

The arrays and methods of the invention provide high signal to noise ratios. The screening methods provided by the invention are fast and easy because they involve only one or a few steps. No surface modifications or blocking procedures are typically required during the assay procedures of the invention.

The composition of glycans on the arrays of the invention can be varied as needed by one of skill in the art. Many different glycoconjugates can be incorporated into the arrays of the invention including, for example, purified glycans, naturally occurring or synthetic glycans, glycoproteins, glycopeptides, glycolipids, bacterial and plant cell wall glycans and the like. Immobilization procedures for attaching different glycans to the arrays of the invention are readily controlled to easily permit array construction.

An essential requirement for microarray analyses is that the probe spots be discreet and readily distinguishable from each other. Without this, no valid conclusions can be drawn. As a consequence, analysis of replicate array probes of the same sample is highly preferred in order to draw definitive conclusions about changes in gene expression. The quality of arrays is critically important due to a large number of genes to be probed and detected on the microarray hybridization chip.

Spacer molecules or groups can be used to link the glycans to the arrays. Such spacer molecules or groups include fairly stable (e.g. substantially chemically inert) chains or polymers. For example, the spacer molecules or groups can be alkylene groups. One example of an alkylene group is —$(CH_2)_n$—, where n is an integer of from 1 to 20. In some embodiments, n is an integer of from 1 to 10.

Unique libraries of different glycans are attached to defined regions on the solid support of the array surface by any available procedure. In general, the arrays are made by obtaining a library of glycan molecules, attaching spacer molecules with linking moieties to the glycans in the library, obtaining a solid support that has a surface derivatized to react with the specific linking moieties present on the glycans of the library and attaching the glycan molecules to the solid support by forming a covalent linkage between the linking moieties and the derivatized surface of the solid support.

The derivatization reagent can be attached to the solid substrate via carbon-carbon bonds using, for example, substrates having (poly)trifluorochloroethylene surfaces, or more preferably, by siloxane bonds (using, for example, glass or silicon oxide as the solid substrate). Siloxane bonds with the surface of the substrate are formed in one embodiment via reactions of derivatization reagents bearing trichlorosilyl or trialkoxysilyl groups.

Figure 1:
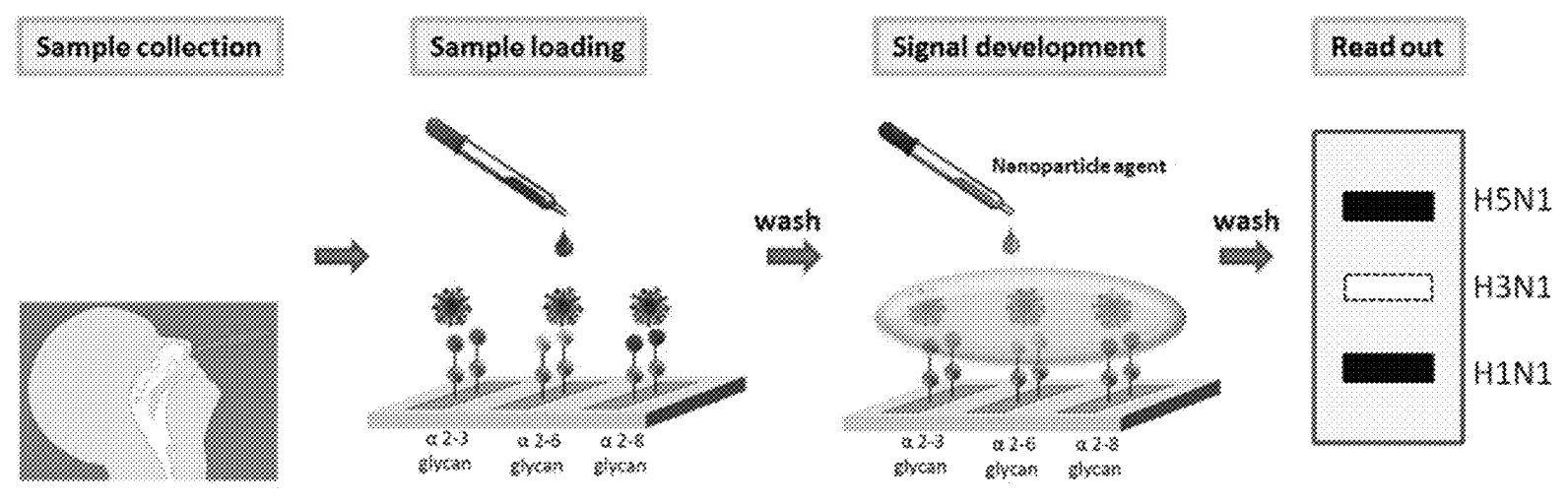

The glycans of the invention can have spacers, linkers, labels, linking moieties and/or other moieties attached to them. These spacers, linkers, labels, linking moieties and/or other moieties can be used to attach the glycans to a solid support, detect particular glycans in an assay, purify or otherwise manipulate the glycans. For example, a glycan library can be employed that has been modified to contain primary amino groups. Thus, in some embodiments, the glycans of the invention can have amino moieties provided by attached alkylamine groups, amino acids, peptides, or proteins. For example, the glycans can have alkylamine groups such as —$O(CH_2)_nNH_2$ attached that provide the primary amino group. The primary amino groups on the glycans can react with an N-hydroxy succinimide (NHS)-derivatized surface of the solid support. Such NHS-derivatized solid supports are commercially available. For example, NHS-activated glass slides are available from Accelr8 Technology Corporation, Denver, Colo. (now Schott Nexterion, Germany). After attachment of all the desired glycans, slides can further be incubated with ethanolamine buffer to deactivate remaining NHS functional groups on the solid support. The array can be used without any further modification of the surface. No blocking procedures to prevent unspecific binding are typically needed. FIG. 1 provides a schematic diagram of such a method for making arrays of glycan molecules.

The substrate can be any suitable solid material, including without limitation solid materials formed from or containing silicons (such as, but not limited to semi-conductors), organic polymers (e.g., cellulosic paper, polymeric membranes, and the like), inorganic polymers (e.g., membranes), micas, minerals, quartzes, plastics, glasses, metals and metal alloys (such as, copper, platinum, palladium, nickel, cobalt, rhodium, iridium, gold, silver, titanium, and aluminum), and combinations or composites thereof. More preferred solid materials are fabricated from or comprise quartz, glass, paper, gold, silver, titanium, aluminum, copper, nickel, silicon, or organic polymer. Even more preferably, the substrate is a microscope glass slide (e.g., Corning™, Corning, N.Y.), silicon wafer, or quartz.

The substrate can have any three-dimensional geometric shape. Preferably, the substrate is substantially a flat plane or approximates one of a sphere, cylinder, capillary, or wire. While the method is described with reference to a multiple format substrate, such as a microarray, it is to be understood that it can be applied to a single format substrate, such as a nanoparticle.

Each type of glycan is contacted or printed onto to the solid support at a defined glycan probe location. Suitable printing methods include piezo or pin printing techniques. A microarray gene printer can be used for applying the various glycans to defined glycan probe locations. The printing process is shown diagrammatically in FIG. 3. Printing in the X direction gives rise "columns" of glycans and printing in the direction orthogonal to the X direction gives rise to "rows." During printing, the inkjet is generally stationary, and a stepping stage moves the glass slide or other solid surface over the head in the X direction. As the wafer passes over the head, it prints the appropriate glycan to each glycan probe location. Several nozzles simultaneously dispense a selected amount of glycan solution.

For example, about 0.1 nL to about 10 nL, or about 0.5 nL of glycan solution can be applied per defined glycan probe location. Various concentrations of the glycan solutions can be contacted or printed onto the solid support. For example, a glycan solution of about 0.1 to about 1000 µM glycan or about 1.0 to about 500 µM glycan or about 10 to about 100 µM glycan can be employed. In general, it may be advisable to apply each concentration to a replicate of several (for example, three to six) defined glycan probe locations. Such replicates provide internal controls that confirm whether or not a binding reaction between a glycan and a test molecule is an actual binding interaction.

An "addressable substrate" used in a method of the invention can be any surface capable of having glycans bound thereto. Such surfaces include, but are not limited to, glass, metal, plastic, or materials coated with a functional group designed for binding of glycans. The coating may be thicker than a monomolecular layer; in fact, the coating could involve porous materials of sufficient thickness to generate a porous 3-dimensional structure into which the glycans can diffuse and bind to the internal surfaces.

Influenza Virus Detection

The invention provides methods of detecting viral infection, for example, influenza infection. The method involves contacting a test sample from a patient with a library or array of glycans and observing whether virus, or viral antigens present in the test sample are reactive with the array. The presence of such viral antigens and viral particles can be detected by detecting their binding to glycans that have been determined to previously bind those viral antigens and viral particles. Hence, the glycans to which the viral antigens or viruses bind indicate whether an infection is present. Such glycans can be viral-specific glycan epitopes or viral binding sites that are present on host cells. One of skill in the art can readily prepare glycan arrays for screening for viral infection using the teachings provided herein.

The affinity interaction of the glycan molecules to the influenza virus or fragments or peptides thereof can be measured by optical (UV-Vis), fluorescence, surface-enhanced fluorescence, surface plasmon resonance, surface-enhanced Raman scattering microscopy, or electrochemical and chemilluminescent techniques. Commonly, the detection method is direct immunoassay, sandwich immunoassay with a labeling or unlabeling approach. To enhance the sensitivity and specificity of the assay a sandwich assay is used.

The glycosylation of viral proteins is generally performed by host cell, rather than viral, enzymes. Given that many viral genomes are so mutable, the glycosylation of viral proteins by host enzymes likely gives rise to antigenic epitopes that are more stable than the epitopes generated by translation of easily mutated viral nucleic acids. Hence, virally-associated glycans may form the basis of improved compositions, including vaccines, for inhibiting and treating viral infection.

Influenza virus hemagglutinin binds to Neu5Acα2-3-linked to galactosides, but not to any Neu5Acα2-6- or Neu5Acα2-8-linked sialosides. Intact influenza viruses, such as H1N1/Brisbane, H1N1/swine, H3N1/Brisbane and H5N1/Vietnam, also bind the array and show specificity for both α2-3 and α2-6 sialosides. (FIG. 5) Influenza viruses also bind Neu5Acα2-3- and Neu5Acα2-6-linked to galactosides as well as certain O-linked sialosides.

The term "capture probe" refers to a glycan immobilized on an addressable substrate. Target analytes such as proteins, polypeptides, fragments, variants, and derivatives of influenza virus also may be used to prepare antibodies using methods known in the art. Thus, antibodies and antibody fragments that bind to target analytes may be used in sandwich assays after the influenza virus or protein or fragment thereof is captured on a substrate. Antibodies may be polyclonal, monospecific polyclonal, monoclonal, recombinant, chimeric, humanized, fully human, single chain and/or bispecific.

Polyclonal antibodies directed toward a target analyte generally are raised in animals (e.g., rabbits or mice) by multiple subcutaneous or intraperitoneal injections of the polypeptide and an adjuvant. It may be useful to conjugate a target analyte protein, polypeptide, or a variant, fragment or derivative thereof to a carrier protein that is immunogenic in the species to be immunized, such as keyhole limpet heocyanin, serum, albumin, bovine thyroglobulin, or soybean trypsin inhibitor. Also, aggregating agents such as alum are used to enhance the immune response. The preparation of polyclonal antibodies is well-known to those skilled in the art (Green et al., Production of Polyclonal Antisera, in Immunochemical Protocols (Manson, ed.), pages 1-5 (Humana Press 1992); Coligan et al., Production of Polyclonal Antisera in Rabbits, Rats, Mice and Hamsters, in Current Protocols in Immunology, section 2.4.1 (1992), which are hereby incorporated by reference). For example, an HA or HA mixture is injected into an animal host, preferably according to a predetermined schedule incorporating one or more booster immunizations, and the animal is bled periodically. Polyclonal antibodies specific for a glycan or glycan fragment may then be purified from such antisera by, for example, affinity chromatography using the glycan coupled to a suitable solid support.

Monoclonal antibodies directed toward target analytes are produced using any method that provides for the production of antibody molecules by continuous cell lines in culture. The preparation of monoclonal antibodies likewise is conventional (Kohler & Milstein, Nature, 256:495 (1975); Coligan et al., sections 2.5.1-2.6.7; and Harlow et al., Antibodies: A Laboratory Manual, page 726 (Cold Spring Harbor Pub. 1988)), which are hereby incorporated by reference. Briefly, monoclonal antibodies can be obtained by injecting mice with a composition comprising an antigen (HA), verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (Coligan et al., sections 2.7.1-2.7.12 and sections 2.9.1-2.9.3; Barnes et al., Purification of Immunoglobulin G (IgG), in Methods in Molecular Biology, Vol. 10, pages 79-104 (Humana Press 1992)). Methods of in vitro and in vivo multiplication of monoclonal antibodies are available to those skilled in the art.

The antibodies may be employed in direct and indirect sandwich assays (Sola, Monoclonal Antibodies: A Manual of Techniques 147-58 (CRC Press 1987)) for detection and quantitation of the target viruses.

Sandwich assays generally involve the use of antibodies capable of binding to an immunogenic portion, or epitope, of the protein to be detected and/or quantitated. In a sandwich assay, the test sample analyte is typically bound by a glycan which is immobilized on a solid support, and thereafter an antibody binds to the analyte, thus forming an insoluble three part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assays). For example, one type of sandwich assay is an ELISA assay, in which case the detectable moiety is an enzyme.

Antibodies can also be prepared through use of phage display techniques. In one example, a subject is immunized with an antigen, such as influenza serotypes. Lymphocytes are isolated from the spleen of the immunized subject. Total RNA is isolated from the splenocytes and mRNA contained within the total RNA is reverse transcribed into complementary deoxyribonucleic acid (cDNA). The cDNA encoding the variable regions of the light and heavy chains of the immunoglobulin is amplified by polymerase chain reaction (PCR). To generate a single chain fragment variable (scFv) antibody, the light and heavy chain amplification products may be linked by splice overlap extension PCR to generate a complete sequence and ligated into a suitable vector. E. coli are then transformed with the vector encoding the scFv, and are infected with helper phage, to produce phage particles that display the antibody on their surface. Alternatively, to generate a complete antigen binding fragment (Fab), the heavy chain amplification product can be fused with a nucleic acid sequence encoding a phage coat protein, and the light chain amplification product can be cloned into a suitable vector. E. coli expressing the heavy chain fused to a phage coat protein is transformed with the vector encoding the light chain amplification product. The disulfide linkage between the light and heavy chains is established in the periplasm of E. coli. The result of this procedure is to produce an antibody library with up to $10^9$ clones. The size of the library can be increased to $10^{18}$ phage by later addition of the immune responses of additional immunized organisms that may be from the same or different hosts. Antibodies that recognize a specific antigen can be selected through panning Briefly, an entire antibody library can be exposed to an immobilized antigen against which antibodies are desired. Phage that do not express an antibody that binds to the antigen are washed away. Phage that express the desired antibodies are immobilized on the antigen. The phage are then eluted and again amplified in E. coli. This process can be repeated to enrich the population of phage that expresses antibodies that specifically bind to the antigen. After phage are isolated that express an antibody that binds to an antigen, a vector containing the coding sequences for the antibody can be isolated from the phage particles and the coding sequences can be recloned into a suitable vector to produce an antibody in soluble form. In another example, a human phage library can be used to select for antibodies, such as monoclonal antibodies, that bind to specific influenza serotypes. These methods may be used to obtain human monoclonal antibodies that bind to specific influenza serotypes.

Phage display methods to isolate antigens and antibodies are known in the art and have been described (Gram et al., Proc. Natl. Acad. Sci., 89:3576 (1992); Kay et al., Phage display of peptides and proteins: A laboratory manual. San Diego: Academic Press (1996); Kermani et al., Hybrid, 14:323 (1995); Schmitz et al., Placenta, 21 Suppl. A:S106 (2000); Sanna et al., Proc. Natl. Acad. Sci., 92:6439 (1995)).

Gold Nanoparticle—Phage Conjugation & Gold Nanoparticle-Neuraminidase Inhibitor Conjugation for Designing Nanoparticles Probes There are two strategies for making nanoparticle-based probes in influenza virus subtype detection: one is attempting to target neuraminidase (NA) using a gold nanoparticle complex comprising a neuraminidase binding agent, such as a neuraminidase inhibitor. Second is applying phage technique to construct phage-gold nanoparticle complex which can specifically target hemagglutinin subtypes (HA).

Neuraminidase inhibitors are a class of antiviral drugs targeted at the influenza virus, which work by blocking the function of the viral neuraminidase protein, thus preventing the virus from reproducing by budding from the host cell. Oseltamivir (Tamiflu®) a prodrug, Zanamivir (Relenza®), Laninamivir (Inavir®), and Peramivir belong to this class. Unlike the M2 inhibitors, which work only against the influenza A, neuraminidase inhibitors act against both influenza A and influenza B. Relenza® (or Zanamivir) is a neuraminidase inhibitor used in the treatment of influenza caused by influenza A virus and influenza B virus. Gold nanoparticles were conjugated with modified relenza service as a universal probe for influenza virus detection. The Relenza-Au probes have advantages in detecting a new strain of influenza or co-infection of two strains of influenza viruses. Another approach is fabricating a hemagglutinin probe consisting of bacteriophage (phage) assembled with gold (Au) nanoparticles. HA subtype specific binding phages were affinity selected through biopanning Phage antibodies with higher affinity may be enriched during successive rounds of selection by decreasing the concentration of antigen. Four different high affinity HA-specific phages were named as MG4B for Cal/09 H1N1, CW2B for Brisbane H1N1, 12a for Brisbane H3N2 and 8a for RG14 H5N1, respectively. The selected phages, which carry up to 4000 analyte-binding domains on its surface, can be used to conjugate gold nanoparticles. The assembly of Au nanoparticles onto phage occurs without modification of the pVIII major capsid proteins or complex conjugation chemistry. Au nanoparticles appear as black dots connecting long, white, filamentous phage structures. Once assembled, the phage in these networks still maintained their ability to target HA. Furthermore, these phages were dramatically more effective and sensitivity for the visualization of binding to influenza virus in glycan array dot blot assays. Due to the HA specificity of phages, a sialoside-phage sandwich assay give more specificity in influenza serotype identification.

The modified nanoparticle probes for in situ virus quantification can provide rapid and inexpensive diagnostics for detection and characterization of influenza viruses. One of the most notable aspects about this nanoparticle-based detection method is that it requires nothing more than naked eye to read the results.

Nanoparticle-Based Detection

A nanoparticle-based detection for glycan arrays was developed by Liang et al. who synthesized iron oxide/gold core/shell nanoparticles conjugated with antibodies or proteins (Liang C H et al. Anal. Chem. 2009; 81, 7750-7756). Iron oxide/gold core/shell nanoparticles unite the ability of magnetic property for enrichment, surface modification, and signal enhancement in a single entity. This powerful combination enables researchers to quickly concentrate viruses by an external magnetic field, easily conjugate biomolecules on gold surface, and amplify signal by depositing silver on gold surface of core/shell nanoparticles. The nanoparticle-based assay can reach sub-attomole detection level and has clear advantages in screening different types of viruses.

Nanoparticles have been recently introduced for detecting DNA microarray hybridization. DNA probes are synthesized on gold nanoparticles and hybridized with DNA on glass surface. The sensitivity of the gold labeling method is almost equal to that of fluorescent labeling (Cao, Y. C.; Jin, R.; Mirkin, C. A. Science, 2002, 289, 1757-60; T. A. Taton, C. A. Mirkin, R. L. Letsinger, Science 289 (2000) 1757-1760). Silver enhancement is usually pursued to amplify the signal.

Particles may be of any suitable size including nanoparticles and microsized particles, 1 μm or less in diameter, and may be made of any suitable material such as polymers (e.g., polystyrene), metals (e.g., gold or silver), ceramics, semiconductor material. Methods of making metal, semiconductor and magnetic nanoparticles are well-known in the art. See, e.g., Schmid, G. (ed.) Clusters and Colloids (V C H, Weinheim, 1994); Hayat, M. A. (ed.) Colloidal Gold: Principles, Methods, and Applications (Academic Press, San Diego, 1991); Massart, R., IEEE Transactions On Magnetics, 17, 1247 (1981); Ahmadi, T. S. et al., Science, 272, 1924 (1996); Henglein, A. et al., J. Phys. Chem., 99, 14129 (1995); Curtis, A. C., et al., Angew. Chem. Int. Ed. Engl., 27, 1530 (1988). Suitable gold nanoparticles are commercially available from, e.g., Ted Pella, Inc. (gold), Amersham Corporation (gold), Nanoprobes, Inc. (gold).

Sandwich assays generally involve the use of two antibodies, each capable of binding to a different immunogenic portion, or epitope, of the protein to be detected and/or quantitated. In a sandwich assay, the test sample analyte is typically bound by a first antibody which is immobilized on a solid support, and thereafter a second antibody binds to the analyte, thus forming an insoluble three part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assays). For example, one type of sandwich assay is an ELISA assay, in which case the detectable moiety is an enzyme.

The present invention provides a modified sandwich assay in which the first antibody is replaced with influenza serotype specific glycans immobilized on an array. FIG. 3 illustrates a representative sandwich assay involving a glycan array having capture glycan probes, a detection probe having a detector phage having an antibody fragment specific for a influenza serotype labeled with a detection moiety (e.g., gold), and a target analyte (influenza virus) sandwiched between the capture probe and detector probe.

Methods for preparing gold nanoparticle probes have led to the development of a colorimetric sensing scheme for oligonucleotides and non-nucleic acid targets. See, for instance, U.S. Pat. No. 6,506,564, which describes a colorimetric sensing scheme based on DNA-modified nanoparticles. This method is based on the hybridization of two gold nanoparticle probes to two distinct regions of a target of interest. The binding of the target results in the formation of target/gold nanoparticle probe aggregate when sufficient target is present. The target recognition results in a colorimetric transition due to the decrease in inter-particle distance between the particles. This colorimetric change can be monitored optically, with a UV-visible spectrophotometer, or visually with the naked eye. In addition, the color is intensified when the solutions are concentrated onto a membrane. Therefore, a simple colorimetric transition provides evidence for the presence or absence of a specific target.

As described herein, nanoparticle probes, particularly gold nanoparticle probes comprising phage particles, are surprising and unexpectedly suited for detection of influenza serotypes on glycan arrays. A silver-based signal amplification procedure in a microarray-based assay can further provide ultra-high sensitivity enhancement. Silver staining can be employed with any type of nanoparticles that catalyze the reduction of silver. Preferred are nanoparticles made of noble metals (e.g., gold and silver). (See Bassell, et al., J. Cell Biol., 126, 863-876 (1994); Braun-Howland et al., Biotechniques, 13, 928-931 (1992)). Silver staining can be used to produce or enhance a detectable change in any assay performed on a substrate, including those described above. In particular, silver staining has been found to provide a huge increase in sensitivity for assays employing a single type of nanoparticle so that the use of layers of nanoparticles, aggregate probes and core probes can often be eliminated.

A nanoparticle can be detected in a method of the invention, for example, using an optical or flatbed scanner. The scanner can be linked to a computer loaded with software capable of calculating grayscale measurements, and the grayscale measurements are calculated to provide a quantitative measure of the amount of analyte detected.

Suitable scanners include those used to scan documents into a computer which are capable of operating in the reflective mode (e.g., a flatbed scanner), other devices capable of performing this function or which utilize the same type of optics, any type of grayscale-sensitive measurement device, and standard scanners which have been modified to scan substrates according to the invention.

The software can also provide a color number for colored spots and can generate images (e.g., printouts) of the scans, which can be reviewed to provide a qualitative determination of the presence of an influenza virus serotype, the quantity of an influenza virus serotype, or both. In addition, it has been found that the sensitivity of assays can be increased by subtracting the color that represents a negative result from the color that represents a positive result.

The computer can be a standard personal computer, which is readily available commercially. Thus, the use of a standard scanner linked to a standard computer loaded with standard software can provide a convenient, easy, inexpensive means of detecting and quantitating an influenza virus serotypes when the assays are performed on substrates. The scans can also be stored in the computer to maintain a record of the results for further reference or use. Of course, more sophisticated instruments and software can be used, if desired.

A nanoparticle can be detected in a method of the invention, for example, using resonance light scattering, after illumination by various methods including dark-field microscopy, evanescent waveguides, or planar illumination of glass substrates. Metal particles >40 nm diameter scatter light of a specific color at the surface plasmon resonance frequency (Yguerabide, J.; Yguerabide, E. E. Anal. Biochem. (1998), 262, 157-176) and can be used for multicolor labeling on substrates by controlling particle size, shape, and chemical composition (Taton, T. A.; Lu, G.; Mirkin, C. A. J. Am. Chem. Soc. (2001), 123, 5164-5165; Jin, R. C.; Cao, Y. W.; Mirkin, C. A.; Kelly, K. L.; Schatz, G. C.; Zheng, J. G. Science (2001), 294, 1901-1903) In another embodiment, a nanoparticle can be detected in a method of the invention, for example, using surface enhanced raman spectroscopy (SERS) in either a homogeneous solution based on nanoparticle aggregation (Graham and coworkers, Angew. Chem., 2000, 112, 1103) or on substrates in a solid-phase assay (Porter and coworkers, Anal. Chem., 1999, 71, 4903-4908), or using silver development followed by SERS (Mirkin and coworkers, Science, 2002, 297, 1536-1540).

In another embodiment, the nanoparticles of the invention are detected by photothermal imaging (Boyer et. al, Science, 2002, 297, 1160-1163). In another embodiment, the nanoparticles of the invention are detected by diffraction-based sensing technology (Bailey et. al, J. Am Chem. Soc., 2003, 125, 13541). In another embodiment, the nanoparticles of the invention are detected by hyper-Rayleigh scattering (Kim et. al, Chem Phys. Lett., 2002, 352, 421).

With the use of nanobiotechnology, a nanoparticle-based assay for in situ virus quantification is provided which can provide rapid diagnostics for detection and characterization of viruses. It can tell the subtypes of influenza A such as H1N1/Brisbane, H1N1/swine, H3N1/Brisbane, and H5N1/Vietnam. The method is inexpensive and easily reproducible and requires no advanced specialized training.

An exemplary sequence of steps according to the invention is shown in FIG. 1.

Step 1: sample collection. A typical animal or avian sample comprises a nasopharyngeal aspirate, blood, saliva, or any other bodily fluid to be tested. In addition, a sample can be obtained from a mammal, such as a human, or a bird. In the case of pandemic influenza A (H1N1) virus 2009 detection, a nasopharyngeal swab or saliva is the preferred specimen.

Step 2: sample loading. An assay or array is composed of naturally occurring or synthetic oligosaccharides (glycans). Glycans can be immobilized on a glass slide or other templates. A nasal aspirate fluid, pharyngeal swab fluid or saliva (collected from step 1) is incubated on the glass surface or other templates. At this step, glycans with different structures can target hemagglutinin specific to H5N1, H3N1, and H1N1 serotypes for influenza virus detection.

Step 3: signal development. The amplification and detection is based on the gold-phage technique. Gold nanoparticle-phage probe (nanoparticle agent specific for an influenza virus serotype) is introduced to incubate with virus immobilized on the glass slide surface or other assay template. The nanoparticle amplification method used in an assay can be gold nanoparticle or gold-phage complex and optionally, other types of nanoparticles, such as silver nanoparticles. Gold nanoparticles have an increased detectable signal upon hybridizing to phage. An assay for an amplification target containing variations may use one detection probe for all variations, a single Au-phage probe for one variant, or multiple Au-phages probes, one for each variant. In addition, silver reagent can be applied to further amplify the signal (optional).

Step 4: read out. Results, such as Influenza serotypes, can be observed by naked eyes, barcode scanner or laser pen on glass slides and classify by fingerprint patterns on glycan array.

A sensitive glycan array using gold nanoparticle-phage probe was developed. When coupled with a signal amplification method based on nanoparticle-promoted reduction of silver, the sensitivity of Au phage assay reached higher sensitivity in virus detection. This technique is suitable for rapid screening, is easy to operate, and signals generated can be read by naked eye. The experimental procedure is shown in FIG. 3.

First, glycans were immobilized on a glass slide. A nasal aspirate fluid or pharyngeal swab fluid was incubated on the glass surface. Glycans with different structures can target hemagglutinin specific to H5N1, H3N1, and H1N1 serotypes. In the next step, nanoparticle-phage complex were introduced. Silver reagent was then applied to amplify the signal (this step is optional). In the last steps, Influenza A serotypes can be observed by naked eyes on glass slides and classified by patterns on glycan array.

The fingerprint read-out information from small-scale glycan assay is important to the development of a successful influenza diagnostic product. On main reason is that the time to produce a H1N1 specific diagnosis using the current serological methods or molecular biology methods is too long for effective use during this pandemic. As we known, rapid diagnosis of pandemic virus, especially at the beginning of a new community outbreak or for unusual cases, has important implications for case management. Assays described here provide a simple, rapid and cost effective method for influenza virus subtype detection and hence, ought to be implemented for large-scale detection aimed at controlling influenza virus outbreaks. This influenza diagnostic assay can also be rapidly adapted to identify a new strain of virus while still keeping the current identifications through the simple measure of establishing and validating a new read-out pattern/fingerprint for the emerging threat. In addition, this test will be in a simple slide format that can give a quick test result in order to save both time and money. Importantly, it also has great potential in evaluating the flu vaccination response to individuals.

Specificity of Gold Nanoparticle Based Small Scale Glycan Array (GNBSSGA) for Distinguishing Virus Types The first step in proper prevention and treatment of disease is accurate diagnosis. Several rapid influenza diagnostic tests (including so-called "point-of-care" diagnostic tests) are commercially available. However, studies indicate that rapid diagnostic tests miss many infections with pandemic (H1N1) virus and therefore negative results cannot rule out disease and should not be used as grounds to withhold therapy or lift infection control measures. In addition, co-circulation of current seasonal human H1N1, H3N2, and Swine-Origin Influenza (S-OIV) A (H1N1) viruses poses a challenge for sub-typing individual strains and potential reassortants. The rapidly evolving nature of the influenza virus will continue to pose tremendous threat to public health. Since gold nanoparticle based small scale glycan array (GNBSSGA) is able to distinguish influenza serotype by their fingerprint patterns, a unique fingerprint pattern occurs when co-infection or re-assortment of two strains of influenza viruses occurs. The GNBSSGA is able to be rapidly adapted to identify co-infection or new strains of influenza.

Rapid detection and classifying of influenza virus and identification of its various strains is critical to identification and control of a potential human pandemic. The present invention provides multiple levels of identification—the first level classifies the virus and alerts the user to the presence of pandemic threat viruses and the second level precisely identifies the pathogen. The fingerprint read-out information from glycan assay is critical to the development of a successful seasonal and pandemic influenza diagnostic product for two main reasons. First, the time to produce an H1N1 specific quick test using the current technologies and methods is too long for effective use during this pandemic. Second, the next pandemic flu will almost certainly be a new or modified influenza strain (HxNy), making any of the current quick test diagnostics that might be directed to a particular flu sub-type obsolete or marginally effective, or both. The influenza triage diagnostic assay can be rapidly adapted to identify the new strain of virus while still keeping the current identifications through the simple measure of establishing and validating a new read-out pattern/fingerprint for the emerging threat. Further, the technology and its application is not limited to the detection of the H1N1 virus or even new virus. This technology can be quickly and effectively applied to detect any pandemic virus or biological agent.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1: Glycan Synthesis

All oligosaccharides were prepared using synthetic procedures as described (Hsu, C.-H. et al. Chem. Eur. J. 2010, 16, 1754-1760; Hasegawa A, et al. Carbohydr. Res. 1995, 274, 165-181; Komba S, et al. Bioorg. Med. Chem. 1996, 4, 1833-1847; Otsubo N, et al. Carbohydr. Res. 1998, 306, 517-530; Yoshida M, et al. Glycoconjugate J. 1993, 10, 324). The synthetic oligosaccharides were further modified to cross-link to glass surface for the preparation of "glycan arrays" as described below.

Example 2: Virus Preparation

Samples of various viruses are collected from the Center for Disease Control and Prevention in TAIWAN, and provided by Dr. Jia-Tsong Jan (Genomic Research Center, Academia Sinica, Taiwan). All viruses were propagated in 10-day-old embryonated specific-pathogen free chicken eggs. Purified viruses were done by centrifugation at 100, 000 g for 30 min and resuspended in PBS. Differences in the degree of virus purity did not influence significantly the pattern of receptor binding. Virus were inactivated by treatment with β-propiolactone (BPL; 0.05% v/v) for 60 minutes at 33° C., and resuspended in 0.01 M phosphate buffered saline pH 7.4 (PBS) and stored at −80° C. Comparison of samples of live and inactivated virus showed that BPL inactivation did not alter receptor binding specificity (Matrosovich M, et al. J. Virol. 1999, 73, 1146-1155.)

Example 3: Glycan Array Fabrication

Amino-reactive N-hydroxysuccinimide (NHS)-activated glass microscope slides were used to fabricate glycan arrays by the standard protocol of Protein Application Nexterion Slide H. The NHS groups on the glass surface react readily with the primary amines of the amino modified glycans to form an amide linkage. Amine-modified glycans with desired concentration were dissolved in printing buffer (pH 8.5, 300 mM phosphate buffer with 0.005% (v/v) Tween 20) and were spotted on the glass microscope slides by robotic pin (BioDot, Cartesian Technologies; SMP3, Telechem International) deposition. Print slides were incubated under 80% humidity at 37° C. for 2 h followed by desiccation overnight. Before the binding assay, print slides were immersed with blocking buffer (50 mM ethanolamine in 50 mM borate buffer, pH 9.2) at room temperature for 1 h to remove remaining free NHS groups and then washed with washing buffer (PBST; 50 mM PBS buffer with 0.05% (v/v) Tween 20, pH 7.4) and DI water several times. These slides were dried by argon flow and stored at room temperature in a vacuum desiccator until use (Liang C H, et al. Anal. Chem. 2009; 81, 7750-7756).

Example 4: Phage Display

Phage display is a well-known technique utilized for the selection of antibodies that bind to a desired target. Phage-displayed antibody fragments can offer an advantage over the solubly expressed fragments for use as reporter elements in immunoassays. Herein, samples of phages were home-made by Dr. An-Suei Yang (Genomic Research Center, Academia Sinica, Taiwan). Specific Influenza serotype antibodies are displayed on the surface of phage. This was achieved by fusing the coding sequence of the antibody variable (V) regions encoding a single-chain Fv (scFv) or single domain antibodies to the N-terminus of the phage coat protein pIII using a phage vector based on the genome of fd-tet. The scFv sequence was cloned in frame with gene III and downstream of the gene III signal sequence, which normally directs export of the adsorption protein. For display of the Ab-pIII product, limited expression must be triggered, and the fusion must be incorporated into phage carrying the phagemid sequence. The former can be achieved by relieving catabolite repression (including glucose in the culture medium by addition of an extra transcriptional terminator or use of the phage shock promoter), the latter by using the phage packaging signal also carried on the phagemid and a helper phage, such as VCSM13, which supplies all structural proteins. Since the helper phage genome encodes wild-type pIII, typically over 90% of rescued phage displays have no Ab at all, and the vast majority of the rescued phage particles that do display the fusion product will only contain a single copy. This monovalent display is essential when selecting Abs of higher affinity.

Example 5: Gold Nanoparticle-Phage Conjugation

Gold-conjugated phages, obtained by coupling of gold particles to the proteins of the phage wall are used. Insertless phage (fd-tet) and phage displaying the targeting peptide on the surface of its pIII protein were amplified in host bacteria and purified. The Au nanoparticle solution was prepared following the citrate reduction procedure (Frens G. Nature Phy. Sci. 1973, 241, 20-22). Assembly of Au-phage complexes began with $10^7$ transducing units (TU) of phage. 25 μL $HS—CH_2—COOH$ and 1 μL $HS—C_2H_4—COOH$ and 1 μL $HS—(CH_2)_{10}—COOH$ were added into the solution with slight shaking overnight. The deepened color of the solution was indicative of the modification of the nanoparticle's surface. The result solution was added to phage and allowed to stand for 1 h at room temperature. Finally, the Au-phage complex was purified by centrifugation and ready to use (FIG. 4). The gold-phage probes preserve the virus surface receptor binding and can effectively integrate the unique signal reporting properties of Au nanoparticles. The use of gold-phage-displayed signal domain antibody gives more sensitive detection.

Example 6: Glycan Array Prescreening—Binding Profiles of Influenza Viruses

Before conducting the design of naked-eye detection of influenza virus subtypes by monitoring the scanometric fingerprints on glycan array, the sialoside receptor-binding characteristics of four isolates of the influenza virus, including Cal/09 H1N1, Brisbane H1N1, Brisbane H3N2, and RG14 H5N1 were compared. Twenty nine sialosides including nineteen (2→3 linked) and ten (2→6 linked) glycans, have been synthesized to construe a sialoside microarray on glass slides (FIG. 7) and used to profile the binding specificity of different influenza hemagglutinins The structures of these sialosides are sialyl-terminating oligosaccharides with differing backbone types, chain lengths and branching patterns, also various sialylation, fucosylation and sulfation patterns.

Figure 8:
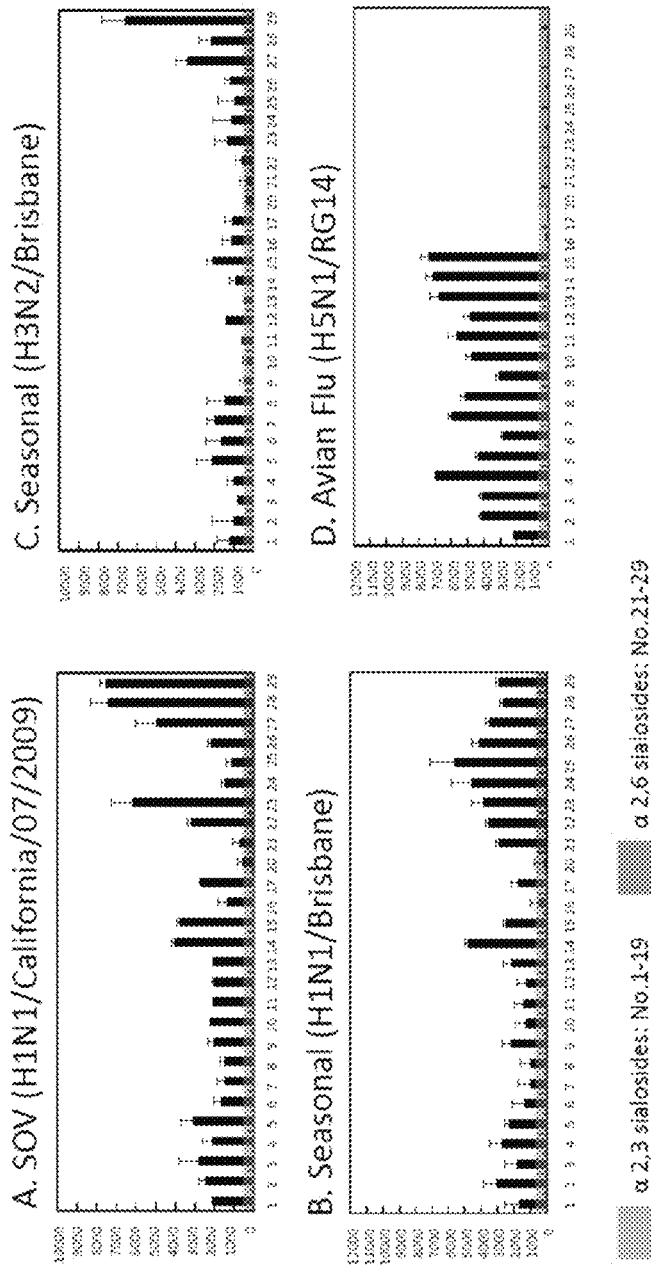
FIG. 8 shows the receptor binding repertoire of the Cal/09 H1N1, Brisbane H1N1, Brisbane H3N2, and RG14H5N1 strains of influenza virus as tested against twenty nine sialosides including nineteen (2→3 linked) and ten (2→6 linked) glycans (according to FIG. 7).
Figure 9:
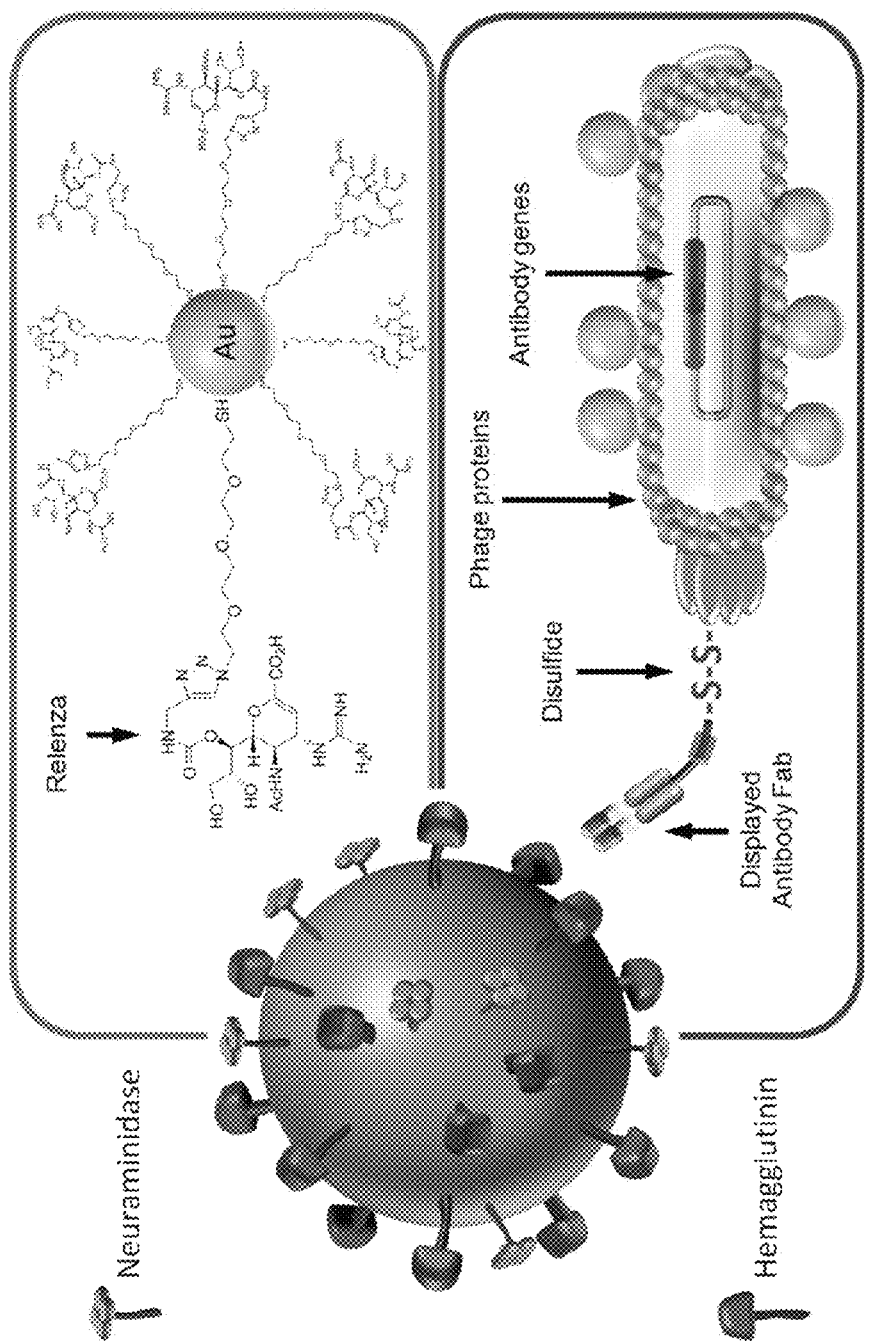
FIG. 9 shows two strategies for making nanoparticle-based probes in influenza virus subtype detection: Relenza-gold nanoparticle complex target neuraminidase (NA) and phage-gold nanoparticle complex target hemagglutinin subtypes (HA).

A clear distinction among the receptor binding repertoire of the Cal/09 H1N1, Brisbane H1N1, Brisbane H3N2, and RG14 H5N1 was observed (FIG. 8). The Cal/09 H1N1 and Brisbane H1N1 viruses bound not only to the majority of α 2,6 linked sialyl sequences but also to a considerable range of α 2,3 linked sialyl sequences. They share similar binding profiles yet differential binding affinities towards α 2,6 sialosides bearing various lengths of sugars. The broader specificity, namely, the ability to bind to α 2,3 in addition to α 2,6 linked receptors was also pertinent to the greater virulence of the pandemic virus, and its capacity to cause severe and fatal disease in humans. In contrast, RG14 H5N1 bound exclusively to α 2,3 linked sialyl sequences. The Brisbane H3N2 influenza viruses showed a preferential binding to α 2,6 linked and α 2,3 linked sialyl sequences with strongest binding toward glycan no. 28 and glycan no. 30. Binding to α 2,3 linked receptors is thought to be associated with the ability of influenza viruses to infect the lower respiratory tract where there is a greater proportion of α 2,3 vs α 2,6 linked sialyl glycans. After comparing to the binding profiles of testing the four influenza viruses (Cal/09 H1N1, Brisbane H1N1, Brisbane H3N2, and RG14 H5N1), a minimum set of nine sialosides containing 8, 9, 19, 22, 23, 24, 25, 27, 30 was suggested to be useful for classifying the serotype of influenza viruses.

Figure 3A:
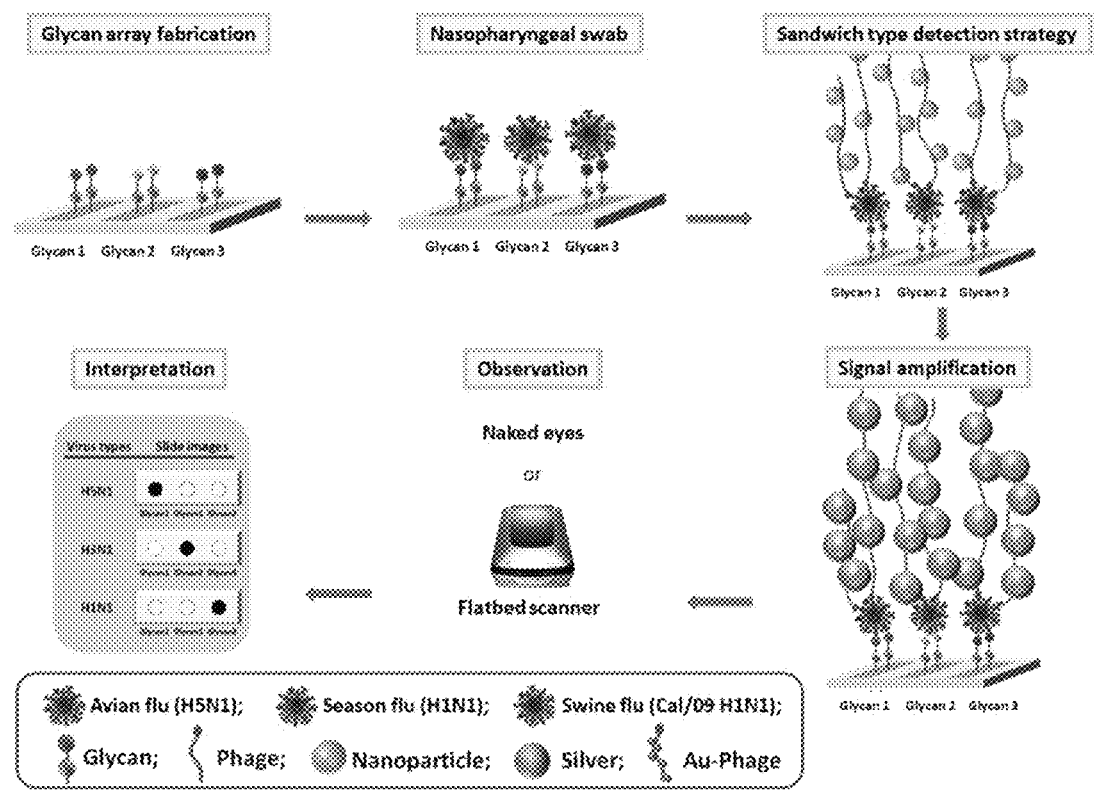
Figure 3B:
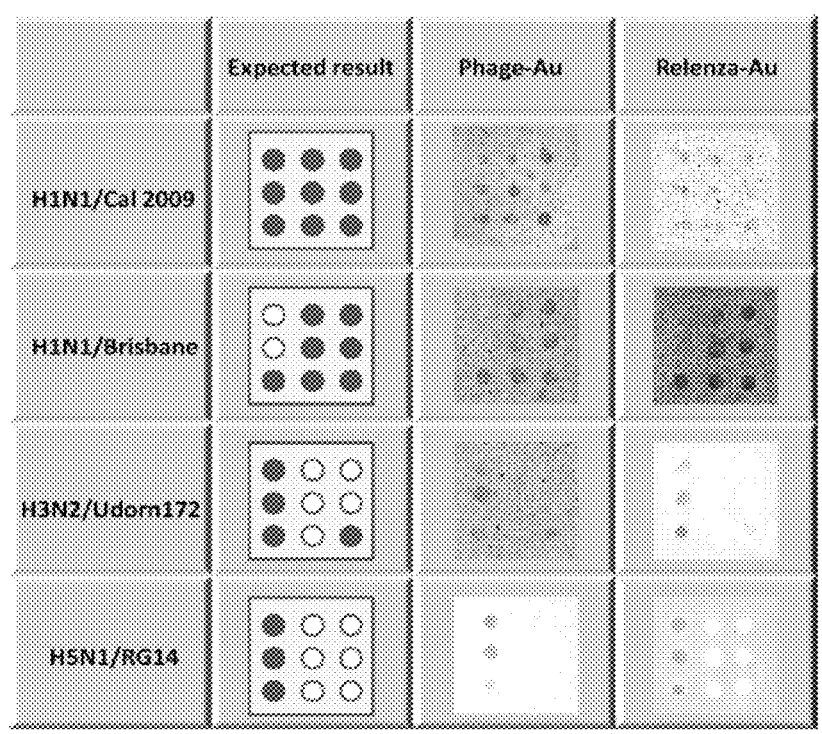
FIG. 3B shows the fingerprint patterns of glycan array for each influenza serotype tested.
Figure 4:
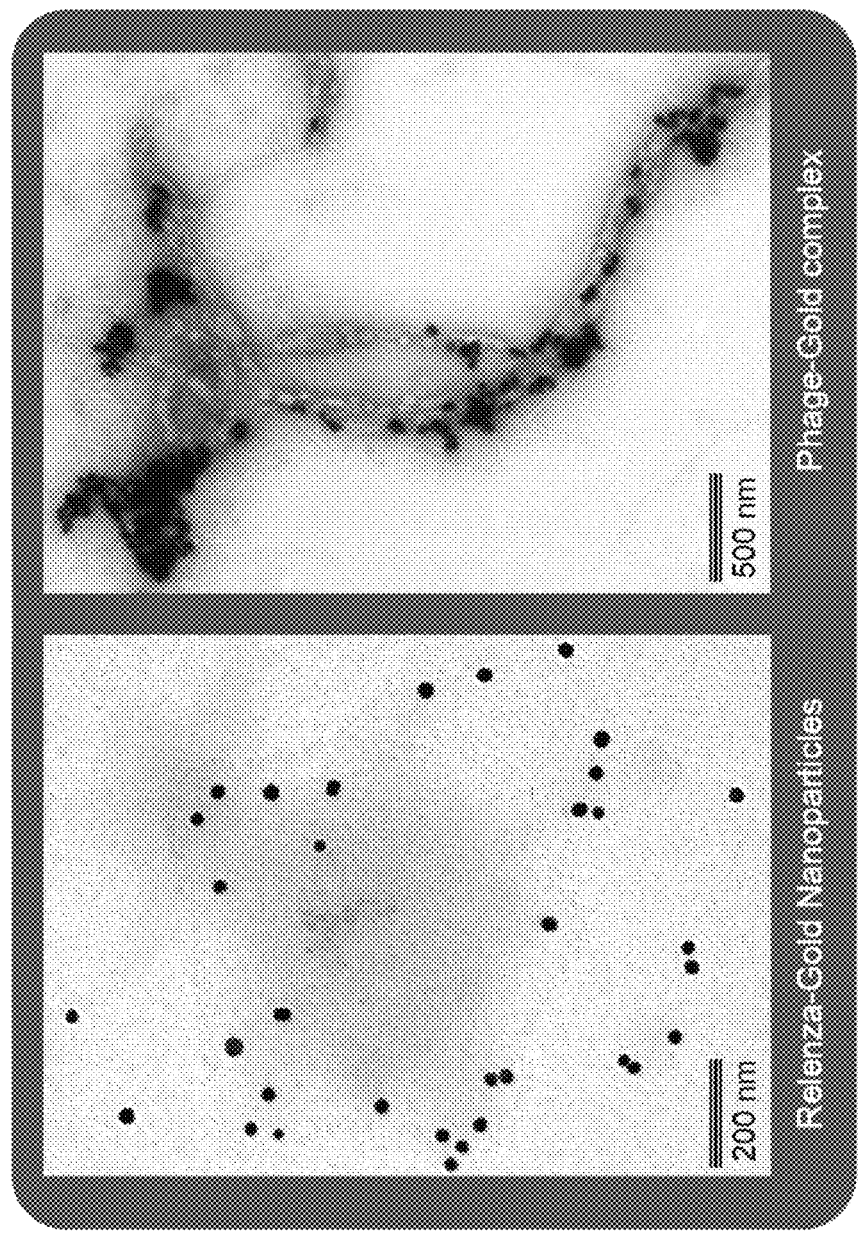
FIG. 4 shows TEM image of gold nanoparticle (left panel) and Au-phage (right panel).
Figure 5:
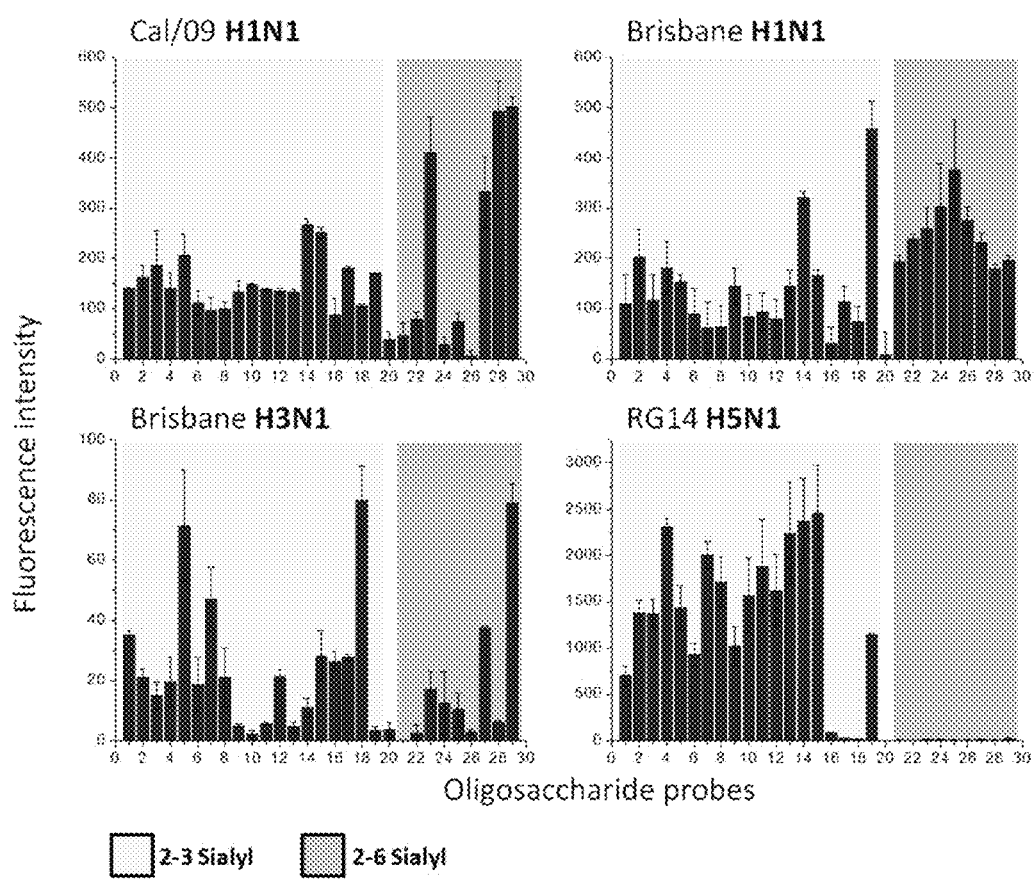
FIG. 5 shows glycan array analyses of the four viruses investigated. Numerical scores for the binding signals are shown as means of duplicate spots at 100 μM per spot (with error bars). The arrays consisted of twenty night sialylated oligosaccharide probes, printed on NHS-coated glass slides (NHS: N-Hydroxy Succinimide). These are listed in Table 2 and arranged according to sialic acid linkage, oligosaccharide backbone chain length and sequence. The various types of terminal sialic acid linkage are indicated by the colored panels as defined at the bottom of the figure.

Example 7: Fingerprints of Each Influenza Virus Subtype—Differential Receptor Binding of Influenza Viruses Minimum numbers of glycans needed to provide a convenient and efficient profiling system to differentiate influenza virus subtypes were determined. According the previous screening results obtained from glycan array, we constructed a small-scale glycan array in α 3×3 matrix format. A set of nine sialosides: 8, 9, 19, 22, 23, 24, 25, 27 and 30 were immobilized on the glass slide and used to capture virus particles. Glycans with different structures can target HA specific to Cal/09 H1N1, Brisbane H1N1, Brisbane H3N2 and RG14 H5N1. After influenza virus incubation, anti-HA antibodies, Relenza-Au (targeting NA), or phage-Au complex (targeting HA) were subsequently added to glass slide for virus stain (FIG. 3A). The patterns of glycan array for each influenza serotype were predicted as their characteristic fingerprint shown in FIG. 3B. Results of small-scale glycan array show that influenza A serotypes can be observed by naked eyes in the case of Relenza-Au and phage-Au and distinguishable by their fingerprint patterns. Identical experiments were further confirmed by fluorophore assay using anti-HA antibody.

Example 8: Screening Result for Single Virus

Figure 6:
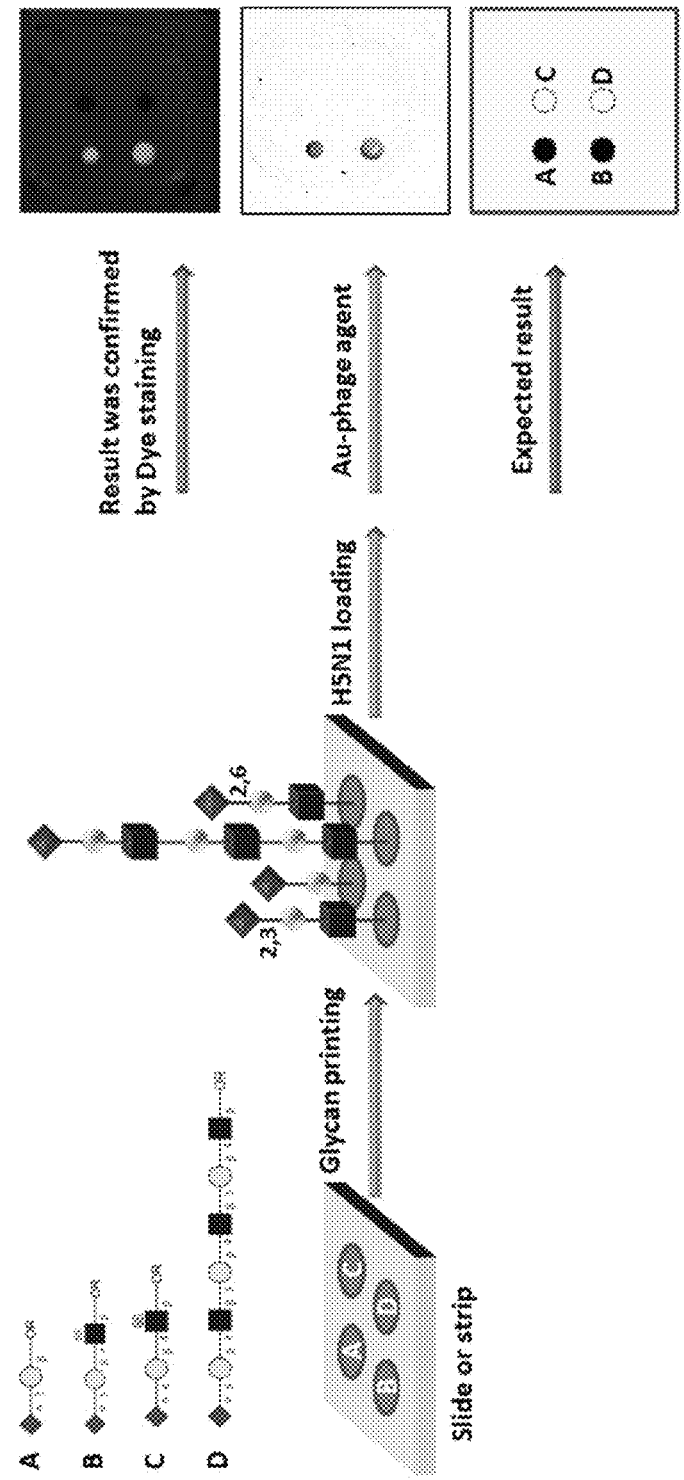
FIG. 6 shows a procedure for H5N1 fingerprint pattern construction.

To demonstrate the feasibility of the method, a glycan array in α 2×2 matrix format was constructed. A and B spots were immobilized with α 2-3 glycans as positive signal for H5N1 screening (FIG. 6). C and D spots were immobilized with α 2-6 glycans as negative control. After H5N1 virus incubation, gold-phage agent was added to slide for virus stain. A dark-round signal was shown up within a min and observed by naked eye. An identical experiment was further confirmed by fluorophore assay.

Figure 10:
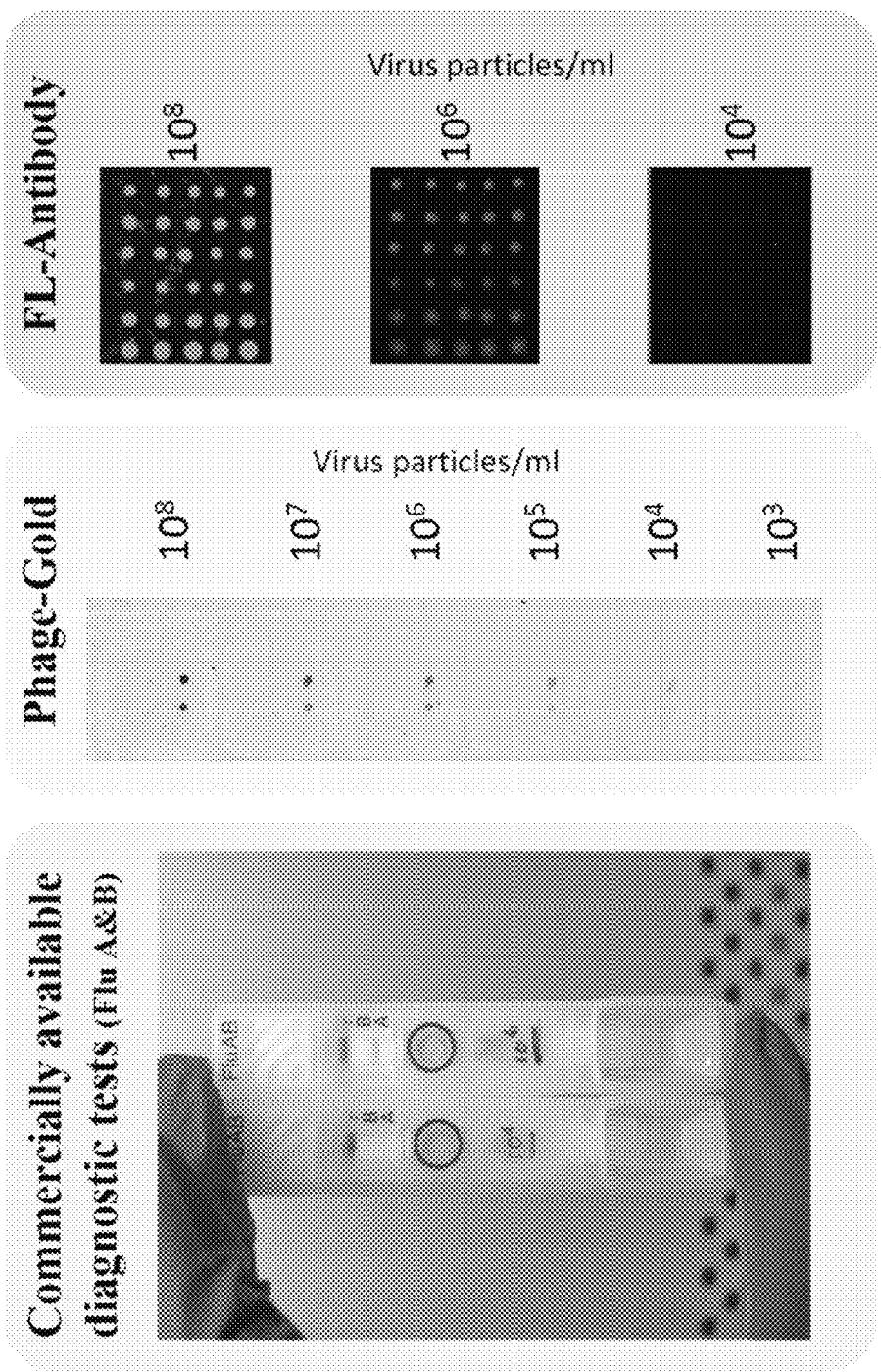
FIG. 10 shows detection limits of the Flu A&B test, GNBSSGA and the analogous fluorophore glycan array system.

Example 9: Specificity of Gold Nanoparticle Based Small Scale Glycan Array (GNBSSGA) for Distinguishing Virus Types To assess the accuracy of visual inspection provided by GNBSSGA, RG14 H5N1 and HK/415742 were mixed as a co-infection sample. The effectiveness of GNBSSGA & Flurophore A&B tests as influenza serotype indicators were compared and to see if they readily distinguished between seasonal influenza virus. Experimental results demonstrated that we were able to identify co-infection viruses with fingerprint patterns through the nanoparticle-based analysis on the glycan array. (FIG. 10) On the contrary, Flu A&B tests detect influenza type A viruses but do not discriminate between virus subtypes. Therefore, a positive result in any of these Flu A&B tests in a patient suspected of type A flu must be further subtyped.

Determination of GNBSSGA Detection Limit:

The pandemic outbreak has highlighted the need for a rapid influenza diagnostic test to facilitate early treatment of infected individuals because treatment has been beneficial only when antiviral drugs are administered within 48 hours of the appearance of symptoms. Rapid and sensitivity influenza diagnostic tests can provide results in a clinically relevant time frame to assist clinical judgment. We therefore sought to compare the analytical sensitivity of GNBSSGA and commercially available influenza rapid tests for the detection of H5N1.

The evaluation of the detection limits of the GNBSSGA & commercial available QuickVue Influenza A+B test established with serial dilution of H5N1 indicated that the lowest detectable viral load of the HN1 by the GNBSSGA, Quick-Vue test, and the analogous fluorophore system of small scale glycan array was 1E3, 1E6, and 1E5 particles/ml, respectively. Therefore, the GNBSSGA test was the most sensitive test in the present study for the detection of influenza virus. Since the GNBSSGA test can be completed rapidly and does not require extensive laboratory facilities, it may be helpful in the timely detection of influenza A virus infections. This suggests that the GNBSSGA test could be used to aid clinical decision making in primary health care settings during outbreaks of influenza.

Example 10: Differential Receptor Binding of HAs from Seasonal and Pandemic Influenza Viruses Our ultimate goal is to differentiate influenza virus subtypes by only a specific set of glycans. In this respect, recombinant HAs from the seasonal and pandemic viruses were examined with respect to their receptor binding specificity. The results of binding profiles for HAs from both pandemic H1N1 (California/07/2009) (FIG. 11A) and seasonal H1N1 Brisbane/59/2007 (Br/59/07) (FIG. 11B) displayed similar pattern, with both higher binding activities toward longer α2,6 sialosides. It was noticed that the maximum binding affinity of the 2009 pandemic H1 reached with α2,6 sialoside containing 5 or 7 sugar units. Yet the H1 from Brisbane strains showed the highest binding affinity towards the α2,6 sialoside containing 7 sugar units. The surface dissociation constant values (KD, surf) were further determined using glycan microassay based on the Langmuir isotherms. (Liang, P. H. et al. *J. Amer. Chem. Sci.* 2007, 129, 11177-11184). The monovalent HA-sialoside binding is weak, exhibiting solution dissociation constants in the millimolar range (KD=2.5×10-3 M) if competition based experiments were conducted. (Sauter, N. K. et al. *Biochemistry* 1989, 28, 8388-8396.) HA, however, is involved in multivalent interactions with sialosides on the host cell surface, which can be seen in the quantitative array profiling. (Wang, C. C. et al. *Proc. Natl. Acad. Sci. USA* 2009, 106, 18137-18142; Liang, P. H. et al. *J. Amer. Chem. Sci.* 2007, 129, 11177-11184). By the analysis of KD, surf (Table 1) of both strains, the result revealed stronger binding capability of H1 from Br/59/07 than the H1 from 2009 pandemic strain toward α2,6 sialosides, and this observation was also supported by the phenomena that Br/59/07 H1 showed a high binding affinity even when the protein was used as low as nM concentrations for sugars 29 and 30, making it difficult for the KD determination.

Figure 11:
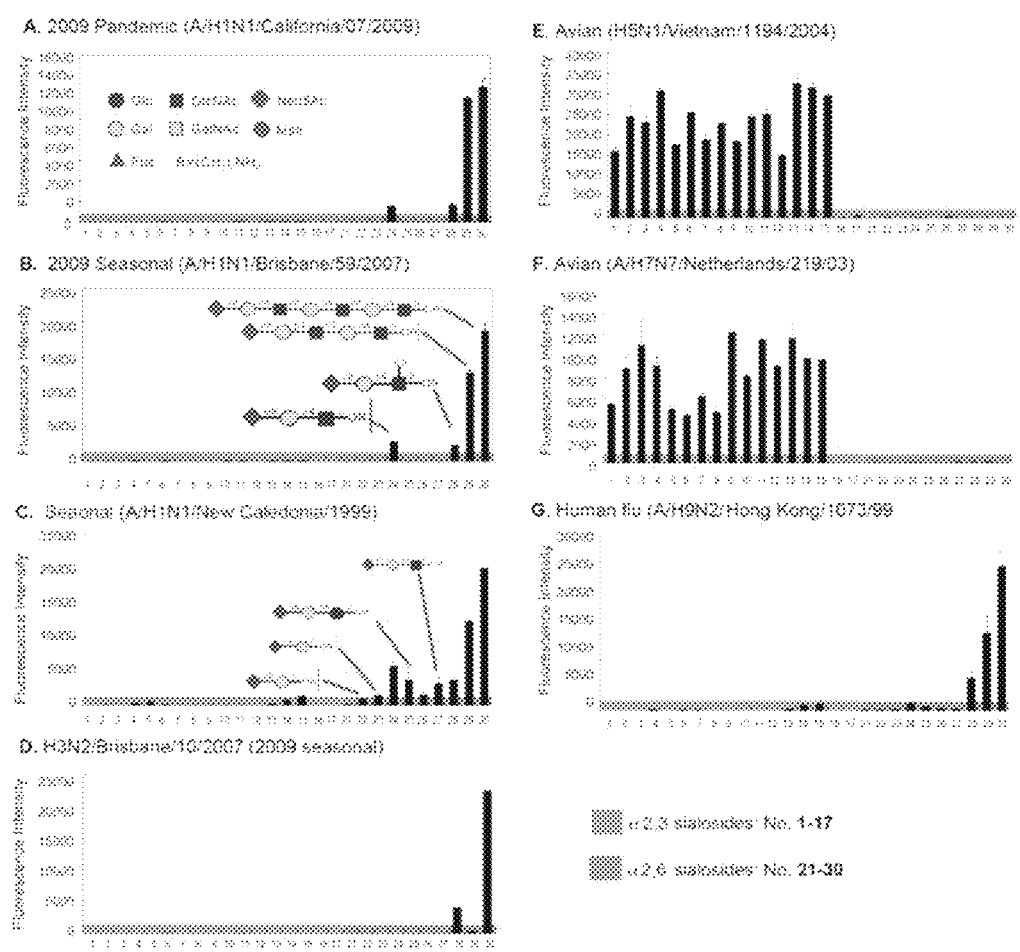
FIG. 11 shows differential binding patterns of HA from H1N1, H3N2, H5N1, H7N7, and H9N2 viruses.

(FIG. 11G). As expected, the HAs from human and avian viruses showed respective binding profiles. The results also suggested that binding to 28 and 30 is unique to human viruses, but not avian viruses. Furthermore, H1 binds glycan 24 (FIGS. 11A-C) while H3 shows no binding (FIG. 11D), thereby providing diagnostic potential for the differentiation of H1 from H3. In addition, binding to the disaccharides 22 and 23 may imply strong foothold among human populations. These sugars, together with α2,3-trisaccharides, can be used to differentiate HA subtypes and thus have the potential to provide a method of quick test upon emergence of an influenza outbreak.

Example 11: Binding Profiles of Real Viruses

In order to understand the relationship of real viruses and HA proteins toward sialosides binding, receptor-binding profiles of four isolates of the influenza virus by glycan array analysis were compared directly by using the same sialosides array. A clear distinction among the receptor-binding repertoire of the Cal/09 H1N1, Brisbane H1N1, Brisbane H3N1, and RG14 H5N1 was observed (FIG. 12). The Cal/09 H1N1 (FIG. 12A) and Brisbane H1N1 viruses (FIG. 12B) bound not only to the majority of α2,6 linked sialyl sequences, but also to a considerable range of α2,3 linked sialyl sequences. In contrast, H5N1 (FIG. 12D) bound exclusively to α2,3 linked sialyl sequences. Similar to

TABLE 1

$K_D$ of HA from SOV and Seasonal flu towards α2,6-sialosides.

| Sugar | Structure | $K_{D, surf}$ of Hemagglutinin (nM) | | |
|---|---|---|---|---|
| | | Cal07(H1N1) | Br59 (H1N1) | Br10 (H3N2) |
| 24 | α6—β4—β—OR | 376 ± 40 | 233 ± 23 | 6350 ± 110 |
| 28 | 6S; α6—β4—β—OR | 1307 ± 533 | 443 ± 156 | 2011 ± 746 |
| 29 | α6—β4—β3—β4—β—OR | 383 ± 9 | N.D.* | >10⁵ |
| 30 | α6—β4—β3—β4—β3—β4—β—OR | 686 ± 230 | N.D.* | 836 ± 96 |

*High binding activities but no concentration-dependence was observed.

Compared to the earlier circulating strain H1N1/New Caledonia/1999 (NC/99) (FIG. 11C), it was shown that recent H1N1 strains showed strong binding affinities towards specific long α2,6 sialosides such as 29 and 30, implying possibility that broader receptor specificity necessitate efficient transmission of influenza virus. On the other hand, the H3 from Brisbane/10/2007 (Br/10/07) showed a narrower binding profile towards only two α2,6 sialosides, 28 and 30. The binding can be observed with sialoside 30, the glycan contains three repeats of LacNAc, but not 29 with two LacNAc repeats (FIG. 11D).

The same array was also used to profile the binding pattern of avian flu H5 (H5N1/Vietnam/1194/2004) (FIG. 11E), avian flu H7 (A/H7N7/Netherlands/219/03) (FIG. 11F), and human flu H9 (A/H9N2/Hong Kong/1073/99)

recombinant H3 proteins, the H3N2 influenza viruses showed a preferential binding to α2,6 linked and α2,3 linked sialyl sequences with strongest binding towards 28 and 30 (FIG. 12C). Interestingly, influenza B showed a similar binding profile to both α2,3 and α2,6 sialosides (FIG. 12E). The broader specificity, namely, the ability to bind to α2,3 in addition to α2,6 linked receptors was also pertinent to the greater virulence of the pandemic virus, and its capacity to cause severe and fatal disease in humans. Binding to α2,3 linked receptors is thought to be associated with the ability of influenza viruses to infect the lower respiratory tract where there is a greater proportion of α2,3 vs α2,6 linked sialyl glycans. Differences in receptor binding among the viruses may therefore formulate a good candidate for classifying the serotype of influenza viruses.

The binding preference of RG14 was the same as that of recombinant H5. In the case of H1N1 virus, the binding profile using the whole virus is slightly different from the profile obtained with recombinant proteins. Like recombinant HAs, viruses showed the strongest binding toward long α2,6 sialosides. However, the viruses also showed significant binding to α2,3 sialosides, which was unusual for recombinant HAs. The intrinsic binding affinity of sialosides for the hemagglutinin is dominated by polyvalent interactions at the cell surface. Therefore, weak monovalent binding may become significant in multivalent interactions, and protein presentation, such as HA orientation and density, on cell surface may have a major impact in receptor recognition. Furthermore, the tip of the globular region harbors the receptor-binding pocket, which is known to be crucial for the process of virus binding to its receptor. The orientation, quantity, and structure of N-glycans neighboring the receptor-binding pocket appear to be important regulators of receptor specificity, which may also cause the differences in binding preferences between recombinant HA and whole virus.

Example 12: Microarray Analysis of Sugar Binding Activities of Hemagglutinin

Microarrays were prepared by printing (AD3200, BioDot) the glycan with an amide tail to the NHS-activated glass slide (Nexterion H) by robotic pin (SMP2B, TeleChem International Inc.). Nexterion H slides were spotted with solutions of sugar 1-17 and 21-30 at 100 µM from bottom to top with 12 replicates horizontally in each grid and dried under vacuum. The spotted slides were blocked with ethanolamine in sodium borate for 1 hour just before use followed with three washes of 0.05% Tween 20 in PBS buffer (pH 7.4) (PBST). A solution of hemagglutinin at 50 µg/mL in PBST was pre-mixed with Cy3-labeled streptavidin in 1:1 molar ratio for 1 h prior to incubation of the preformed complexes with the slides for another hour. After six washes with PBST, one wash with PBS, and three washes with distilled water, the slides were air-dried and scanned with α 532 laser using a microarray fluorescence scanner (GenePix 4000B, Molecular Devices). The PMT gain was set to 600. The resulting images were analyzed with GenePix Pro 6.0 (Molecular Devices) to locate and quantify the fluorescence intensity of all of the spots on the grid. The median of fluorescence intensity of each spot was taken to calculate the median value of binding activities towards each sugar (12 replicates for each sugar). The medians from at least three independent experiments were averaged for the figures. For KD determination, the preformed complexes were serially diluted for binding reaction, (Srinivasan A., et al. *Proc. Natl. Acad. Sci. USA* 2008, 105, 2800-2805) and the binding intensities were quantified at various concentrations of complexes and fitted to the Langumir isotherms using the Prism (GraphPad, San Diego, Calif.). (Liang, P. H. et al. *J. Am. Chem. Soc.* 2008, 130, 12348-12354).

Example 13: Virus Binding Assay Procedure

Influenza virus A/Vietnam/1194/2004 RG14 (H5N1), A/California/7/2009 (H1N1), A/Brisbane/10/2007 (H1N1) and A/Brisbane/10/2007 (H3N2) were from Taiwan CDC. Influenza virus B/Lee/40 was obtained from ATCC (Manassas, Va., USA) and propagated. Printed slides were analyzed without any further modification. Inactivated whole virus was applied at a concentration of about $10^7$ virus/mL in PBS buffer containing the neuraminidase inhibitor Oseltamivir carboxylate (10 µM). Suspensions of the inactivated viruses with Oseltamivir carboxylate were overlaid onto the arrays and incubated at room temperature for 1 h. Slides were subsequently washed by successive rinses in PBS-0.05% Tween, PBS, and deionized water three times. Bound viruses were detected using the following antibodies: homemade rabbit anti-H1 antibody both for SOV California/07/2009 and H1N1 Brisbane; anti-H3 antibody for H3N2 Brisbane (NR3118, Biodefence and Emerging Infections Research Resources Repository, National Institute of Allergy and Infectious Diseases, MD, USA); anti-H5 (α-293s) (Sino Biological Inc. Beijing, CH) antibody for H5N1 (RG14), and anti-flu B (Abcam, Mass., USA) for B/Lee/40. The slides were gently rocked at room temperature for 60 min. After the repeating washing steps, binding was detected by overlay with labeled secondary antibodies.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claim.

What is claimed is:

1. A method for detecting at least one influenza serotype in a sample suspected of or comprising one or more viruses, the method comprising the steps of:
    a) providing a substrate having at least one type of glycan capture probe bound at a discrete location on the substrate, wherein the capture probes can bind to a specific influenza serotype target;
    b) providing at least one type of nanoparticle probe conjugated to a detector moiety, wherein the detector moiety binds to the specific influenza serotype;
    c) contacting the substrate with the sample suspected of comprising one or more viruses and the nanoparticle probe under conditions suitable for the binding of the glycan capture probes to the specific influenza serotype and the binding of the nanoparticle probe to the specific influenza serotype to form a complex at the discrete location on the substrate; and
    d) detecting the presence or absence of the complex wherein the presence or absence of the complex is indicative of the presence or absence of the specific influenza serotype in the sample;
    wherein the nanoparticle consists essentially of a noble metal, and
    wherein the limit of detection of at least one influenza serotype in said sample suspected of or comprising one or more viruses is less than $10^4$ viral particles.

2. The method of claim 1, wherein the influenza serotype is selected from the group consisting of influenza A, influenza B, influenza A serotypes H1N1, H2N2, H3N1, H3N2, H5N1, H7N7, H1N2, H9N2, H7N2, H7N3, and H10N7.

3. The method of claim 1, wherein the substrate comprises an array of a plurality of glycan capture probes that bind specifically to a plurality of different influenza serotypes.

4. The method of claim 3, wherein the plurality of capture probes comprises one or more sialosides which is selected from the group consisting of: Neu5Ac(α2-3)Gal(β1-3)GalNAcα, Neu5Ac(α2-3)Gal(β1-6)Manα, Neu5Ac(α2-3)Fuc(α1-4)Gal(β1-4)Glcβ, Neu5Ac(α2-6)Galβ, Neu5Ac (α2-6)GalNAcβ, Neu5Ac(α2-6)Gal(β1-4)GlcNAcβ, Neu5Ac(α2-6)Gal(β1-4)Glcβ, Neu5Ac(α2-6)Gal(β1-4)GlcNAcβ, and Neu5Ac(α2-6)Gal(β1-4)GlcNAc(β1-3) Gal(β1-4)GlcNAc(β1-3)Gal(β1-4)GlcNAcβ.

5. The method of claim 4, wherein the capture probes are able to differentially bind to influenza subtypes Cal/09 H1N1, Brisbane H1N1, Brisbane H3N2, and RG14 H5N1.

6. The method of claim 1, wherein the detector moiety comprises an antibody fragment that binds to the specific influenza serotype.

7. The method of claim 6, wherein the antibody fragment comprises a phage particle from a phage display, and the phage particle comprises a plurality of nanoparticles.

8. The method of claim 7, wherein the antibody fragment recognizes a hemagglutinin (HA) characteristic of an influenza subtype.

9. The method of claim 1, wherein the detector moiety comprises a molecule that binds specifically to one or more influenza serotypes.

10. The method of claim 6, wherein the antibody fragment recognizes a neuraminidase (NA) characteristic of an influenza subtype.

11. The method of claim 9, wherein the molecule is a neuraminidase binding agent.

12. The method of claim 11, wherein the molecule is selected from Oseltamivir (Tamiflu), Zanamivir (Relenza), Laninamivir (Inavir), or Peramivir.

13. The method of claim 11, wherein the neuraminidase binding agent detects co-infection by at least two different strains of influenza viruses.

14. A method for distinguishing between a first influenza virus serotype and a second influenza virus serotype in a sample comprising a first influenza virus serotype and a second influenza virus serotype, the method comprising the steps of:
 a) providing a substrate having at least two different types of glycan capture probes bound at discrete locations on the substrate, wherein a first capture probe can bind to the first influenza virus serotype but not the second influenza virus serotype, and a second capture probe can bind to the second influenza virus serotype but not the first influenza virus serotype;
 b) providing at least one type of nanoparticle probe comprising detector moieties, wherein the detector moieties on each type of nanoparticle probe has a configuration that can bind to both the first influenza virus serotype and the second influenza serotype;
 c) contacting the substrate with the sample under conditions suitable for binding of the first influenza virus serotype and the second influenza virus serotype in the sample to the glycan capture probes, and under suitable conditions for the binding of the nanoparticle probe to the first influenza serotype or second influenza serotype;
 d) contacting the first influenza virus serotype and the second influenza virus serotype immobilized on the substrate with the nanoparticle probe under conditions that are effective for the binding of the detector moieties to the first influenza virus serotype and the second influenza virus serotype; and
 e) detecting whether the nanoparticle probe binds to the first influenza virus serotype and/or the second influenza virus serotype at the discrete locations on the substrate where the first capture probe is located and where the second capture probe is located, wherein the presence or absence of the nanoparticle-first influenza virus serotype complex at the discrete location on the substrate where the first capture probe is located is indicative of the presence or absence of the specific first influenza virus serotype in the sample, and the presence or absence of the nanoparticle-second influenza virus serotype complex at the discrete location on the substrate where the second capture probe is located is indicative of the presence or absence of the specific second influenza virus serotype in the sample;
 wherein the nanoparticle consists essentially of a noble metal.

15. The method of claim 1 or 14, wherein the sample is blood, serum, anti-serum, monoclonal antibody preparation, lymph, plasma, saliva, urine, semen, breast milk, ascites fluid, tissue extract, cell lysate, cell suspension, viral suspension, nasopharyngeal aspirate, or a combination thereof.

16. The method of claim 14, wherein the detector moiety comprises an antibody fragment that binds to the first influenza serotype or the second influenza serotype.

17. The method of claim 16, wherein the antibody fragment thereof comprises a phage particle from a phage display, and the phage particle comprises a plurality of nanoparticles.

18. The method of claim 14, wherein the captured nanoparticle-first influenza virus serotype or nanoparticle-second influenza virus serotype complex is detected by photonic, electronic, acoustic, opto-acoustic, gravity, electro-chemical, electro-optic, mass-spectrometric, enzymatic, chemical, biochemical, or physical means.

19. The method of claim 1 or 14, wherein the nanoparticles are made of gold or silver.

20. The method of claim 19, wherein the nanoparticles are made of gold.

21. The method of claim 1 or 14, wherein the substrate is a magnetic bead.

22. The method of claim 1 or 14, wherein the substrate has a planar surface.

23. The method of claim 1 or 14, wherein the substrate is made of glass, quartz, ceramic, or plastic.

24. The method of claim 1 or 14, wherein the detecting comprises contacting the substrate with specific metal stain.

25. The method of claim 1 or 14, wherein the detecting comprises detecting light scattered by the nanoparticle.

26. The method of claim 1 or 14, wherein the detecting comprises observation with an optical scanner.

27. The method of claim 26, wherein the scanner is linked to a computer loaded with software capable of calculating grayscale measurements, and the grayscale measurements are calculated to provide a quantitative measure of the amount of target analyte or influenza serotype detected.

28. The method of claim 1 or 14, wherein the substrate is addressable.

29. The method of claim 1 or 14, wherein a plurality of glycan capture probes, each of which can recognize a different target influenza serotype, are attached to the substrate in an array of discrete spots.

30. The method of claim 29, wherein the plurality of glycan capture probes comprise glycan structures of at least 10%, 15%, 20%, 25%, 30%, 35%, 40%, 45%, 50%, 55%, 60%, 65%, 70%, 75%, 80%, 85%, 90%, 95%, or more of glycans found on HA receptors in human upper respiratory tract tissues.

31. The method of claim 29, wherein the plurality of glycan capture probes comprises a glycan structure of at least one molecule selected from:
 Neu5Ac(α2-3)Galβ, Neu5Ac(α2-3)Gal(β1-4)Glcβ, Neu5Ac(α2-3)Gal(β1-4)GlcNAcβ, Neu5Ac(α2-3)Gal(β1-4)(6S)GlcNAcβ, Neu5Ac(α2-3)Gal(β1-4)[Fuc (α1-3)]GlcNAcβ, Neu5Ac(α2-3)Gal(β1-3)GlcNAcβ, Neu5Ac(α2-3)Gal(β1-3)(6S)GlcNAcβ, Neu5Ac(α2-3)Gal(β1-3)GalNAcα, Neu5Ac(α2-3)Gal(β1-6)Manα, Neu5Ac(α2-3)Gal(β1-3)GalNAc(β1-3)Galα, Neu5Ac(α2-3)Gal(β1-3)GalNAc(β1-3)Galβ, Neu5Ac(α2-3)Gal(β1-3)GalNAc(β1-3)Gal(α1-4)Gal(β1-4)Glcβ, Neu5Ac(α2-3)Gal(β1-6)[Neu5Ac(α2-3)Gal(β1-3)]GlcNAcβ, Neu5Ac(α2-3)Gal(β1-6)[Neu5Ac(α2-3)Gal(β1-3)]Manα, Neu5Ac(α2-3)Gal(β1-3)[Neu5Ac(α1-6)]GlcNAcβ Neu5Ac(α2-3)[GalNAc(β1-4)]Gal(β1-4)Glcβ, Gal(β1-3)GalNAc(β1-4)[Neu5Ac(α1-3)]Gal(β1-4)Glcβ, Fuc(α1-2)Gal(β1-3)GalNAc(β1-4)[Neu5Ac(α1-3)]Gal(β1-4)Glcβ, Neu5Ac(α2-3)Fuc(α1-4)Gal(β1-4)Glcβ, Neu5Acα, Neu5Ac(α2-6)Galβ, Neu5Ac(α2-6)GalNAcβ, Neu5Ac(α2-6)Gal(β1-4)GlcNAcβ, Neu5Ac(α2-6)Gal(β1-4)Glcβ, Neu5Ac(α2-6)Gal(β1-4)GalNAcα, Neu5Ac(α2-6)Gal(β1-3)GlcNAcβ, Neu5Ac(α2-6)Gal(β1-4)(6S)GlcNAcβ, Neu5Ac(α2-6)Gal(β1-4)GlcNAc(β1-3)Gal(β1-4)GlcNAcβ, and Neu5Ac(α2-6)Gal(β1-4)GlcNAc(β1-3)Gal(β1-4)GlcNAc(β1-3)Gal(β1-4)GlcNAcβ.

32. The method of claim 29, wherein the plurality of capture probes comprises one or more of sialosides which is selected from the group consisting of:
Neu5Ac(α2-3)Gal(β1-3)GalNAcα, Neu5Ac(α2-3)Gal(β1-6)Manα, Neu5Ac(α2-3)Fuc(α1-4)Gal(β1-4)Glcβ, Neu5Ac(α2-6)Galβ, Neu5Ac(α2-6)GalNAcβ, Neu5Ac(α2-6)Gal(β1-4)GlcNAcβ, Neu5Ac(α2-6)Gal(β1-4)Glcβ, Neu5Ac(α2-6)Gal(β1-4)GlcNAcβ, and Neu5Ac(α2-6)Gal(β1-4)GlcNAc(β1-3) Gal(β1-4)GlcNAc(β1-3)Gal(β1-4)GlcNAcβ.

33. The method of claim 32, wherein the capture probes are able to differentially bind to influenza subtypes Cal/09 H1N1, Brisbane H1N1, Brisbane H3N2, and RG14 H5N1.

34. The method of claim 14, wherein the detector moiety comprises an antibody fragment that binds to the specific influenza serotype.

35. The method of claim 34, wherein the antibody fragment comprises a phage particle from a phage display.

36. The method of claim 35, wherein the antibody fragment recognizes a hemagglutinin (HA) characteristic of an influenza subtype.

37. The method of claim 14, wherein the detector moiety comprises a molecule that binds specifically to one or more influenza serotypes.

38. The method of claim 34, wherein the antibody fragment recognizes a neuraminidase (NA) characteristic of an influenza subtype.

39. The method of claim 37, wherein the molecule is a neuraminidase binding agent.

40. The method of claim 39, wherein the molecule is selected from Oseltamivir (Tamiflu), Zanamivir (Relenza), Laninamivir (Inavir), or Peramivir.

41. The method of claim 39, wherein the neuraminidase binding agent detects co-infection by at least two different types of influenza viruses.

42. The method of claim 14, wherein the substrate is selected from the group consisting essentially of one of glass, semiconductor, organic polymer, membrane, quartz, silicon, mineral, metal, metal alloy, gold, silver, and mixtures and compositions thereof.

43. The method of claim 1 or 14, wherein sample is first contacted with the nanoparticle probe so that a influenza virus serotype present in the sample binds to the detector moiety on the nanoparticle probe, and the influenza virus serotype bound to the nanoparticle probe is then contacted with the substrate so that the influenza virus serotype binds to the glycan capture probe on the substrate.

44. The method of claim 1 or 14, wherein sample is first contacted with the substrate so that a influenza virus serotype present in the sample binds to a glycan capture probe, and the influenza virus serotype bound to the glycan capture probe is then contacted with the nanoparticle probe so that the influenza virus serotype binds to the detector moiety on the nanoparticle probe.

45. The method of claim 1 or 14, wherein the sample, the nanoparticle probe and the glycan capture probe on the substrate are contacted simultaneously.

46. The method of claim 1, wherein detecting the presence or absence of the complex indicative of the presence or absence of the specific influenza serotype in the sample comprises evaluating a flu vaccination response in an individual from whom the sample is obtained.

\* \* \* \* \*